United States Patent
Saint-Remy

(10) Patent No.: US 11,718,650 B2
(45) Date of Patent: Aug. 8, 2023

(54) IMMUNOGENIC PEPTIDES AND THEIR USE IN IMMUNE DISORDERS

(71) Applicant: IMCYSE SA, Liège (BE)

(72) Inventor: Jean-Marie Saint-Remy, Grez-Doiceau (BE)

(73) Assignee: IMCYSE SA, Liège (BE)

( * ) Notice: Subject to any disclaimer, the term of this patent is extended or adjusted under 35 U.S.C. 154(b) by 550 days.

(21) Appl. No.: 16/848,086

(22) Filed: Apr. 14, 2020

(65) Prior Publication Data

US 2020/0317742 A1    Oct. 8, 2020

Related U.S. Application Data

(62) Division of application No. 14/976,259, filed on Dec. 21, 2015, now Pat. No. 10,662,232, which is a division of application No. 12/377,048, filed as application No. PCT/EP2007/007165 on Aug. 13, 2007, now Pat. No. 9,249,202.

(30) Foreign Application Priority Data

Aug. 11, 2006 (GB) ..................................... 0615966
May 25, 2007 (GB) ..................................... 0710081
Jun. 13, 2007 (GB) ..................................... 0711403

(51) Int. Cl.
| | |
|---|---|
| A61K 35/17 | (2015.01) |
| C07K 14/47 | (2006.01) |
| C07K 14/435 | (2006.01) |
| A61K 39/00 | (2006.01) |
| A61K 39/35 | (2006.01) |
| C07K 14/415 | (2006.01) |
| C07K 14/62 | (2006.01) |
| C12N 9/08 | (2006.01) |
| C12N 9/88 | (2006.01) |

(52) U.S. Cl.
CPC .......... *C07K 14/4713* (2013.01); *A61K 35/17* (2013.01); *A61K 39/0008* (2013.01); *A61K 39/35* (2013.01); *C07K 14/415* (2013.01); *C07K 14/43531* (2013.01); *C07K 14/47* (2013.01); *C07K 14/4717* (2013.01); *C07K 14/62* (2013.01); *C12N 9/0065* (2013.01); *C12N 9/88* (2013.01); *A61K 2039/572* (2013.01); *C07K 2319/00* (2013.01); *C12Y 111/01008* (2013.01); *C12Y 401/01015* (2013.01)

(58) Field of Classification Search
None
See application file for complete search history.

(56) References Cited

U.S. PATENT DOCUMENTS

| | | | |
|---|---|---|---|
| 4,599,231 A | 7/1986 | Milich et al. | |
| 4,886,782 A | 12/1989 | Good et al. | |
| 5,433,948 A | 7/1995 | Thomas et al. | |
| 5,552,142 A | 9/1996 | Thomas et al. | |
| 5,589,175 A | 12/1996 | Vahlne et al. | |
| 5,633,234 A | 5/1997 | August et al. | |
| 5,736,142 A | 4/1998 | Sette et al. | |
| 5,770,202 A | 6/1998 | Thomas et al. | |
| 5,773,002 A | 6/1998 | Thomas et al. | |
| 5,863,528 A | 1/1999 | Hawley et al. | |
| 6,399,383 B1 | 6/2002 | Apt et al. | |
| 6,602,509 B1* | 8/2003 | Saint-Remy ............ A61P 11/02 530/324 |
| 6,656,471 B1 | 12/2003 | Sastry et al. | |
| 6,759,046 B1 | 7/2004 | Gaudernack et al. | |
| 7,157,089 B1 | 1/2007 | Mizzen et al. | |
| 7,306,804 B2 | 12/2007 | Sastry et al. | |
| 7,780,882 B2 | 8/2010 | Chang et al. | |

(Continued)

FOREIGN PATENT DOCUMENTS

| | | |
|---|---|---|
| JP | 2004147649 A | 5/2004 |
| WO | WO-8504103 A1 | 9/1985 |

(Continued)

OTHER PUBLICATIONS

Abrahimians, E.M., et al., "MHC Class II-Restricted Epitopes Containing an Oxidoreductase Activity Prompt CD4+ T Cells with Apoptosis-Inducing Properties," Frontiers in Immunology, 6:1-5, Frontiers Research Foundation, Switzerland (Sep. 2015).

(Continued)

*Primary Examiner* — Michael Szperka
(74) *Attorney, Agent, or Firm* — Nixon & Vanderhye, PC

(57) ABSTRACT

The present invention provides novel peptides and homologues thereof. The peptides of the invention comprise (i) a T-cell epitope of an antigen (self or non-self) with a potential to trigger an immune reaction presented by a class II major histocompatibility complex (MHC) determinant and recognised by CD4+ T cell more specifically of an allergen or auto-antigen, coupled, optionally through the use of a linker to (ii) an amino acid sequence having a reducing activity, such as a thioreductase sequence. The peptides of the invention have been shown to be useful a medicine, more in particular for the prevention or treatment of immune disorders, more specifically of allergic disorders or autoimmune diseases. The present invention thus provides for the use of said peptides for the manufacture of a medicament for the prevention or treatment of an immune disorder and further provides for methods of treatment or preventing immune disorders by using said peptides. The present invention also provides for compositions comprising said peptides.

8 Claims, 24 Drawing Sheets

Specification includes a Sequence Listing.

(56) References Cited

U.S. PATENT DOCUMENTS

| | | |
|---|---|---|
| 8,999,346 B2 | 4/2015 | Saint-Remy |
| 9,044,507 B2 | 6/2015 | Saint-Remy |
| 9,248,171 B2 | 2/2016 | Saint-Remy |
| 9,249,202 B2 | 2/2016 | Saint-Remy |
| 9,394,517 B2 | 7/2016 | Saint-Remy |
| 9,861,661 B2 | 1/2018 | Saint-Remy |
| 10,023,847 B2 | 7/2018 | Saint-Remy |
| 10,617,748 B2 | 4/2020 | Saint-Remy |
| 10,662,232 B2 | 5/2020 | Saint-Remy |
| 10,729,791 B2 | 8/2020 | Saint-Remy et al. |
| 10,808,016 B2 | 10/2020 | Vander Elst et al. |
| 10,899,795 B2 | 1/2021 | Saint-Remy |
| 10,982,196 B2 | 4/2021 | Saint-Remy |
| 11,193,114 B2 * | 12/2021 | Saint-Remy ........... A61K 39/12 |
| 11,226,332 B2 | 1/2022 | Saint-Remy et al. |
| 11,407,795 B2 | 8/2022 | Vander Elst et al. |
| 11,485,768 B2 | 11/2022 | Vander Elst |
| 2003/0049723 A1 | 3/2003 | Zhang et al. |
| 2003/0104570 A1 | 6/2003 | Cabezon et al. |
| 2003/0129205 A1 | 7/2003 | Saint-Remy et al. |
| 2003/0152581 A1 | 8/2003 | Saint-Remy et al. |
| 2004/0077045 A1 | 4/2004 | Zhang et al. |
| 2005/0032039 A1 | 2/2005 | Sastry et al. |
| 2005/0107256 A1 | 5/2005 | Barnwell et al. |
| 2005/0196386 A1 | 9/2005 | Blazar et al. |
| 2005/0202044 A1 | 9/2005 | Mizzen et al. |
| 2006/0182763 A1 | 8/2006 | Kim et al. |
| 2006/0211091 A1 | 9/2006 | Zhang et al. |
| 2006/0216301 A1 | 9/2006 | Tahara et al. |
| 2006/0269561 A1 | 11/2006 | Paterson et al. |
| 2007/0160620 A1 | 7/2007 | Mizzen et al. |
| 2007/0184023 A1 | 8/2007 | Rasmussen et al. |
| 2008/0176247 A1 | 7/2008 | Chou et al. |
| 2009/0012004 A1 | 1/2009 | Sette et al. |
| 2010/0033088 A1 | 2/2010 | Hwang et al. |
| 2010/0068193 A1 | 3/2010 | Brunsvig et al. |
| 2010/0183652 A1 | 7/2010 | Page et al. |
| 2010/0203083 A1 | 8/2010 | Lux et al. |
| 2010/0303866 A1 | 12/2010 | Saint-Remy |
| 2010/0330088 A1 | 12/2010 | Saint-Remy |
| 2011/0002903 A1 | 1/2011 | Saint-Remy |
| 2011/0110964 A1 | 5/2011 | Saint-Remy |
| 2011/0111395 A1 | 5/2011 | Saint-Remy |
| 2011/0111502 A1 | 5/2011 | Saint-Remy |
| 2012/0009678 A1 | 1/2012 | Saint-Remy |
| 2013/0095133 A1 | 4/2013 | Klatzmann et al. |
| 2013/0259885 A1 | 10/2013 | Saint-Remy |
| 2014/0370044 A1 | 12/2014 | Saint-Remy |
| 2014/0377299 A1 | 12/2014 | Saint-Remy |
| 2015/0110821 A1 | 4/2015 | Saint-Remy |
| 2015/0216901 A1 | 8/2015 | Saint-Remy |
| 2016/0091492 A1 | 3/2016 | Saint-Remy et al. |
| 2016/0108103 A1 | 4/2016 | Saint-Remy |
| 2016/0194367 A1 | 7/2016 | Saint-Remy |
| 2016/0250255 A1 | 9/2016 | Saint-Remy et al. |
| 2016/0339121 A1 | 11/2016 | Saint-Remy et al. |
| 2017/0100466 A1 | 4/2017 | Saint-Remy |
| 2018/0228912 A1 | 8/2018 | Saint-Remy et al. |
| 2018/0258154 A1 | 9/2018 | Saint-Remy et al. |
| 2018/0346887 A1 | 12/2018 | Saint-Remy |
| 2019/0106477 A1 | 4/2019 | Vander |
| 2019/0352348 A1 | 11/2019 | Vander Elst et al. |
| 2020/0103407 A1 | 4/2020 | Saint-Remy et al. |
| 2020/0179499 A1 | 6/2020 | Saint-Remy |
| 2020/0270331 A1 | 8/2020 | Saint-Remy |
| 2020/0317742 A1 | 10/2020 | Saint-Remy et al. |
| 2020/0397911 A1 | 12/2020 | Saint-Remy et al. |
| 2020/0407406 A1 | 12/2020 | Vander Elst et al. |
| 2021/0188913 A1 | 6/2021 | Saint-Remy |
| 2021/0401976 A1 | 12/2021 | Erak et al. |
| 2022/0119778 A1 | 4/2022 | Saint-Remy |
| 2022/0288179 A1 | 9/2022 | Erak |
| 2022/0411476 A1 | 12/2022 | Vander Elst et al. |

FOREIGN PATENT DOCUMENTS

| | | |
|---|---|---|
| WO | WO-9205800 A1 | 4/1992 |
| WO | WO-9308279 A1 | 4/1993 |
| WO | WO-9405790 A1 | 3/1994 |
| WO | WO-9626265 A1 | 8/1996 |
| WO | WO-9740852 A1 | 11/1997 |
| WO | WO-9958552 A2 | 11/1999 |
| WO | WO-0029008 A2 | 5/2000 |
| WO | WO-0155393 A2 | 8/2001 |
| WO | WO-0170263 A1 | 9/2001 |
| WO | WO-0200892 A1 | 1/2002 |
| WO | WO-02095051 A2 | 11/2002 |
| WO | WO-02097070 A1 | 12/2002 |
| WO | WO-03072731 A2 | 9/2003 |
| WO | WO-2004018667 A1 | 3/2004 |
| WO | WO-2004024766 A1 | 3/2004 |
| WO | WO-2005012502 A2 | 2/2005 |
| WO | WO-2005037190 A2 | 4/2005 |
| WO | WO-2005039613 A1 | 5/2005 |
| WO | WO-2005042575 A2 | 5/2005 |
| WO | WO-2005086781 A2 | 9/2005 |
| WO | WO-2006009920 A2 | 1/2006 |
| WO | WO-2006059529 A1 | 6/2006 |
| WO | WO-2007027954 A2 | 3/2007 |
| WO | WO-2007104715 A2 | 9/2007 |
| WO | WO-2007135684 A2 | 11/2007 |
| WO | WO-2008017517 A1 | 2/2008 |
| WO | WO-2009042215 A3 | 7/2009 |
| WO | WO-2009100505 A1 | 8/2009 |
| WO | WO-2009101201 A2 | 8/2009 |
| WO | WO-2009101204 A2 | 8/2009 |
| WO | WO-2009101205 A2 | 8/2009 |
| WO | WO-2009101206 A2 | 8/2009 |
| WO | WO-2009101207 A1 | 8/2009 |
| WO | WO-2009101208 A2 | 8/2009 |
| WO | WO-2009106073 A2 | 9/2009 |
| WO | WO-2010037395 A2 | 4/2010 |
| WO | WO-2010115046 A2 | 10/2010 |
| WO | WO-2012069568 A2 | 5/2012 |
| WO | WO-2013113076 A1 | 8/2013 |
| WO | WO-2013121296 A1 | 8/2013 |
| WO | WO-2014191432 A1 | 12/2014 |
| WO | WO-2015063176 A1 | 5/2015 |
| WO | WO-2016059236 A1 | 4/2016 |
| WO | WO2017182528 A1 | 10/2017 |
| WO | WO2020229703 A1 | 11/2020 |
| WO | WO2021144478 A2 | 7/2021 |
| WO | WO2021148683 A2 | 7/2021 |
| WO | WO2021224397 A1 | 11/2021 |
| WO | WO2021224403 A1 | 11/2021 |

OTHER PUBLICATIONS

Abrahimians, E.M., et al., "Thioreductase-Containing Epitopes Inhibit the Development of Type 1 Diabetes in the NOD Mouse Model," Frontiers in Immunology, 7:1-10, Frontiers Research Foundation, Switzerland (Mar. 2016).

Advisory Action dated Apr. 9, 2013, in U.S. Appl. No. 12/735,754, Saint-Remy, J.M., filed Aug. 13, 2010, 3 Pages.

Advisory Action dated Feb. 4, 2019, in U.S. Appl. No. 14/976,259, Saint-Remy, J.M., filed Dec. 21, 2015, 3 pages.

Advisory Action dated Jul. 3, 2017, in U.S. Appl. No. 14/686,855, Saint-Remy, J.M., filed Apr. 15, 2015, 3 Pages.

Advisory Action dated Jun. 27, 2014, in U.S. Appl. No. 12/735,739, Saint-Remy, J.M., filed Aug. 13, 2010, 3 pages.

Advisory Action dated Mar. 2, 2020, in U.S. Appl. No. 14/450,722, Saint-Remy, J.M., filed Aug. 4, 2014, 3 Pages.

Advisory Action dated Mar. 20, 2017, in U.S. Appl. No. 14/589,134, Saint-Remy, J.M., filed Jan. 5, 2015, 3 pages.

Advisory Action dated May 9, 2018, in U.S. Appl. No. 14/450,722, Saint-Remy, J.M., filed Aug. 4, 2014, 3 pages.

Advisory Action dated Oct. 22, 2013, in U.S. Appl. No. 12/735,740, Saint-Remy, J.M., filed Aug. 13, 2010, 3 pages.

Advisory Action dated Oct. 3, 2019, in U.S. Appl. No. 14/450,722, Saint-Remy, J.M., filed Aug. 4, 2014, 3 pages.

(56) References Cited

OTHER PUBLICATIONS

Advisory Action dated Sep. 9, 2019, in U.S. Appl. No. 15/388,398, Saint-Remy, J.M., filed Dec. 22, 2016, 12 Pages.
Aleksza, M., et al., "Altered Cytokine Expression of Peripheral Blood Lymphocytes in Polymyositis and Dermatomyositis," Annals of the Rheumatic Diseases, 64(10):1485-1489, BMJ, England (Oct. 2005).
Aley, S.B. and Gillin, F.D., "Giardia Lamblia: Post-Translational Processing and Status of Exposed Cysteine Residues in TSA 417, A Variable Surface Antigen," Experimental Parasitology, 77(3):295-305, Academic Press, United States (Nov. 1993).
Ali-Khan, N., et al., "Overview of Proteome Analysis," Current Protocols in Protein Science, 30(1):22.1.1-22.1.19, Hoboken, NJ : Wiley Interscience, United States (Dec. 2002).
Apostolou, I., et al., "Evidence for Two Subgroups of CD4-CD8-NKT Cells With Distinct TCR Alpha Beta Repertoires and Differential Distribution in Lymphoid Tissues," Journal of Immunology, 165(5):2481-2490, American Association of Immunologists, United States (Sep. 2000).
Appella, E., et al., "Analysis of the Structure of Naturally Processed Peptides Bound by Class I and Class II Major Histocompatibility Complex Molecules," EXS, 73:105-119, Birkhäuser Verlag, Switzerland (1995).
Arunachalam, B., et al., "Enzymatic Reduction of Disulfide Bonds in Lysosomes: Characterization of a Gamma-interferon-inducible Lysosomal Thiol Reductase (GILT)," Proceedings of the National Academy of Sciences of the United States of America, 97(2):745-750, National Academy of Sciences, United States (Jan. 2000).
Ascherio, A., "Environmental Factors in Multiple Sclerosis," Expert Review of Neurotherapeutics, 13(12 Suppl):3-9, Taylor & Francis, England (Dec. 2013).
Azoury-Ziadeh, R., et al., "T-Helper Epitopes Identified Within the E6 Transforming Protein of Cervical Cancer-Associated Human Papillomavirus Type 16," Viral Immunology, 12(4):297-312, Mary Ann Liebert, Inc., United States (1999).
Balato, A., et al., "Natural Killer T Cells: an Unconventional T-Cell Subset With Diverse Effector and Regulatory Functions," The Journal of Investigative Dermatology, 129(7):1628-1642, Elsevier, United States (Jul. 2009).
Batten, P., et al., "Immune Response to Stem Cells and Strategies to Induce Tolerance," Philosophical Transactions of the Royal Society of London. Series B, Biological Sciences, 362(1484):1343-1356, Royal Society, England (Aug. 2007).
Boisgerault, F., et al., "Differential Roles of Direct and Indirect Allorecognition Pathways in the Rejection of Skin and Corneal Transplants," Transplantation, 87(1):16-23, Lippincott Williams & Wilkins, United States (Jan. 2009).
Bolivar, J., et al., "Molecular Cloning of a Zinc Finger Autoantigen Transiently Associated With Interphase Nucleolus and Mitotic Centromeres and Midbodies. Orthologous Proteins With Nine CXXC Motifs Highly Conserved From Nematodes to Humans," The Journal of Biological Chemistry, 274(51):36456-36464, American Society for Biochemistry and Molecular Biology, United States (Dec. 1999).
Bower, M.S., et al., "Two Members of the Thioredoxin-h Family Interact With the Kinase Domain of a *Brassica* S Locus Receptor Kinase," The Plant Cell, 8(9):1641-1650, American Society for Biochemistry and Molecular Biology, United States (Sep. 1996).
Braun, M.Y. et al., "Acute Rejection in the Absence of Cognate Recognition of Allograft by T Cells," Journal of Immunology, 166(8):4879-4883, American Association of Immunologists, United States (Apr. 2001).
Brinks, V., et al., "Immunogenicity of Therapeutic Proteins: The Use of Animal Models," Pharmaceutical Research, 28(10):2379-2385, Kluwer Academic/Plenum Publishers, United States (Oct. 2011).
Brinster, C. and Shevach, E.M., "Bone Marrow-Derived Dendritic Cells Reverse the Anergic State of CD4+CD25+ T Cells without Reversing Their Suppressive Function," Journal of Immunology, 175(11):7332-7340, American Association of Immunologists, United States (Dec. 2005).
Brinster, C. and Shevach, E.M., "Costimulatory Effects of IL-1 on the Expansion/differentiation of CD4+CD25+Foxp3+ and CD4+CD25+Foxp3- T Cells," Journal of Leukocyte Biology, 84(2):480-487, Wiley on behalf of the Society for Leukocyte Biology, United States (Aug. 2008).
Cao, O., et al., "Prevention of Gene Transfer-Induced Inhibitor Formation by Nasal Administration of Human F.IX T Cell Epitope in a Murine Model of Hemophilia B," Blood, 104(11):414, Nov. 2004).
Capon, D.J. and Ward, R.H., "The CD4-gp120 Interaction and Aids Pathogenesis," Annual Review of Immunology, 9:649-678, Annual Reviews Inc., United States (1991).
Carlier, V.A., et al., "Control of Asthma by in Vitro-Induced Allergen-Specific Regulatory T Cells in the Mouse," Munksgaard Allergy, 65:555, Jun. 2007).
Carlier, V.A., et al., "Increased Synapse Formation Obtained by T cell Epitopes Containing a CxxC Motif in Flanking Residues Convert CD4+ T Cells into Cytolytic Effectors," PLOS One, 7(10):e45366, Public Library of Science, United States (Oct. 2012).
Caro-Aguilar, I., et al., "Chimeric Epitopes Delivered by Polymeric Synthetic Linear Peptides Induce Protective Immunity to Malaria," Microbes and Infection, 7(13):1324-1337, Elsevier, France (Oct. 2005).
Castano, A.R., et al., "Peptide Binding and Presentation by Mouse CD1," Science, 269(5221):223-226, American Association for the Advancement of Science, United States (Jul. 1995).
Cavone, L., et al., "Long-Term Suppression of EAE Relapses by Pharmacological Impairment of Epitope Spreading," British Journal of Pharmacology, 171(6):1501-1509, Wiley, England (Mar. 2014).
Celis, E., et al., "Identification of Potential CTL Epitopes of Tumor-associated Antigen MAGE-1 for Five Common HLA-A Alleles," Molecular Immunology, 31(18):1423-1430, Pergamon Press, England (Dec. 1994).
Celis, E., et al., "Induction of Anti-Tumor Cytotoxic T Lymphocytes in Normal Humans Using Primary Cultures and Synthetic Peptide Epitopes," Proceedings of the National Academy of Sciences of the United States of America, 91(6):2105-2109, National Academy of Sciences, United States (Mar. 1994).
Chapter III Immune Molecules.
Chen, T.C., et al., "Induction of Dominant Transplantation Tolerance by an Altered Peptide Ligand of the Male Antigen Dby," The Journal of Clinical Investigation, 113(12):1754-1762, American Society for Clinical Investigation, United States (Jun. 2004).
Chen, X., et al., "Glucocorticoid Amplifies IL-2-Dependent Expansion of Functional FoxP3(+)CD4(+)CD25(+) T Regulatory Cells in Vivo and Enhances Their Capacity to Suppress EAE," European Journal of Immunology, 36(8):2139-2149, Wiley-VCH, Germany (Aug. 2006).
Chuanlin ed., Molecular Immunology, pp. 428-429, 433-436, 15 pages, Fudan University Press, Shanghai Medical College Press, (May 2001) (English Language Translation Provided).
Co-pending U.S. Appl. No. 16/892,588, filed Jun. 4, 2020.
Corthay, A., "CD4+ T Cells Cooperate With Macrophages for Specific Elimination of MHC Class II-Negative Cancer Cells," Advances in Experimental Medicine and Biology, 590:195-208, Kluwer Academic/Plenum Publishers, United States (2007).
Cotton, N.J., et al., "Oxidative Inhibition of Human Soluble Catechol-O-Methyltransferase," The Journal of Biological Chemistry, 279(22):23710-23718, American Society for Biochemistry and Molecular Biology, United States (May 2004).
Credo Reference, 2012.
Crellin, N.K., et al., "Altered Activation of AKT is Required for the Suppressive Function of Human CD4+CD25+ T Regulatory Cells," Blood, 109(5):2014-2022, American Society of Hematology, United States (Mar. 2007).
Crompton, P.D., et al., "Advances and Challenges in Malaria Vaccine Development," The Journal of Clinic Investigation, 120(12):4168-4178, American Society for Clinical Investigation, United States (Dec. 2010).

(56) References Cited

OTHER PUBLICATIONS

Davids, B.J., et al., "A New Family of Giardial Cysteine-rich Non-VSP Protein Genes and a Novel Cyst Protein," PLoS One, 1:e44, Public Library of Science, United States (Dec. 2006).
Davids, M.M., et al., "Interrogating the Repertoire: Broadening the Scope of Peptide-MHC Multimer Analysis," Nature Reviews. Immunology, 11(8):551-558, Nature Pub. Group, England (Jul. 2011).
De Groot, A.S. and Scott, D.W., "Immunogenicity of Protein Therapeutics," Trends in Immunology, 28(11):482-490, Elsevier Science Ltd., England (Nov. 2007).
De La Cruz, V.F., et al., "The Immunologic Significance of Variation Within Malaria Circumsporozoite Protein Sequences," Journal of Immunology, 142(10):3568-3575, American Association of Immunologists, United States (May 1989).
DermNet NZ, 2019.
Desmetz, C., et al., "Proteomics-Based Identification of HSP60 as a Tumor-Associated Antigen in Early Stage Breast Cancer and Ductal Carcinoma in situ," Journal of Proteome Research, 7(9):3830-3837, American Chemical Society, United States (Sep. 2008).
Dobrzanski, M.J., "Expanding Roles for CD4 T Cells and Their Subpopulations in Tumor Immunity and Therapy," Frontiers in Oncology, 3:1-19, Frontiers Research Foundation, Switzerland (Mar. 2013).
Dobrzynski, E., et al., "Prevention of Cytotoxic T Lymphocyte Responses to Factor IX-Expressing Hepatocytes by Gene Transfer-induced Regulatory T Cells," Proceedings of the National Academy of Sciences of the United States of America, 103(12):4592-4597, National Academy of Sciences, United States (Mar. 2006).
Eberl, G., et al., "Tissue-specific Segregation of CD1d-dependent and CD1d-independent NK T Cells," Journal of Immunology, 162(11):6410-6419, American Association of Immunologists, United States (Jun. 1999).
Facktor, M.A., et al., "Hypersensitivity to Tetanus Toxoid," The Journal of Allergy and Clinical Immunology, 52(1):1-12, Mosby, United States (Jul. 1973).
Fan, C.F. and Mei, X.G., "Co-Immunization of BALB/c Mice With Recombinant Immunogens Containing G Protein Fragment and Chimeric CTL Epitope of Respiratory Syncytial Virus Induces Enhanced Cellular Immunity and High Level of Antibody Response," Vaccine, 23(35):4453-4461, Elsevier Science, Netherlands (Aug. 2005).
Final Office Action dated Jun. 30, 2020, in U.S. Appl. No. 14/375,324, Saint-Remy, J.M., filed Jul. 29, 2014, 10 pages.
Final Office Action dated Nov. 5, 2019, in U.S. Appl. No. 14/450,722, Saint-Remy, J.M., filed Aug. 4, 2014, 8 Pages.
Final Office Action dated Apr. 15, 2019, in U.S. Appl. No. 15/388,398, Saint-Remy, J.M., filed Dec. 22, 2016, 15 pages.
Final Office Action dated Aug. 31, 2016 in U.S. Appl. No. 12/735,739, Saint-Remy, J.M., filed Aug. 13, 2010, 12 Pages.
Final Office Action dated Aug. 7, 2019, in U.S. Appl. No. 15/516,045, Saint-Remy, J.M., et al., filed Mar. 31, 2017, 5 pages.
Final Office Action dated Aug. 9, 2012, in U.S. Appl. No. 12/377,048, Saint-Remy, J.M., filed Feb. 10, 2009, 9 pages.
Final Office Action dated Dec. 2, 2016, in U.S. Appl. No. 14/589,134, Saint-Remy, J.M., filed Jan. 5, 2015, 14 pages.
Final Office Action dated Dec. 28, 2016, in U.S. Appl. No. 13/988,925, Saint-Remy, J.M., filed Jun. 6, 2013, 5 pages.
Final Office Action dated Dec. 28, 2017, in U.S. Appl. No. 14/450,722, Saint-Remy, J.M., filed Aug. 4, 2014, 10 pages.
Final Office Action dated Feb. 13, 2019, in U.S. Appl. No. 15/516,045, Saint-Remy, J.M., et al., filed Mar. 31, 2017, 5 pages.
Final Office Action dated Feb. 20, 2014 in U.S. Appl. No. 12/735,739, Saint-Remy, J.M., filed Aug. 13, 2010, 10 Pages.
Final Office Action dated Jan. 19, 2018, in U.S. Appl. No. 14/589,134, Saint-Remy, J.M., filed Jan. 5, 2015, 15 pages.
Final Office Action dated Jan. 20, 2012, in U.S. Appl. No. 12/377,048, Saint-Remy, J.M., filed Feb. 10, 2009, 10 pages.
Final Office Action dated Jan. 8, 2019, in U.S. Appl. No. 14/980,932, Saint-Remy, J.M., filed Dec. 28, 2015.
Final Office Action dated Jul. 10, 2013, in U.S. Appl. No. 12/735,740, Saint-Remy, J.M., filed Aug. 13, 2010, 14 pages.
Final Office Action dated Jun. 5, 2015, in U.S. Appl. No. 12/735,744, Saint-Remy, J.M., filed Aug. 13, 2010, 11 pages.
Final Office Action dated Jun. 6, 2019, in U.S. Appl. No. 14/450,722, Saint-Remy, J.M., filed Aug. 4, 2014, 8 pages.
Final Office Action dated Mar. 19, 2019, in U.S. Appl. No. 15/151,868, Saint-Remy, J.M., et al., filed May 11, 2016, 19 pages.
Final Office Action dated Mar. 23, 2017, in U.S. Appl. No. 14/686,855, Saint-Remy, J.M., filed Apr. 15, 2015, 11 Pages.
Final Office Action dated Mar. 25, 2019, in U.S. Appl. No. 14/375,324, Saint-Remy, J.M., filed Jul. 29, 2014, 14 pages.
Final Office Action dated May 20, 2014, in U.S. Appl. No. 12/735,744, Saint-Remy, J.M., filed Aug. 13, 2010, 10 Pages.
Final Office Action dated Oct. 26, 2018, in U.S. Appl. No. 14/976,259, Saint-Remy, J.M., filed Dec. 21, 2015, 15 pages.
Final Office Action dated Oct. 30, 2017, in U.S. Appl. No. 14/375,324, Saint-Remy, J.M., filed Jul. 29, 2014, 5 Pages.
Final Office Action dated Sep. 26, 2012, in U.S. Appl. No. 12/735,754, Saint-Remy, J.M., filed Aug. 13, 2010, 18 Pages.
Fomenko, D.E. and Gladyshev, V.N., "Identity and Functions of Cxxc-derived Motifs," Biochemistry, 42(38):11214-11225, American Chemical Society, United States (Sep. 30, 2003).
Fournier, P. and Schirrrnacher, V., "Randomized Clinical Studies of Anti-tumor Vaccination: State of the Art in 2008," Expert Review of Vaccines, 8(1):51-66, Taylor & Francis, England (Jan. 2009).
Francois, V., et al., "The CD4(+) T-cell Response of Melanoma Patients to a MAGE-A3 Peptide Vaccine Involves Potential Regulatory T Cells," Cancer Research, 69(10):4335-4345, American Association for Cancer Research, United States (May 15, 2009).
Frankel, A.E., et al., "Characterization of Diphtheria Fusion Proteins Targeted to the Human Interleukin-3 Receptor," Protein Engineering, 13(8):575-581, Oxford University Press, England (Aug. 2000).
Ge, F.F., et al., "An Hsp70 Fusion Protein Vaccine Potentiates the Immune Response Against Japanese Encephalitis Virus," Archives of Virology, 152(1):125-135, Springer-Verlag, Austria (Jan. 2007).
Geluk, A., et al., "HLA-DR Binding Analysis of Peptides From Islet Antigens in IDDM," Diabetes, 47(10):1594-1601, American Diabetes Association, United States (Oct. 1998).
GenBank FPAA051928, 1997, p. 1.
Geneseq Database, Accession No. BDK51134, "Human Preproinsulin (PPI) Antigenic Peptide, SEQ ID 164," XP002770300, Jan. 26, 2017, Retrieved from EBI accession No. GSP:BDK51134.
GenPept PDB 5GSB_A, 2017, pp. 1-2.
Gentile, F., et al., "Thyroglobulin as an Autoantigen: What Can We Learn About Immunopathogenicity From the Correlation of Antigenic Properties With Protein Structure?," Immunology, 112(1):13-25, Blackwell Scientific Publications, England (May 2004).
Girardi, E., et al., "Structure of an A-helical Peptide and Lipopeptide Bound to the Nonclassical Major Histocompatibility Complex (MHC) Class I Molecule CD1d," The Journal of Biological Chemistry, 291(20):10677-10683, American Society for Biochemistry and Molecular Biology, United States (May 13, 2016).
Gross, D.A., et al., "Simple Conditioning With Monospecific CD4+ CD25+ Regulatory T Cells for Bone Marrow Engraftment and Tolerance to Multiple Gene Products," Blood, 108(6):1841-1848, American Society of Hematology, United States (Sep. 15, 2006).
Grossman, W.J., et al., "Differential Expression of Granzymes a and B in Human Cytotoxic Lymphocyte Subsets and T Regulatory Cells," Blood, 104(9):2840-2848, American Society of Hematology, United States (Nov. 2004).
Haga, J.A., et al., "HLA-A, Partial [*Homo sapiens*]," GenBank: AAA59610.1, 1995, p. 1.
Haque, M.A., et al., "Cysteinylation of Mhc Class li Ligands: Peptide Endocytosis and Reduction Within Ape Influences T Cell Recognition," Journal of Immunology (Baltimore, Md. : 1950), 166(7):4543-4551, American Association of Immunologists, United States (Apr. 1, 2001).
Harris, S.J., et al., "Prediction of Murine Mhc Class I Epitopes in a Major House Dust Mite Allergen and Induction of T1-type CD8+ T Cell Responses," International Immunology, 9(2):273-280, Oxford University Press, England (Feb. 1997).

(56) References Cited

OTHER PUBLICATIONS

Haveman, L.M. et al., "Induction and Capture of CD4+ Cytotoxic Adenoviral Specific T-Cells in Response to pan-DR Binding Adenoviral Epitopes; towards Immunotherapy," Blood, 106(11):3238, American Society of Hematology, United States (Nov. 2005).

Haveman, L.M., et al., "Novel Pan-DR-binding T Cell Epitopes of Adenovirus Induce Pro-inflammatory Cytokines and Chemokines in Healthy Donors," International Immunology, 18(11):1521-1529, Oxford University Press, 1989, England (Nov. 2006).

Heemskerk, B., et al., "Adenovirus-specific CD4+ T Cell Clones Recognizing Endogenous Antigen Inhibit Viral Replication in Vitro Through Cognate Interaction," Journal of Immunology (Baltimore, Md. : 1950), 177(12):8851-8859, American Association of Immunologists, United States (Dec. 15, 2006).

Hemmer, B., et al., "Minimal Peptide Length Requirements for CD4(+) T Cell Clones—implications for Molecular Mimicry and T Cell Survival," International Immunology, 12(3):375-383, Oxford University Press, 1989, England (Mar. 2000).

Heurtault, B., et al., "Design of a Liposomal Candidate Vaccine Against Pseudomonas Aeruginosa and Its Evaluation in Triggering Systemic and Lung Mucosal Immunity," Pharmaceutical Research, 26(2):276-285, Kluwer Academic/Plenum Publishers, United States (Feb. 2009).

HLA Nomenclature, 2015.

Ho, L.P., et al., "CD4(−)CD8alphaalpha Subset of CD1d-restricted NKT Cells Controls T Cell Expansion," Journal of Immunology (Baltimore, Md. : 1950), 172(12):7350-7358, American Association of Immunologists, United States (Jun. 2004).

Hohn, H., et al., "CD4+ Tumor-infiltrating Lymphocytes in Cervical Cancer Recognize HLA-DR-restricted Peptides Provided by Human Papillomavirus-E7," Journal of Immunology (Baltimore, Md. : 1950), 163(10):5715-5722, American Association of Immunologists, United States (Nov. 15, 1999).

Hori, S., et al., "Control of Regulatory T Cell Development by the Transcription Factor Foxp3," Science, 299(5609):1057-1061, American Association for the Advancement of Science, United States (Feb. 2003).

Hsu, H.J., et al., "Assessing Computational Amino Acid Beta-turn Propensities With a Phage-displayed Combinatorial Library and Directed Evolution," Structure (London, England : 1993), 14(10):1499-1510, Cambridge, Mass. : Cell Press, United States (Oct. 2006).

Hulo, N., et al., "The PROSITE Database," Nucleic Acids Research 34(Database issue):D227-D230, Oxford University Press, England (Jan. 2006).

International Search Report and Written Opinion for International Application No. PCT/EP2015/074063, European Patent Office, Netherlands, dated Jan. 29, 2016, 8 Pages.

International Search Report and Written Opinion for International Application No. PCT/EP2017/059302, European Patent Office, Netherlands, dated Jun. 26, 2017, 11 Pages.

International Search Report and Written Opinion for International Application No. PCT/EP2018/055501, European Patent Office, Netherlands, dated May 4, 2018, 13 Pages.

International Search Report for International Application No. PCT/BE2008/000010, European Patent Office, Germany, dated Jul. 2, 2008.

International Search Report for International Application No. PCT/BE2013/000006, European Patent Office, Netherlands, dated Jul. 1, 2013, 8 Pages.

International Search Report for International Application No. PCT/EP2007/007165, European Patent Office, Netherlands, dated Jan. 17, 2008.

International Search Report for International Application No. PCT/EP2009/051803, European Patent Office, Netherlands, dated Aug. 11, 2009, 5 Pages.

International Search Report for International Application No. PCT/EP2009/051804, European Patent Office, Netherlands, dated Aug. 11, 2009, 6 Pages.

International Search Report for International Application No. PCT/EP2009/051806, European Patent Office, Netherlands, dated Aug. 11, 2009, 6 Pages.

International Search Report for International Application No. PCT/EP2009/051807, European Patent Office, Netherlands, dated Jul. 13, 2009, 5 Pages.

International Search Report for International Application No. PCT/EP2009/051808, European Patent Office, Netherlands, dated Feb. 18, 2010, 7 Pages.

International Search Report for International Application No. PCT/EP2014/060994, European Patent Office, Netherlands, dated Sep. 18, 2014, 5 pages.

Iqbalsyah, T.M., et al., "The CXXC Motif at the N Terminus of an Alpha-helical Peptide," Protein Science : a Publication of the Protein Society, 15(8):1945-1950, Cold Spring Harbor Laboratory Press, United States (Aug. 2006).

Ise, W., et al., "Naive CD4+ T Cells Exhibit Distinct Expression Patterns of Cytokines and Cell Surface Molecules on Their Primary Responses to Varying Doses of Antigen," Journal of Immunology (Baltimore, Md. : 1950), 168(7):3242-3250, American Association of Immunologists (Apr. 2002).

James, E., et al., "HY Peptides Modulate Transplantation Responses to Skin Allografts," International Immunology, 14(11):1333-1342, Oxford University Press, 1989, England (Nov. 2002).

Janeway, C.A., et al., "Immunobiology, 3rd edition," Garland Press Inc., 1997, p. 11.

Janssens, W., et al., "CD4+CD25+ T Cells Lyse Antigen-presenting B Cells by Fas-fas Ligand Interaction in an Epitope-specific Manner," Journal of immunology (Baltimore, Md. : 1950), 171(9):4604-4612, American Association of Immunologists, United States (Nov. 2003).

Jensen, P.E., "Acidification and Disulfide Reduction Can be Sufficient to Allow Intact Proteins to Bind Class II MHC," Journal of Immunology, 150(8 Pt 1):3347-3356, American Association of Immunologists, United States (Apr. 1993).

Jiang, E.P., et al., "Protection by the Gross Saponins of Tribulus Terrestris Against Cerebral Ischemic Injury in Rats Involves the NF-KB Pathway," Acta Pharmaceutica Sinica B, 1(1):21-26, (Jun. 2011).

Joffre, O., et al., "Induction of Antigen-specific Tolerance to Bone Marrow Allografts With CD4+CD25+ T Lymphocytes," Blood, 103(11):4216-4221, American Society of Hematology, United States (Jun. 1, 2004).

Karin, N., et al., "Reversal of Experimental Autoimmune Encephalomyelitis by a Soluble Peptide Variant of a Myelin Basic Protein Epitope: T Cell Receptor Antagonism and Reduction of Interferon Gamma and Tumor Necrosis Factor Alpha Production," The Journal of Experimental Medicine, 180(6):2227-2237, Rockefeller University Press, United States (Dec. 1, 1994).

Kasprowicz, V., et al., "Tracking of Peptide-specific CD4+ T-cell Responses After an Acute Resolving Viral Infection: a Study of Parvovirus B19," Journal of Virology, 80(22):11209-11217, American Society For Microbiology, United States (Nov. 2006).

Khare, M., et al., "HLA Class II Transgenic Mice Authenticate Restriction of Myelin Oligodendrocyte Glycoprotein-specific Immune Response Implicated in Multiple Sclerosis Pathogenesis," International Immunology, 15(4):535-546, Oxford University Press, 1989, England (Apr. 2003).

Klebanoff, C.A., et al., "Therapeutic Cancer Vaccines: Are We There Yet?," Immunological reviews, 239(1):27-44, Blackwell, England (Jan. 2011).

Kumar, K.V.S.H., et al., "Twins and Endocrinology," Indian Journal of Endocrinology and Metabolism, 18(Suppl 1):S48-S52, Medknow Publications, India (Nov. 2014).

Laforge, M., et al., "HIV/SIV Infection Primes Monocytes and Dendritic Cells for Apoptosis," PLOS Pathogens 7(6):1-16, Public Library of Science, United States (Jun. 2011).

Lamb, J.R., et al., "Human T-Cell Clones Recognize Chemically Synthesized Peptides of Influenza Haemagglutinin," Nature, 300:66-69, Springer, United States (Nov. 1982).

Lewin, A., et al., "Effects of Substitutions in the CXXC Active-site Motif of the Extracytoplasmic Thioredoxin Resa," The Biochemical

(56) References Cited

OTHER PUBLICATIONS

Journal, 414(1):81-91, Published by Portland Press on behalf of the Biochemical Society, England (Aug. 15, 2008).
Li, S.C., et al., "Twisting Immune Responses for Allogeneic Stem Cell Therapy," World Journal of Stem Cells, 1(1):30-35, Baishideng Publishing Group, United States (Dec. 31, 2009).
Lindqvist, C.A., et al., "Both CD4+ FoxP3+ and CD4+ FoxP3− T Cells From Patients With B-cell Malignancy Express Cytolytic Markers and Kill Autologous Leukaemic B Cells in Vitro," Immunology, 133(3):296-306, Blackwell Scientific Publications (Apr. 5, 2011).
Lodish, L., et al., "Molecular Cell Biology, 4th edition." W.H. Freeman & Co Ltd, New York, 2000, Section 6.3, Viruses: Structure, Function, and Uses, 1280 pages.
Louis, S., et al., "Contrasting CD25hiCD4+t Cells/foxp3 Patterns in Chronic Rejection and Operational Drug-free Tolerance," Transplantation, 81(3):398-407, Lippincott Williams & Wilkins (Feb. 15, 2006).
Lovitch, S.B., et al., "Amino-Terminal Flanking Residues Determine the Conformation of a Peptide-Class II MHC Complex," Journal of Immunology (Baltimore, Md. : 1950), 176(5):2958-2968, American Association of Immunologists, United States (Mar. 1, 2006).
Mach, B., et al., "Regulation of MHC Class II Genes: Lessons From a Disease," Annual Review of Immunology, 14:301-331, Annual Reviews Inc., c1983, United States (1996).
Maeda, M., et al., "CD1d-independent NKT Cells in Beta 2-microglobulin-deficient Mice Have Hybrid Phenotype and Function of Nk and T Cells," Journal of Immunology (Baltimore, Md. : 1950), 172(10):6115-6122, American Association of Immunologists, United States (May 15, 2004).
Maekawa, A., et al., "Evidence for a Domain-Swapped CD4 Dimer as the Coreceptor for Binding to Class II MHC," Journal of Immunology (Baltimore, Md. : 1950), 176(11):6873-6878, American Association of Immunologists (Jun. 1, 2006).
Markovicplese, S., et al., "T Cell Recognition of Immunodominant and Cryptic Proteolipid Protein Epitopes in Humans," Journal of Immunology (Baltimore, Md. : 1950), 155(2):982-992, American Association of Immunologists (Jul. 15, 1995).
Marti, M., et al., "Conformationally Correct Expression of Membrane-anchored Toxoplasma Gondii SAG1 in the Primitive Protozoan Giardia Duodenalis," Infection and Immunity, 70(2):1014-1016, American Society For Microbiology, United States (Feb. 2002).
Massilamany, C., et al., "Detection of Autoreactive CD4 T Cells Using Major Histocompatibility Complex Class II Dextramers," BMC Immunology, 12:40, BioMed Central, England (Jul. 2011).
Matsuda, J.L., et al., "CD1d-restricted INKT Cells, the 'Swiss-Army Knife' of the Immune System," Current Opinion in Immunology, 20(3):358-368, Elsevier, England (Jun. 2008).
Matthias, L.J., et al., "Disulfide Exchange in Domain 2 of CD4 is Required for Entry of HIV-1," Nature Immunology, 3(8):727-732, Nature America Inc. c2000, United States (Aug. 2002).
Maynard, C.L., et al., "Regulatory T Cells Expressing Interleukin 10 Develop From Foxp3+ and Foxp3− Precursor Cells in the Absence of Interleukin 10," Nature Immunology, 8(9):931-941, Nature America Inc. c2000, United States (Sep. 2007).
MedlinePlus Medical Dictionary (Merriam Webster, Inc., 2017).
Merkler, D., et al., "Myelin Oligodendrocyte Glycoprotein-induced Experimental Autoimmune Encephalomyelitis in the Common Marmoset Reflects the Immunopathology of Pattern II Multiple Sclerosis Lesions," Multiple Sclerosis (Houndmills, Basingstoke, England), 12(4):369-374, SAGE Publications, England (Aug. 2006).
Moldovan, M.C., et al., "CD4 Dimers Constitute the Functional Component Required for T Cell Activation," Journal of Immunology (Baltimore, Md. : 1950), 169(11):6261 -6268, American Association of Immunologists (Dec. 1, 2002).
Nepom, G.T., "MHC Class II Tetramers," The Journal of Immunology, 188(6):2477-2482, American Association of Immunologists, United States (Mar. 2012).

NetMHCIIpan Server—Prediction Results dated Sep. 26, 2018, 1 page.
Nielsen, M., et al., "Quantitative Predictions of Peptide Binding to Any HLA-DR Molecule of Known Sequence: NetMHCIIpan," PLoS computational biology, 4(7):e1000107, Public Library of Science, [2005], United States (Jul. 4, 2008).
Non-Final Office Action dated Apr. 1, 2014, in U.S. Appl. No. 12/735,740, 371 ©, Saint-Remy, J.M., filed Aug. 13, 2010, 12 Pages.
Non-Final Office Action dated Apr. 20, 2015, in U.S. Appl. No. 12/377,048, 371 ©, Saint-Remy, J.M., filed Feb. 10, 2009, 15 Pages.
Non-Final Office Action dated Aug. 14, 2019, in U.S. Appl. No. 15/151,868, Saint-Remy, J.M., et al., filed May 11, 2016, 15 Pages.
Non-Final Office Action dated Aug. 17, 2016, in U.S. Appl. No. 14/589,134, Saint-Remy, J.M., filed Jan. 5, 2015, 11 Pages.
Non-Final Office Action dated Aug. 24, 2017, in U.S. Appl. No. 14/450,722, Saint-Remy, J.M., filed Aug. 4, 2014, 9 Pages.
Non-Final Office Action dated Dec. 1, 2017, in U.S. Appl. No. 14/980,932, Saint-Remy, J.M., filed Dec. 28, 2015.
Non-Final Office Action dated Feb. 20, 2018, in U.S. Appl. No. 14/976,259, Saint-Remy, J.M., filed Dec. 21, 2015, 17 Pages.
Non-Final Office Action dated Feb. 23, 2017, in U.S. Appl. No. 14/375,324, Saint-Remy, J.M., filed Jul. 29, 2014, 12 Pages.
Non-Final Office Action dated Jan. 11, 2016, in U.S. Appl. No. 12/735,739, Saint-Remy, J.M., filed Aug. 13, 2010, 11 Pages.
Non-Final Office Action dated Jan. 14, 2019, in U.S. Appl. No. 14/450,722, Saint-Remy, J.M., filed Aug. 4, 2014, 8 Pages.
Non-Final Office Action dated Jan. 18, 2013, in U.S. Appl. No. 12/735,742, Saint-Remy, J.M., filed Aug. 13, 2010, 27 Pages.
Non-Final Office Action dated Jan. 20, 2012, in U.S. Appl. No. 12/735,754, Saint-Remy, J.M., filed Aug. 13, 2010, 16 Pages.
Non-Final Office Action dated Jan. 22, 2013, in U.S. Appl. No. 12/735,740, Saint-Remy, J.M., filed Aug. 13, 2010, 21 Pages.
Non-Final Office Action dated Jan. 9, 2014, in U.S. Appl. No. 12/735,744, Saint-Remy, J.M., filed Aug. 13, 2010, 10 Pages.
Non-Final Office Action dated Jul. 11, 2013, in U.S. Appl. No. 12/735,739, Saint-Remy, J.M., filed Aug. 13, 2010, 8 Pages.
Non-Final Office Action dated Jul. 14, 2017, in U.S. Appl. No. 14/589,134, Saint-Remy, J.M., filed Jan. 5, 2015, 16 Pages.
Non-Final Office Action dated Jul. 24, 2014, in U.S. Appl. No. 12/735,754, Saint-Remy, J.M., filed Aug. 13, 2010, 13 Pages.
Non-Final Office Action dated Jun. 17, 2016, in U.S. Appl. No. 13/988,925, Saint-Remy, J.M., filed Jun. 6, 2013, 9 Pages.
Non-Final Office Action dated Jun. 22, 2020, in U.S. Appl. No. 14/450,722, Saint-Remy, J.M., filed Aug. 4, 2014, 9 Pages.
Non-Final Office Action dated Jun. 25, 2018, in U.S. Appl. No. 14/375,324, Saint-Remy, J.M., filed Jul. 29, 2014, 10 Pages.
Non-Final Office Action dated Jun. 8, 2018, in U.S. Appl. No. 15/151,868, Saint-Remy, J.M., et al., filed May 11, 2016, 12 Pages.
Non-Final Office Action dated May 17, 2019, in U.S. Appl. No. 14/976,259, Saint-Remy, J.M., filed Dec. 21, 2015, 15 Pages.
Non-Final Office Action dated Nov. 25, 2014, in U.S. Appl. No. 12/735,744, Saint-Remy, J.M., filed Aug. 13, 2010, 10 Pages.
Non-Final Office Action dated Nov. 9, 2017, in U.S. Appl. No. 13/988,925, Saint-Remy, J.M., filed Jun. 6, 2013, 8 Pages.
Non-Final Office Action dated Oct. 2, 2019, in U.S. Appl. No. 14/375,324, Saint-Remy, J.M., filed Jul. 29, 2014, 10 Pages.
Non-Final Office Action dated Oct. 2, 2018, in U.S. Appl. No. 15/388,398, Saint-Remy, J.M., filed Dec. 22, 2016, 17 Pages.
Non-Final Office Action dated Oct. 5, 2018, in U.S. Appl. No. 14/589,134, Saint-Remy, J.M., filed Jan. 5, 2015, 6 Pages.
Non-Final Office Action dated Sep. 11, 2018, in U.S. Appl. No. 14/980,932, Saint-Remy, J.M., filed Dec. 28, 2015.
Non-Final Office Action dated Sep. 18, 2018, in U.S. Appl. No. 15/516,045, 371 ©, Saint-Remy, J.M., et al., filed Mar. 31, 2017, 7 Pages.
Non-Final Office Action dated Sep. 7, 2018, in U.S. Appl. No. 14/894,221, Saint-Remy, J.M., et al., filed Nov. 25, 2015, 7 Pages.
Notice of Allowance dated Apr. 15, 2019, in U.S. Appl. No. 14/894,221, 371 ©, Saint-Remy, J.M., et al., filed Nov. 25, 2015, 8 Pages.
Notice of Allowance dated Apr. 3, 2019, in U.S. Appl. No. 14/980,932, Saint-Remy, J.M., filed Dec. 28, 2015.

(56) References Cited

OTHER PUBLICATIONS

Notice of Allowance dated Dec. 2, 2019, in U.S. Appl. No. 14/980,932, Saint-Remy, J.M., filed Dec. 28, 2015, 7 pages.
Notice of Allowance dated Feb. 21, 2019, in U.S. Appl. No. 14/589,134, Saint-Remy, J.M., filed Jan. 5, 2015, 10 Pages.
Notice of Allowance dated Jan. 30, 2015, in U.S. Appl. No. 12/735,754, Saint-Remy, J.M., filed Aug. 13, 2010, 9 Pages.
Notice of Allowance dated Mar. 26, 2018, in U.S. Appl. No. 13/988,925, Saint-Remy, J.M., filed Jun. 6, 2013, 8 Pages.
Notice of Allowance dated Mar. 27, 2020, in U.S. Appl. No. 15/151,868, Saint-Remy, J.M., et al., filed May 11, 2016, 2015, 9 Pages.
Notice of Allowance dated Mar. 3, 2015, in U.S. Appl. No. 12/735,740, 371 ©, Saint-Remy, J.M., filed Aug. 13, 2010, 2 Pages.
Notice of Allowance dated Nov. 26, 2019, in U.S. Appl. No. 14/589,134, Saint-Remy, J.M., filed Jan. 5, 2015, 9 Pages.
Notice of Allowance dated Oct. 2, 2014, in U.S. Appl. No. 12/735,740, 371 ©, Saint-Remy, J.M., filed Aug. 13, 2010, 7 Pages.
Notice of Allowance dated Sep. 22, 2015, in U.S. Appl. No. 12/377,048, 371 ©, Saint-Remy, J.M., filed Feb. 10, 2009, 9 Pages.
Notice of Allowance dated Sep. 27, 2019, in U.S. Appl. No. 15/388,398, Saint-Remy, J.M., filed Dec. 22, 2016, 11 Pages.
Notice of Allowance dated Sep. 28, 2015, in U.S. Appl. No. 12/735,744, 371 ©, Saint-Remy, J.M., filed Aug. 13, 2010, 7 Pages.
Notice of Allowance dated Sep. 7, 2017, in U.S. Appl. No. 14/686,855, Saint-Remy, J.M., filed Apr. 15, 2015, 11 Pages.
Ochoa-Garay, J., et al., "The Ability of Peptides to Induce Cytotoxic T Cells in Vitro Does Not Strongly Correlate With Their Affinity for the H-2ld Molecule: Implications for Vaccine Design and Immunotherapy," Molecular Immunology, 34(3):273-281, Pergamon Press, England (Feb. 1997).
Okubo, M., et al., "Analysis of HLA-DRB1*0901-Binding HPV-16 E7 Helper T Cell Epitope.," The Journal of Obstetrics and Gynaecology Research, 30(2):120-129, Wiley, Australia (Apr. 2004).
Oliveira, M.A., et al., "Insights into the Specificity of Thioredoxin Reductase-Thioredoxin Interactions. A Structural and Functional Investigation of the Yeast Thioredoxin System," Biochemistry, 49(15):3317-3326, American Chemical Society, United States (Apr. 2010).
O'Sullivan, D.M., et al., "MHC HLA-DR Gamma Chain, Partial [*Homo sapiens*]," GenBank AAA58655.1, 1994, p. 1.
Papanastasiou, P., et al., "Primary Structure and Biochemical Properties of a Variant-specific Surface Protein of Giardia.," Molecular and Biochemical Parasitology, 86(1):13-27, Elsevier/North-Holland Biomedical Press, Netherlands (May 1997).
Park, B., et al., "Redox Regulation Facilitates Optimal Peptide Selection by MHC Class I During Antigen Processing," Cell, 127(2):369-382, Cell Press, United States (Oct. 2006).
Parrino, J., et al., "Prevention of Immune Cell Apoptosis as Potential Therapeutic Strategy for Severe Infections," Emerging Infectious Diseases 13(2):191-198, National Center for Infectious Diseases, United States (Feb. 2007).
Peterson, R.A., "Regulatory T-cells: Diverse Phenotypes Integral to Immune Homeostasis and Suppression," Toxicologic Pathology, 40(2):186-204, Sage Publications, United States (2012).
Pillai, A.B., "Host NKT Cells Can Prevent Graft-versus-host Disease and Permit Graft Antitumor Activity After Bone Marrow Transplantation," Journal of Immunology , 178(10):6242-6251, American Association of Immunologists, United States (2007).
Pira, L.G., et al., "High Throughput T Epitope Mapping and Vaccine Development," Journal of Biomedicine & Biotechnology, 2010:12, Hindawi Pub. Corp, United States (Jun. 15, 2010).
Qin, W., et al., "Fusion Protein of CDR Mimetic Peptide With Fc Inhibit TNF-alpha Induced Cytotoxicity.," Molecular Immunology, 43(6):660-666, Pergamon Press, England (Feb. 2006).
Quintana, F, J., et al., "Epitope Spreading as an Early Pathogenic Event in Pediatric Multiple Sclerosis," Neurology, 83(24):2219-2226, Lippincott Williams & Wilkins, United States (Dec. 2014).

Racaniello, V., "How Many Viruses on Earth?," Virology Blog, 2013, 3 pages. Retrieved from Internet:[URL:http://www.virology.ws/2013/09/06/how-many-viruses-on-earth/].
Rammensee, H.G., et al., "MHC Ligands and Peptide Motifs," in Molecular Biology Intelligence Unit, p. 317, Springer, New York & Austin, Texas, USA (1997).
Reznik, S.I., et al., "Indirect Allorecognition of Mismatched Donor Hla Class Ii Peptides in Lung Transplant Recipients With Bronchiolitis Obliterans Syndrome," American Journal of Transplantation, 1(3):228-235, Wiley-Blackwell, United States (Sep. 2001).
Robinson, A.P., et al., "Vaccine Protocol," in Methods in Molecular Medicine, Humana Press, Totowa, NJ, Ed. Andrew Robinson, Michael J. Hudson and Martin P. Cranage, pp. 121-123 (2003).
Roep, B.O., et al., "The Problems and Promises of Research Into Human Immunology and Autoimmune Disease," Nature Medicine, 18(1):48-53, Nature Publishing Company, United States (Jan. 2012 ).
Roopenian, D., et al., "The Immunogenomics of Minor Histocompatibility Antigens.," Immunological Reviews, 190:86-94, Blackwell, England (Dec. 2002).
Roper, R.L., et al., "SARS Vaccines: Where Are We?," Expert Review of Vaccines, 8(7):887-898, Taylor & Francis, England (Jul. 2009).
Saez-Borderias, A., et al., "Expression and Function of NKG2D in CD4+ T cells Specific for Human Cytomegalovirus," European Journal of Immunology, 36(12):3198-3206, Wiley-VCH, Germany (Dec. 2006).
Santin, A, D, et al., "Human Papillomavirus Type 16 and 18 E7-Pulsed Dendritic Cell Vaccination of Stage IB or IIA Cervical Cancer Patients: A Phase I Escalating-Dose Trial," Journal of Virology, 82(4):1968-1979, American Society for Microbiology, United States (Feb. 2008).
Savoldo, B, et al., "Generation of EBV-specific CD4+ Cytotoxic T cells from Virus Naive Individuals," Journal of Immunology, 168(2):909-918, American Association of Immunologists, United States (Jan. 2002).
Schrieber, T.H., et al., "Tumor Immunogenicity and Responsiveness to Cancer Vaccine Therapy: the State of the Art," Seminars in Immunology, 22(3):105-112, Academic Press, Academic Press (Jun. 2010).
Schultz, E.S., et al., "A MAGE-A3 Peptide Presented by HLA-DP4 Is Recognized on Tumor Cells by CD4+ Cytolytic T Lymphocyte," Cancer Research, 60(22):6272-6275, American Association for Cancer Research, United States (Nov. 2000).
Schwartz, R.H., et al., "The T Lymphocyte Response to Cytochrome c. V. Determination of the Minimal Peptide Size Required for Stimulation of T Cell Clones and Assessment of the Contribution of Each Residue Beyond This Size to Antigenic Potency," Journal of Immunology, 135(4):2598-2608, American Association of Immunologists, United States (Oct. 1985).
Sette, A and Fikes, J., "Epitope-based Vaccines: an Update on Epitope Identification, Vaccine Design and Delivery," Current Opinion in Immunology, 15(4):461-470, Elsevier, England (Aug. 2003).
Sette, A and Sidney, J., "HLA Supertypes and Supermotifs: a Functional Perspective on HLA Polymorphism," Current Opinion in Immunology, 10(4):478-482, Elsevier, England (Aug. 1998).
Shi, J and Bhattacharyya, M. K., "A Novel Plasma Membrane-bound Thioredoxin From Soybean," Plant Molecular Biology, 32(4):653-662, Kluwer Academic, Netherlands (Nov. 1996).
Skonier, J., et al., "Human Transforming Growth Factor-beta Induced Gene Product (BIGH3) mRNA, Complete cds," GenBank M77349. 1, Jan. 14, 1995, 3 pages.
Stenstrom, M., et al., "Natural Killer T-cell Populations in C57BL/6 and NK1.1 Congenic BALB.NK Mice—a Novel Thymic Subset defined in BALB.NK Mice.," Immunology, 114(3):336-345, Blackwell Scientific Publications, England (Mar. 2005).
Straub, R. B., et al., "Allelic Variation in GAD1 (GAD67) is Associated With Schizophrenia and Influences Cortical Function and Gene Expression," Molecular Psychiatry, 12(9):854-869, Nature Publishing Group Specialist Journals, England (Sep. 2007).
Sundar, S.K and Menezes, J., "Generation of Epstein-bar Virus Antigen-specific Suppressor T Cells in Vitro," International Journal of Cancer, 35(3):351-357, Wiley-Liss, United States (Mar. 1985).

(56) References Cited

OTHER PUBLICATIONS

Taylor, A., et al., "T Regulatory Cells and Allergy," Microbes and Infection, 7(7-8):1049-1055, Elsevier, France (Jun. 2005).
Texier, C., et al., "On the Diversity and Heterogeneity of H-2(D)-restricted Determinants and T Cell Epitopes From the Major Bee Venom Allergen," International Immunology, 11(8):1313-1326, Oxford, England (Aug. 1999).
Thomson, S.A., et al., "Targeting a Polyepitope Protein Incorporating Multiple Class 11-restricted Viral Epitopes to the Secretory/endocytic Pathway Facilitates Immune Recognition by CD4+ Cytotoxic T Lymphocytes: a Novel Approach to Vaccine Design," Journal of Virology, 72(3):2246-2252, American Society For Microbiology, United States (Mar. 1998).
Tindle, R.W., et al., "A "Public" T-helper Epitope of the E7 Transforming Protein of Human Papillomavirus 16 Provides Cognate Help for Several E7 B-cell Epitopes From Cervical Cancer-associated Human Papillomavirus Genotypes," Proceedings of the National Academy of Sciences of the United States of America, 88(13):5887-5891, National Academy of Sciences, United States (Jul. 1991).
Tisch, R and McDevitt, H.O., "Antigen-specific Immunotherapy: is It a Real Possibility to Combat T-cell-mediated Autoimmunity?," Proceedings of the National Academy of Sciences of the United States of America, 91(2):437-438, National Academy of Sciences, United States (Jan. 1994).
Toyokawa, H., et al., "Relative Contribution of Direct and Indirect Allorecognition in Developing Tolerance After Liver Transplantation," Liver Transplantation, 14(3):346-357, Wiley, United States (Mar. 2008).
Tsuji, N.M., et al, "Antigen-specific, CD4+CD25+ Regulatory T Cell Clones Induced in Peyer's Patches," International Immunology, 15(4):525-534, Oxford, England (Apr. 2003).
UniProt 015523.2, 2017, pp. 1-7.
UniProt P01906.2, 2017, p. 1-6.
Vignali, D.A. and Strominger, J.L., "Amino Acid Residues That Flank Core Peptide Epitopes and the Extracellular Domains of CD4 Modulate Differential Signaling Through the T Cell Receptor," The Journal of Experimental Medicine, 179(6):1945-1956, Rockefeller University Press, United States (Jun. 1994).
ViralZone, 2017.
Voo, K.S., et al., "Functional Characterization of Ebv-encoded Nuclear Antigen 1-specific CD4+ Helper and Regulatory T Cells Elicited by in Vitro Peptide Stimulation," Cancer Research, 65(4):1577-1586, American Association for Cancer Research, United States (Feb. 2006).
Wang et al., "Generation and characterization of HLA-A*2.1 restricted and Prostein 31-39 specific NKT cell lines," Acta Academiae Medicine Militaris Tertiae, 28(16):1652-1655 (2006) (English language translation provided) (11 pages).
Wang, R.F., "Immune Suppression by Tumor-specific CD4+ Regulatory T-cells in Cancer," Seminars in Cancer Biology, 16(1):73-79, Academic Press, England (Feb. 2005).
Weissert, R., et al., "MHC Class Ii-regulated Central Nervous System Autoaggression and T Cell Responses in Peripheral Lymphoid Tissues Are Dissociated in Myelin Oligodendrocyte Glycoprotein-induced Experimental Autoimmune Encephalomyelitis.," Journal of Immunology, 166(12):7588-7599, American Association of Immunologists, United States (Jun. 2001).
Wekerle, H., et al., "Autoimmunity's Next Top Models," Nature Medicine, 18(1):66-70, Nature Publishing Company, United States (Jan. 2012).
Wiker, H.G., et al., "Cloning, Expression and Significance of MPT53 for Identification of Secreted Proteins of *Mycobacterium tuberculosis*," Microbial Pathogenesis, 26(4):207-219, Academic Press, England (Apr. 1999).
Witmer, C. and Young, G., "Factor VIII Inhibitors in Hemophilia a: Rationale and Latest Evidence," Therapeutic Advances in Hematology, 4(1):59-72, Sage, England (Feb. 2013).
Wobus, A.M and Boheler, K.R., "Embryonic Stem Cells: Prospects for Developmental Biology and Cell Therapy," Physiological Reviews, 85(2):635-678, American Physiological Society, United States (Apr. 2005).
Wood, K.J and Sakaguchi, S., "Regulatory T Cells in Transplantation Tolerance," Nature Reviews. Immunology, 3(3):199-210, Nature Pub. Group, England (Mar. 2003).
Wooldridge, L., et al., "Tricks With Tetramers: How to Get the Most From Multimeric Peptide-MHC," Immunology, 126(2):147-164, Blackwell Scientific Publications, England (Feb. 2009).
Written Description Training Materials, Revision 1, Mar. 25, 2008, United States Patent and Trademark Office.
Written Opinion for International Application No. PCT/EP2007/007165, European Patent Office, Netherlands, dated Jan. 17, 2008, 8 Pages.
Written Opinion for International Application No. PCT/EP2009/051803, European Patent Office, Netherlands, dated Aug. 11, 2009, 7 Pages.
Written Opinion for International Application No. PCT/EP2009/051804, European Patent Office, Netherlands, dated Aug. 11, 2009, 8 Pages.
Written Opinion for International Application No. PCT/EP2009/051807, European Patent Office, Netherlands, dated Jul. 13, 2009, 5 Pages.
Written Opinion for International Application No. PCT/EP2009/051808, European Patent Office, Netherlands, dated Feb. 18, 2010, 7 Pages.
Written Opinion for International Application No. PCT/EP2014/060994, European Patent Office, Netherlands, dated Jun. 1, 2015, 7 pages.
Written Opinion for International Application No. PCT/EP2014/060994, European Patent Office, Netherlands, dated Sep. 18, 2014, 6 pages.
Written Opinion of the International Preliminary Examining Authority for International Application No. PCT/BE2013/000006, European Patent Office, Germany, dated Feb. 14, 2014, 15 Pages.
Written Opinion of the International Searching Authority for International Application No. PCT/BE2008/000010, European Patent Office, Germany, dated Jul. 2, 2008, 8 Pages.
Written Opinion of the International Searching Authority for International Application No. PCT/BE2013/000006, European Patent Office, Germany, dated Jul. 1, 2013, 10 Pages.
Written Opinion of the International Searching Authority for International Application No. PCT/EP2009/051806, European Patent Office, Netherlands, dated Aug. 11, 2009, 7 Pages.
Wu, T.C., et al., "Engineering an Intracellular Pathway for Major Histocompatibility Complex Class II Presentation of Antigens," Proceedings of the National Academy of Sciences of the United States of America, 92(25):11671-11675, National Academy of Sciences, United States (Dec. 1995).
Zeng, Z., et al., "Crystal Structure of Mouse CD1: an MHC-like Fold With a Large Hydrophobic Binding Groove," Science, 277(5324):339-345, American Association for the Advancement of Science, United States (Jul. 1997).
Zhang, D., et al., "Preclinical Experimental Models of Drug Metabolism and Disposition in Drug Discovery and Development," Acta Pharmaceutica Sinica B, 2(6):549-561, (Dec. 2012).
Zhang, Y., et al., "A Mage-3 Peptide Presented by HLA-DR1 to CD4+ T Cells That Were Isolated From a Melanoma Patient Vaccinated With a Mage-3 Protein," Journal of Immunology, 171(1):219-225, American Association of Immunologists, United States (Jul. 2003).
Zhao, D.M., et al., "Activated CD4+CD25+ T Cells Selectively Kill B Lymphocytes," Blood, 107(10):3925-3932, American Society of Hematology, United States (May 2006).
Non-Final Office Action dated Sep. 7, 2016, in U.S. Appl. No. 14/686,855, Saint-Remy, J.M., filed Apr. 15, 2015, 9 Pages.
U.S. Appl. No. 17/934,607, filed Sep. 23, 2022, Vander Elst et al., related application.
U.S. Appl. No. 17/611,290, filed Nov. 15, 2021, Erak, related application.
U.S. Appl. No. 17/923,108, filed Nov. 3, 2022, Saint-Remy et al., related application.

(56) References Cited

OTHER PUBLICATIONS

U.S. Appl. No. 17/923,117, filed Nov. 3, 2022, Erak, related application.
U.S. Appl. No. 17/923,215, filed Nov. 3, 2022, Saint-Remy et al., related application.
U.S. Appl. No. 17/923,217, filed Nov. 3, 2022, Erak, related application.

* cited by examiner

CFSE

Anti-cleaved caspase-3 FITC

| Lung CD4 cells | Treg | Control T | No T cells |
|---|---|---|---|
| % CD4 | 91,9 +/- 0,815 | 27,4 +/- 1,503 | 25,3 +/- 1,428 |
| % Vβ8.1+ (in CD4) | 92,5 +/- 1,087 | 26,5 +/- 1,544 | 19,2 +/- 1,138 |

SEQUENCE LISTING

<160> NUMBER OF SEQ ID NOS: 49

<210> SEQ ID NO 1
<211> LENGTH: 10
<212> TYPE: PRT
<213> ORGANISM: artificial sequence
<220> FEATURE:
<223> OTHER INFORMATION: Der p 2 allergen epitope

<400> SEQUENCE: 1

Glu Pro Cys Ile Ile His Arg Gly Lys Pro
1               5                   10

<210> SEQ ID NO 2
<211> LENGTH: 15
<212> TYPE: PRT
<213> ORGANISM: artificial sequence
<220> FEATURE:
<223> OTHER INFORMATION: the p21-35 peptide of Der p 2 allergen

<400> SEQUENCE: 2

Cys His Gly Ser Glu Pro Cys Ile Ile His Arg Gly Lys Pro Phe
1               5                   10                  15

<210> SEQ ID NO 3
<211> LENGTH: 4
<212> TYPE: PRT
<213> ORGANISM: artificial sequence
<220> FEATURE:
<223> OTHER INFORMATION: reducing tetrapeptide

<400> SEQUENCE: 3

Cys His Gly Ser
1

<210> SEQ ID NO 4
<211> LENGTH: 66
<212> TYPE: PRT
<213> ORGANISM: artificial sequence
<220> FEATURE:
<223> OTHER INFORMATION: recombinant tetramer of p21-35 of Der p 2
      allergen

<400> SEQUENCE: 4

Cys His Gly Ser Glu Pro Cys Ile Ile His Arg Gly Lys Pro Phe Gly
1               5                   10                  15

Gly Cys His Gly Ser Glu Pro Cys Ile Ile His Arg Gly Lys Pro Phe
            20                  25                  30

Gly Gly Cys His Gly Ser Glu Pro Cys Ile Ile His Arg Gly Lys Pro
        35                  40                  45

Phe Gly Gly Cys His Gly Ser Glu Pro Cys Ile Ile His Arg Gly Lys
    50                  55                  60

Pro Phe
65

<210> SEQ ID NO 5
<211> LENGTH: 15
<212> TYPE: PRT
<213> ORGANISM: artificial sequence
<220> FEATURE:
<223> OTHER INFORMATION: dominant T cell epitope of Der p 1 allergen

<400> SEQUENCE: 5

Ser Asn Tyr Cys Gln Ile Tyr Pro Pro Asn Ala Asn Lys Ile Arg
1               5                   10                  15

<210> SEQ ID NO 6
<211> LENGTH: 4
<212> TYPE: PRT
<213> ORGANISM: artificial sequence
<220> FEATURE:
<223> OTHER INFORMATION: reducing tetrapeptide

<400> SEQUENCE: 6

Cys Gly Phe Ser
1

<210> SEQ ID NO 7
<211> LENGTH: 19
<212> TYPE: PRT
<213> ORGANISM: artificial sequence
<220> FEATURE:
<223> OTHER INFORMATION: glutaredoxin-like consensus sequence and
      dominant T cell epitope of the Der p 1 allergen

<400> SEQUENCE: 7

Cys Gly Phe Ser Ser Asn Tyr Cys Gln Ile Tyr Pro Pro Asn Ala Asn
1               5                   10                  15

Lys Ile Arg

<210> SEQ ID NO 8
<211> LENGTH: 9
<212> TYPE: PRT
<213> ORGANISM: artificial sequence
<220> FEATURE:
<223> OTHER INFORMATION: linker sequence

<400> SEQUENCE: 8

Ser Gly Gly Ser Gly Gly Ser Gly Gly
1               5

<210> SEQ ID NO 9
<211> LENGTH: 41
<212> TYPE: PRT
<213> ORGANISM: artificial sequence
<220> FEATURE:
<223> OTHER INFORMATION: transmembrane domain and truncated cytosolic
      tail of gp75 protein

<400> SEQUENCE: 9

Ile Ile Thr Ile Ala Val Val Ala Ala Leu Leu Leu Val Ala Ala Ile
1               5                   10                  15

Phe Gly Val Ala Ser Cys Leu Ile Arg Ser Arg Ser Thr Lys Asn Glu
                20                  25                  30

Ala Asn Gln Pro Leu Leu Thr Asp Ser
        35                  40

<210> SEQ ID NO 10
<211> LENGTH: 68
<212> TYPE: PRT
<213> ORGANISM: artificial sequence
<220> FEATURE:
<223> OTHER INFORMATION: targeting sequence, linker, thioredoxin
      consensus sequence and dominant T cell epitope of Der p 1 allergen

<400> SEQUENCE: 10

Cys Gly Phe Ser Ser Asn Tyr Cys Gln Ile Tyr Pro Pro Asn Ala Asn
1               5                   10                  15

Lys Ile Arg Ser Gly Gly Ser Gly Gly Ser Gly Gly Ile Ile Thr Ile
                20                  25                  30

```
Ala Val Val Ala Ala Leu Leu Leu Val Ala Ala Ile Phe Gly Val Ala
        35                  40                  45

Ser Cys Leu Ile Arg Ser Arg Ser Thr Lys Asn Glu Ala Asn Gln Pro
50                      55                  60

Leu Leu Thr Asp
65

<210> SEQ ID NO 11
<211> LENGTH: 64
<212> TYPE: PRT
<213> ORGANISM: artificial sequence
<220> FEATURE:
<223> OTHER INFORMATION: targeting sequence, linker  and dominant T cell
      epitope of Der p 1 allergen

<400> SEQUENCE: 11

Ser Asn Tyr Cys Gln Ile Tyr Pro Pro Asn Ala Asn Lys Ile Arg Ser
1               5                   10                  15

Gly Gly Ser Gly Gly Ser Gly Gly Ile Ile Thr Ile Ala Val Val Ala
            20                  25                  30

Ala Leu Leu Val Ala Ala Ile Phe Gly Val Ala Ser Cys Leu Ile
        35                  40                  45

Arg Ser Arg Ser Thr Lys Asn Glu Ala Asn Gln Pro Leu Leu Thr Asp
    50                  55                  60

<210> SEQ ID NO 12
<211> LENGTH: 16
<212> TYPE: PRT
<213> ORGANISM: artificial sequence
<220> FEATURE:
<223> OTHER INFORMATION: amino acid residues 37-52 of MOG (Myelin
      Oligodendrocyte Glycoprotein) protein

<400> SEQUENCE: 12

Val Gly Trp Tyr Arg Ser Pro Phe Ser Arg Val Val His Leu Tyr Arg
1               5                   10                  15

<210> SEQ ID NO 13
<211> LENGTH: 4
<212> TYPE: PRT
<213> ORGANISM: artificial sequence
<220> FEATURE:
<223> OTHER INFORMATION: reducing tetrapeptide

<400> SEQUENCE: 13

Cys Gly Pro Ser
1

<210> SEQ ID NO 14
<211> LENGTH: 17
<212> TYPE: PRT
<213> ORGANISM: artificial sequence
<220> FEATURE:
<223> OTHER INFORMATION: modified version of amino acid residues 37-52
      of MOG protein (Myelin Oligodendrocyte Glycoprotein), wherein 3 N
      terminal amino acids are replaced by CGPS

<400> SEQUENCE: 14

Cys Gly Pro Ser Tyr Arg Ser Pro Phe Ser Arg Val Val His Leu Tyr
1               5                   10                  15

Arg

<210> SEQ ID NO 15
```

```
<211> LENGTH: 45
<212> TYPE: PRT
<213> ORGANISM: artificial sequence
<220> FEATURE:
<223> OTHER INFORMATION: transmembrane domain and cytosolic tail of
      HLA-DM protein

<400> SEQUENCE: 15

Val Ser Val Ser Ala Val Thr Leu Gly Leu Gly Leu Ile Ile Phe Ser
1               5                   10                  15

Leu Gly Val Ile Ser Trp Arg Arg Ala Gly His Ser Ser Tyr Thr Pro
            20                  25                  30

Leu Pro Gly Ser Asn Tyr Ser Glu Gly Trp His Ile Ser
        35                  40                  45

<210> SEQ ID NO 16
<211> LENGTH: 71
<212> TYPE: PRT
<213> ORGANISM: artificial sequence
<220> FEATURE:
<223> OTHER INFORMATION: transmembrane domain and cytosolic tail of
      HLA-DM protein, linker and modified MOG (Myelin Oligodendrocyte
      Glycoprotein) peptide

<400> SEQUENCE: 16

Val Ser Val Ser Ala Val Thr Leu Gly Leu Gly Leu Ile Ile Phe Ser
1               5                   10                  15

Leu Gly Val Ile Ser Trp Arg Arg Ala Gly His Ser Ser Tyr Thr Pro
            20                  25                  30

Leu Pro Gly Ser Asn Tyr Ser Glu Gly Trp His Ile Ser Ser Gly Gly
        35                  40                  45

Ser Gly Gly Ser Gly Gly Cys Gly Pro Ser Tyr Arg Ser Pro Phe Ser
    50                  55                  60

Arg Val Val His Leu Tyr Arg
65                  70

<210> SEQ ID NO 17
<211> LENGTH: 67
<212> TYPE: PRT
<213> ORGANISM: artificial sequence
<220> FEATURE:
<223> OTHER INFORMATION: transmembrane domain and cytosolic tail of
      HLA-DM protein, linker and unmodified MOG (Myelin Oligodendrocyte
      Glycoprotein) peptide

<400> SEQUENCE: 17

Val Ser Val Ser Ala Val Thr Leu Gly Leu Gly Leu Ile Ile Phe Ser
1               5                   10                  15

Leu Gly Val Ile Ser Trp Arg Arg Ala Gly His Ser Ser Tyr Thr Pro
            20                  25                  30

Leu Pro Gly Ser Asn Tyr Ser Glu Gly Trp His Ile Ser Ser Gly Gly
        35                  40                  45

Ser Gly Gly Ser Gly Gly Tyr Arg Ser Pro Phe Ser Arg Val Val His
    50                  55                  60

Leu Tyr Arg
65

<210> SEQ ID NO 18
<211> LENGTH: 15
<212> TYPE: PRT
<213> ORGANISM: artificial sequence
<220> FEATURE:
<223> OTHER INFORMATION: amino-acids 830-844 from tetanus toxoid
```

```
<400> SEQUENCE: 18

Gln Tyr Ile Lys Ala Asn Ser Lys Phe Ile Gly Ile Thr Glu Leu
1               5                   10                  15

<210> SEQ ID NO 19
<211> LENGTH: 32
<212> TYPE: PRT
<213> ORGANISM: artificial sequence
<220> FEATURE:
<223> OTHER INFORMATION: amino-acids 830-844 from tetanus toxoid and
      p21-35 peptide of Der p 2 allergen

<400> SEQUENCE: 19

Gln Tyr Ile Lys Ala Asn Ser Lys Phe Ile Gly Ile Thr Glu Leu Gly
1               5                   10                  15

Gly Cys His Gly Ser Glu Pro Cys Ile Ile His Arg Gly Lys Pro Phe
            20                  25                  30

<210> SEQ ID NO 20
<211> LENGTH: 32
<212> TYPE: PRT
<213> ORGANISM: artificial sequence
<220> FEATURE:
<223> OTHER INFORMATION: amino-acids 830-844 from tetanus toxoid and
      modified p21-35 peptide of Der p 2 allergen

<400> SEQUENCE: 20

Gln Tyr Ile Lys Ala Asn Ser Lys Phe Ile Gly Ile Thr Glu Leu Gly
1               5                   10                  15

Gly Cys His Gly Ser Glu Pro Cys Asn Ile His Arg Gly Lys Pro Phe
            20                  25                  30

<210> SEQ ID NO 21
<211> LENGTH: 20
<212> TYPE: DNA
<213> ORGANISM: artificial sequence
<220> FEATURE:
<223> OTHER INFORMATION: Granzyme A forward primer

<400> SEQUENCE: 21
ctctggtccc cggggccatc                                              20

<210> SEQ ID NO 22
<211> LENGTH: 20
<212> TYPE: DNA
<213> ORGANISM: artificial sequence
<220> FEATURE:
<223> OTHER INFORMATION: Granzyme A reverse primer

<400> SEQUENCE: 22
tatgtagtga gccccaagaa                                              20

<210> SEQ ID NO 23
<211> LENGTH: 20
<212> TYPE: DNA
<213> ORGANISM: artificial sequence
<220> FEATURE:
<223> OTHER INFORMATION: Granzyme B forward primer

<400> SEQUENCE: 23
ctccacgtgc tttcaccaaa                                              20

<210> SEQ ID NO 24
<211> LENGTH: 21
```

<212> TYPE: DNA
<213> ORGANISM: artificial sequence
<220> FEATURE:
<223> OTHER INFORMATION: Granzyme B reverse primer

<400> SEQUENCE: 24
ggaaaatagt acagagaggc a                                    21

<210> SEQ ID NO 25
<211> LENGTH: 24
<212> TYPE: DNA
<213> ORGANISM: artificial sequence
<220> FEATURE:
<223> OTHER INFORMATION: -actin forward  primer

<400> SEQUENCE: 25
cattgtgatg gactccggag acgg                                 24

<210> SEQ ID NO 26
<211> LENGTH: 24
<212> TYPE: DNA
<213> ORGANISM: artificial sequence
<220> FEATURE:
<223> OTHER INFORMATION: -actin reverse primer

<400> SEQUENCE: 26
catctcctgc tcgaagtcta gagc                                 24

<210> SEQ ID NO 27
<211> LENGTH: 21
<212> TYPE: DNA
<213> ORGANISM: Artificial sequence
<220> FEATURE:
<223> OTHER INFORMATION: retroviral vector-specific forward primer

<400> SEQUENCE: 27
ccctttatcc agccctcact c                                    21

<210> SEQ ID NO 28
<211> LENGTH: 20
<212> TYPE: DNA
<213> ORGANISM: artificial sequence
<220> FEATURE:
<223> OTHER INFORMATION: retroviral vector-specific reverse primer

<400> SEQUENCE: 28
cctggggact ttccacaccc                                      20

<210> SEQ ID NO 29
<211> LENGTH: 15
<212> TYPE: PRT
<213> ORGANISM: artificial sequence
<220> FEATURE:
<223> OTHER INFORMATION: p21-35 peptide of Der p2 allergen mutated at
      residue 24

<400> SEQUENCE: 29

Cys His Gly Cys Glu Pro Cys Ile Ile His Arg Gly Lys Pro Phe
1               5                   10                  15

<210> SEQ ID NO 30
<211> LENGTH: 13
<212> TYPE: PRT
<213> ORGANISM: artificial sequence
<220> FEATURE:
<223> OTHER INFORMATION: thioredox motif sequence CHGC linked to  T cell
      epitope of Bovine beta-lactoglobulin (BLG)

```
<400> SEQUENCE: 30

Cys His Gly Cys Ala Gln Lys Lys Ile Ile Ala Glu Lys
1               5                   10

<210> SEQ ID NO 31
<211> LENGTH: 4
<212> TYPE: PRT
<213> ORGANISM: artificial sequence
<220> FEATURE:
<223> OTHER INFORMATION: thioredox motif sequence CHGC

<400> SEQUENCE: 31

Cys His Gly Cys
1

<210> SEQ ID NO 32
<211> LENGTH: 17
<212> TYPE: PRT
<213> ORGANISM: artificial sequence
<220> FEATURE:
<223> OTHER INFORMATION: reducing motif fused to MOG (Myelin
      Oligodendrocyte Glycoprotein) peptide

<400> SEQUENCE: 32

Cys His Gly Ser Tyr Arg Ser Pro Phe Ser Arg Val Val His Leu Tyr
1               5                   10                  15

Arg

<210> SEQ ID NO 33
<211> LENGTH: 13
<212> TYPE: PRT
<213> ORGANISM: Artificial sequence
<220> FEATURE:
<223> OTHER INFORMATION: MOG (Myelin Oligodendrocyte Glycoprotein)
      peptide

<400> SEQUENCE: 33

Tyr Arg Ser Pro Phe Ser Arg Val Val His Leu Tyr Arg
1               5                   10

<210> SEQ ID NO 34
<211> LENGTH: 20
<212> TYPE: PRT
<213> ORGANISM: artificial sequence
<220> FEATURE:
<223> OTHER INFORMATION: fragment 524-543 of glutamic acid decarboxylase
      (GAD65)

<400> SEQUENCE: 34

Ser Arg Leu Ser Lys Val Ala Pro Val Ile Lys Ala Arg Met Met Glu
1               5                   10                  15

Tyr Gly Thr Thr
            20

<210> SEQ ID NO 35
<211> LENGTH: 15
<212> TYPE: PRT
<213> ORGANISM: artificial sequence
<220> FEATURE:
<223> OTHER INFORMATION: modified fragment of glutamic acid
      decarboxylase (GAD65)

<400> SEQUENCE: 35

Cys Arg Leu Cys Lys Val Ala Pro Val Ile Lys Ala Arg Met Met
1               5                   10                  15
```

```
<210> SEQ ID NO 36
<211> LENGTH: 14
<212> TYPE: PRT
<213> ORGANISM: artificial sequence
<220> FEATURE:
<223> OTHER INFORMATION: T cell epitope of insulin and CGPC sequence

<400> SEQUENCE: 36

Glu Ala Leu Tyr Val Cys Gly Glu Arg Gly Cys Gly Pro Cys
1               5                   10

<210> SEQ ID NO 37
<211> LENGTH: 15
<212> TYPE: PRT
<213> ORGANISM: artificial sequence
<220> FEATURE:
<223> OTHER INFORMATION: T cell epitope of insulin and CGPC sequence
      with glycine linker

<400> SEQUENCE: 37

Glu Ala Leu Tyr Val Cys Gly Glu Arg Gly Gly Cys Gly Pro Cys
1               5                   10                  15

<210> SEQ ID NO 38
<211> LENGTH: 16
<212> TYPE: PRT
<213> ORGANISM: artificial sequence
<220> FEATURE:
<223> OTHER INFORMATION: T cell epitope of insulin and CGPC sequence
      with glycine linker

<400> SEQUENCE: 38

Glu Ala Leu Tyr Val Cys Gly Glu Arg Gly Gly Gly Cys Gly Pro Cys
1               5                   10                  15

<210> SEQ ID NO 39
<211> LENGTH: 17
<212> TYPE: PRT
<213> ORGANISM: artificial sequence
<220> FEATURE:
<223> OTHER INFORMATION: T cell epitope of insulin and CGPC sequence
      with glycine linker

<400> SEQUENCE: 39

Glu Ala Leu Tyr Val Cys Gly Glu Arg Gly Gly Gly Gly Cys Gly Pro
1               5                   10                  15

Cys

<210> SEQ ID NO 40
<211> LENGTH: 18
<212> TYPE: PRT
<213> ORGANISM: artificial sequence
<220> FEATURE:
<223> OTHER INFORMATION: T cell epitope of insulin and CGPC sequence
      with glycine linker

<400> SEQUENCE: 40

Glu Ala Leu Tyr Val Cys Gly Glu Arg Gly Gly Gly Gly Gly Cys Gly
1               5                   10                  15

Pro Cys

<210> SEQ ID NO 41
<211> LENGTH: 19
<212> TYPE: PRT
<213> ORGANISM: artificial sequence
```

```
<220> FEATURE:
<223> OTHER INFORMATION: fragment 540-559 of thyroperoxidase

<400> SEQUENCE: 41

Gln Gly Gln Leu Met Asn Glu Glu Leu Thr Glu Arg Leu Phe Val Leu
1               5                   10                  15

Ser Asn Val

<210> SEQ ID NO 42
<211> LENGTH: 4
<212> TYPE: PRT
<213> ORGANISM: Artificial sequence
<220> FEATURE:
<223> OTHER INFORMATION: D isomer sequence of CGPC

<400> SEQUENCE: 42

Cys Gly Pro Cys
1

<210> SEQ ID NO 43
<211> LENGTH: 13
<212> TYPE: PRT
<213> ORGANISM: artificial sequence
<220> FEATURE:
<223> OTHER INFORMATION: modified fragment of thyroperoxidase

<400> SEQUENCE: 43

Cys Gly Pro Cys Met Asn Glu Glu Leu Thr Glu Arg Leu
1               5                   10

<210> SEQ ID NO 44
<211> LENGTH: 20
<212> TYPE: PRT
<213> ORGANISM: artificial sequence
<220> FEATURE:
<223> OTHER INFORMATION: Fragment 2340-2359 of thyroglobulin

<400> SEQUENCE: 44

Gln Val Ala Ala Leu Thr Trp Val Gln Thr His Ile Arg Gly Phe Gly
1               5                   10                  15

Gly Asp Pro Arg
            20

<210> SEQ ID NO 45
<211> LENGTH: 13
<212> TYPE: PRT
<213> ORGANISM: artificial sequence
<220> FEATURE:
<223> OTHER INFORMATION: modified fragment of thyroglobulin

<400> SEQUENCE: 45

Cys Gly Pro Ser Ala Ala Leu Thr Trp Val Gln Thr His
1               5                   10

<210> SEQ ID NO 46
<211> LENGTH: 11
<212> TYPE: PRT
<213> ORGANISM: artificial sequence
<220> FEATURE:
<223> OTHER INFORMATION: fragment 144-154 of Bet v 1 (main birch pollen
      allergen)

<400> SEQUENCE: 46

Leu Arg Ala Val Glu Ser Tyr Leu Leu Ala His
1               5                   10
```

```
<210> SEQ ID NO 47
<211> LENGTH: 15
<212> TYPE: PRT
<213> ORGANISM: artificial sequence
<220> FEATURE:
<223> OTHER INFORMATION: modified fragment of Bet v 1 (main birch pollen
      allergen)

<400> SEQUENCE: 47

Cys Gly Pro Cys Leu Arg Ala Val Glu Ser Tyr Leu Leu Ala His
1               5                   10                  15

<210> SEQ ID NO 48
<211> LENGTH: 13
<212> TYPE: PRT
<213> ORGANISM: artificial sequence
<220> FEATURE:
<223> OTHER INFORMATION: modified fragment of thyroperoxidase

<400> SEQUENCE: 48

Gln Gly Gln Leu Met Asn Glu Glu Leu Thr Glu Arg Leu
1               5                   10

<210> SEQ ID NO 49
<211> LENGTH: 13
<212> TYPE: PRT
<213> ORGANISM: Artificial sequence
<220> FEATURE:
<223> OTHER INFORMATION: thyroglobulin fragment

<400> SEQUENCE: 49

Leu Asp Gln Val Ala Ala Leu Thr Trp Val Gln Thr His
1               5                   10
```

IMMUNOGENIC PEPTIDES AND THEIR USE IN IMMUNE DISORDERS

CROSS-REFERENCE TO RELATED APPLICATIONS

This application is a division of U.S. application Ser. No. 14/976,259, filed Dec. 21, 2015, which is a division of U.S. application Ser. No. 12/377,048, filed Feb. 10, 2009, now U.S. Pat. No. 9,249,202, which is a U.S. National Phase of PCT Application No. PCT/EP2007/007165, filed Aug. 13, 2007, which claims the benefit of each of GB Application No. 0711403.6, filed Jun. 13, 2007, GB Application No. 0710081.1, filed May 25, 2007, and GB Application No. 0615966.9, filed Aug. 11, 2006, each of which is incorporated herein by reference in its entirety.

REFERENCE TO SEQUENCE LISTING SUBMITTED ELECTRONICALLY

The content of the electronically submitted sequence listing (Name: 2752.0130 Sequence Listing.txt; Size: 15.9 kilobytes; and Date of Creation: Apr. 13, 2020) filed with the application is incorporated herein by reference in its entirety.

FIELD OF THE INVENTION

The present invention relates to immunogenic peptides and their use in therapies for suppressing allergies and autoimmune disorders.

BACKGROUND OF THE INVENTION

The mammalian immune system is a complex network that serves to protect a subject from external and internal endangering factors. However, in some circumstances, this complex protection mechanism sustains or itself becomes a cause of disorders, mostly with chronic implications, within the subject. Many such immune disorders exist, two important ones being the allergic diseases and the autoimmune disorders. Allergic diseases, conventionally described as type-1 mediated diseases or IgE-mediated diseases, have seen their prevalence almost doubled over the last 20 years. Clinical manifestations of allergic diseases include bronchial asthma, allergic rhinitis, atopic dermatitis, food hypersensitivity and anaphylactic reactions to insect bites or drugs. The economical burden related to the care of allergic patients is steadily increasing over the years. As an example, the cost linked to prescription of allergy treatment in the US is anticipated to reach around 10 billion US dollars in 2006. There is currently no curative therapy for such diseases, which are kept under control by allergen eviction whenever possible, and/or by symptomatic therapy using bronchodilators, anti-histamines, corticosteroids and immunomodulators such as cyclosporine. Allergen desensitisation, which consists in regular administration of allergens to which the patient is sensitised, has shown efficacy in allergic rhinitis, but remains controversial in asthma and atopic dermatitis. Some clinical symptoms, such as those related to food allergens, cannot be treated by desensitisation.

Autoimmunity is the failure of an organism to recognise its own constituent parts (down to the sub-molecular level) as "self", which results in an immune response against its own cells and tissues. Any disease that results from such an aberrant immune response is termed an autoimmune disease. Prominent examples are Systemic Lupus Erythematosus (SLE), Sjögren's syndrome and Rheumatoid Arthritis (RA).

Autoimmune diseases are broadly classified into two categories, namely systemic diseases and organ-specific diseases. The precise aetiology of systemic autoimmune diseases is not identified. In contrast, organ-specific autoimmune diseases are related to a specific immune response including B and T cells, which targets the organ and thereby induces and maintains a chronic state of local inflammation. Examples of organ-specific autoimmune diseases include type 1 diabetes, myasthenia gravis, thyroiditis, multiple sclerosis, celiac disease, inflammatory bowel diseases, atherosclerosis, adrenalitis, polyendocrine syndromes, gastritis, pernicious anemia, ocular diseases such as uveitis, and inner ear diseases such as cochleitis.

Autoimmune reactions are thus directed to own cells or tissues, more particularly to "auto-antigens" i.e. antigens (of proteins) that are naturally present in the mammalian organism. In this mechanism, auto-antigens are recognised by B- and/or T-cells which activate the immune system to attack the tissue comprising the auto-antigen. It is well recognised that suppression of the immune system is beneficial and in some cases leads to partial or complete recovery of organ function in some instances. This kind of therapy is however not effective for all organ-specific autoimmune disease and up to date immune suppression can not be achieved in an antigen-specific manner. Current therapy makes use of non-specific immune suppression obtained by the use of corticosteroids and immunosuppressive agents, all exhibiting significant side effects related to the lack of specificity, thereby limiting their use and their overall efficacy.

Interestingly, for reasons that are far from being understood, the incidence of autoimmune diseases has doubled over the last 20 years, much in parallel to the increase observed in allergic diseases. Again, the cost related to the treatment of autoimmune diseases has increased enormously in recent years, adding a further argument to the need for a new form of therapy.

In the prior art, T-cell epitopes of allergens have been used for desensitisation purposes. Allergen-derived peptides containing one or a few T cell epitope(s) are used in animal experiments and in human beings in an attempt to inhibit specific T cell activation and induce a state of T cell unresponsiveness, such as described in the patent application WO93/08279. One human application of this concept is the administration of a peptide derived from the sequence of T cell epitopes present on the Fel d I allergen, by subcutaneous injections in cat-sensitive individuals (Wallner & Gefter (1994) *Allergy* 49, 302-308). An alternative, complementary approach of this concept has also been used in animal experiments. The peptides used were modified in such a manner as to keep the ability to bind to MHC-class II determinants on specific B cells, but these peptides lost their capacity to activate the corresponding T cells (O'Hehir et al. (1991) Int. Immunol. 3, 819-826).

The screening of the allergen Der p 2 of house mite with a set of overlapping peptides from this protein shows that one specific peptide p21-35 comprises a T-cell epitope which behaves as universal epitope and could be a suitable candidate for T cell anergy induction (Wu et al. (2003) *J. Immunol.* 169, 1430-2435, WO0170263). In a related publication it was shown that this peptide and derivatives thereof have an epitope specific effect on CD4+ CD25+ mediated apoptosis of antigen presenting B cells (Janssens et al. (2003) J. Immunol. 171, 4604-4612), The identification of this peptide however required an exhaustive screening of the allergen and there is no indication that for each and every antigenic protein, such a peptide with an apoptosis-inducing effect can be identified.

It is clear that there is a need for novel strategies or drugs for the prevention or treatment of immune diseases like allergic or autoimmune diseases, which are more effective, more specific, have less-side-effects, are curative instead of merely treating symptoms of disease and are easily accessible, more particularly at low cost. More particularly, for allergic diseases, there is a need for the development of new forms of therapy that are specific for the concerned allergens, that are safe and produce long-lasting beneficial effects.

SUMMARY OF THE INVENTION

The present invention relates to novel immunogenic peptides with cytotoxic activity. The peptides of the invention comprise (i) at least one T-cell epitope of an antigen (self or non-self) with a potential to trigger an immune reaction, coupled, optionally through the use of a linker to (ii) an organic compound having an reducing activity, such as a thioreductase sequence and furthermore optionally comprise an endosome targeting amino acid sequence.

In one aspect the present invention provides isolated immunogenic peptides derived from an antigenic protein comprising an artificial sequence comprising a T cell epitope of the antigenic protein and motif C-X(2)-[CST] or [CST]-X(2)-C, which motif has reducing activity, resulting in a specific response by T cells when contacted with this peptide.

In particular embodiments isolated immunogenic peptides derived from an antigenic protein are provided comprising an artificial sequence comprising a T cell epitope of the antigenic protein and motif C-X(2)-C, whereby the motif is positioned either adjacent to the epitope, or separated from the epitope within the artificial sequence by a linker of at most 7 amino acids. In further particular embodiments, the isolated immunogenic peptide derived from an antigenic protein comprise an artificial sequence comprising a T cell epitope of the antigenic protein and motif C-X(2)-[CST] or [CST]-X(2)-C, whereby the motif is positioned either adjacent to the epitope, or separated from the epitope by a linker of at most 7 amino acids within the artificial sequence and whereby the motif does not naturally occur within a region of 11 amino acids N-terminally or C-terminally of the T-cell epitope in the protein from which the epitope is derived. Further particular embodiments provide isolated immunogenic peptides derived from an antigenic protein comprising an artificial sequence comprising a T cell epitope of the antigenic protein and motif C-X(2)-[ST] or [ST]-X(2)-C, whereby motif is positioned either adjacent to the epitope, or separated from the epitope by a linker of at most 7 amino acids within the artificial sequence, and whereby in those peptides where the motif is C-X(2)-S or S-X(2)-C, the T cell epitope does not comprise the sequence EPCIIHRGKP [SEQ ID. NO: 1] of the p21-35 peptide of Der p 2. Further particular embodiments correspond to immunogenic peptides as described above, wherein for those peptides wherein the motif is C-X(2)-S or S-X(2)-C the antigenic protein is not Der p 2.

Further particular embodiments of the invention relate to immunogenic peptides such as those described hereinabove, which further comprise, linked to the artificial sequence a late endosomal targeting sequence.

Further particular embodiments of the invention relate to immunogenic peptides such as those described hereinabove, comprising the motif positioned N-terminally of the epitope.

Further particular embodiments of the invention relate to immunogenic peptides such as those described hereinabove, wherein the artificial sequence has a length of between 12 and 19 amino acids.

In particular embodiments of the invention, immunogenic peptides are provided such as those described hereinabove, wherein X in the motif is not Tyr, or another bulky amino acid such as Trp or Phe. Additionally or alternatively in particular embodiments, at least one of X in the motif is Gly, Ala, Ser or Thr. Additionally or alternatively in particular embodiments, at least one X in the motif is H or P.

In particular embodiments of the invention, immunogenic peptides are provided such as those described hereinabove, wherein Cysteine in the corresponding motif is methylated. In the case of the motif C-X(2)-C one or both Cysteines in the motif can be methylated.

The immunogenic peptides of the present invention are envisaged to be of use for the generation of an immunosuppressive effect, whereby the targeted immunosuppressive effect will determine the nature of the antigenic protein from which the epitope is derived. In particular embodiments of the immunogenic peptides described hereinabove, the antigenic protein is an auto-antigen, more particularly an auto-antigen selected from the group consisting of thyroglobulin, thyroid peroxidase, TSH receptor, insulin (proinsulin), glutamic acid decarboxylase (GAD), tyrosine phosphatase IA-2, myelin oligodentrodycte protein, heat-shock protein HSP65.

In further particular embodiments of the immunogenic peptides described hereinabove, the antigenic protein is an allergen, more particularly an allergen selected from the group consisting of Betula Bet vi allergen, Bovine beta-lactoglobulin and Der p1.

A further aspect of the present invention relates to the therapeutic and prophylactic use of the immunogenic peptides described hereinabove. Accordingly, the present invention provides peptides such as those described above, for use as a medicament, and pharmaceutical compositions comprising one or more of the peptides described above, optionally comprising a pharmaceutically acceptable carrier.

A further aspect of the present invention relates to the use of the peptides described hereinabove in the treatment and prevention of auto-immune disorders. As indicated above, the peptides are described to have both therapeutic and prophylactic effect thereby allowing a reduction in the occurrence of, a reduction of the occurrence and/or severity of relapses and/or the prevention of the auto-immune disease. Thus the present invention provides the immunogenic peptides described hereinabove, for use in the treatment and prevention of an autoimmune disorder. Specific embodiments of the auto-immune disorders envisaged in the context of the present invention include but are not limited to multiple sclerosis, spontaneous insulin-dependent diabetes and autoimmune thyroiditis.

Yet a further aspect of the present invention relates to the use of the peptides described hereinabove in the treatment and prevention of allergic conditions. As indicated above, the peptides are described to have both therapeutic and prophylactic effect thereby allowing a reduction in the occurrence and/or severity of the allergic condition and/or the prevention of the allergic condition and/or a reduction in the symptoms of the allergic condition. More particularly the present invention provides peptides as described herein for use in the treatment and prevention of an allergic condition selected from the group consisting of dust mite allergy, milk allergy and birch pollen allergy.

Yet a further aspect of the present invention provides methods for preparing a peptide of an antigenic protein capable of eliciting cytolytic CD4+ T cell activity said method comprising the steps of (a) providing a peptide sequence consisting of a T-cell epitope of the antigenic protein, and linking to this peptide sequence a sequence comprising motif C-X(2)-[CST] or [CST]-X(2)-C, such that the motif and the epitope are either adjacent to each other or separated by a linker of at most 7 amino acids. In particular embodiments, the motif is motif C-X(2)-C. In particular embodiments of methods according to this aspect of the invention, the T-cell epitope is an epitope of an antigenic protein which does not naturally comprise the motif C-X(2)-[CST] or [CST]-X(2)-C within a region of 11 amino acids N-terminally or C-terminally of the T-cell epitope and the T-cell epitope is linked to motif C-X(2)-[CST] or [CST]-X(2)-C. In yet other particular embodiments of methods according to this aspect of the invention, where the T-cell epitope comprises the sequence EPCIIHRGKP [SEQ ID. NO: 1] of the p21-35 peptide of Der p 2, the motif is not C-X(2)-S or S-X(2)-C. In further particular embodiments, the antigenic protein is not Der p 2.

In particular embodiments methods of the present invention further comprise modifying the sequence of the peptide thus obtained by modifying the amino acids in the epitope, thereby ensuring that in the modified peptide the sequence of the epitope is modified such that ability to fit into the MHCII cleft is maintained. Such modifications include amino acid substitutions but also include changes in amino acid chain such as modifications encountered in post-translational modifications of amino acids or even non-naturally occurring non-natural amino acid side chains.

Yet a further aspect of the invention relates to methods for preparing an isolated immunogenic peptide of an antigenic protein capable of eliciting cytolytic CD4+ T cell activity, which methods comprise the steps of identifying within the antigenic protein, a sequence comprising a T cell epitope flanked, in the antigenic protein, by motif C-X(2)-[CST] or [CST]-X(2)-C within a region of 11 amino acids N-terminally or C-terminally of said T-cell epitope, and generating a peptide comprising this sequence as an isolated peptide of between 12 and 19 amino acids. It has not previously been demonstrated that in this way, peptides with particular immunogenic properties can be generated. In particular embodiments, the antigenic protein is not Der p 2.

According to further particular embodiments methods according to this aspect of the invention further comprise modifying the sequence of said peptide by modifying the amino acids in the motif and/or by modifying the number of amino acids between the motif and the epitope and/or by modifying the epitope sequence, thereby ensuring that in said modified peptide:
the ability of the T cell epitope to fit into the MHCII cleft maintained,
the motif is conserved and
said motif and said epitope remain adjacent to each other or separated by a linker of at most 7 amino acids.

According to further particular embodiments methods according to this aspect of the invention further comprise the step of attaching a late endosomal targeting sequence to the peptide obtained as described above.

Yet a further aspect of the invention relates to methods of identifying a population of cytotoxic Tregs. In particular embodiments, methods are provided which comprise determining that the cells express CD4, do not express IL-10 or TGF-beta, and express Krox-20 and produce granzymes (in particular Granzymes B and C) and Fas ligand.

In further particular embodiments, methods according to this aspect of the invention comprise determining one or more of the following characteristics, when compared to non-cytotoxic Tregs:
a) an increased expression of surface markers including CD103, CTLA-4, FasL and ICOS upon activation,
b) a high expression of CD25, expression of CD4, ICOS, CTLA-4, GITR and low or no expression of CD127 (IL7-R),
c) the expression of transcription factor T-bet and/or egr-2 (Krox-20) but not of the transcription repressor Foxp3,
d) a high production of IFN-gamma and no or only trace amounts of IL-10, IL-4, IL-5, IL-13 or TGF-beta.
e) an increased expression of markers including FasL and granzymes B and C upon activation.

In further particular embodiments, methods according to this aspect of the invention comprise determining that these cells do not respond to the activation by TCR recognition.

Yet a further aspect of the invention provides methods for obtaining a population of antigen-specific regulatory T cells with cytotoxic properties. In a particular embodiment, methods according to this aspect comprise the steps of:
providing peripheral blood cells,
contacting said cells with an immunogenic peptide as described before and
expanding said cells in the presence of IL-2.

In a further particular embodiment these methods comprise administering an immunogenic peptide according to the present invention to a subject, and isolating from said subject, the antigen-specific regulatory T cells with cytotoxic properties.

Yet a further aspect of the present invention relates to populations of regulatory T cells with cytotoxic properties, obtainable (and/or identifiable) by the methods of the present invention described above.

Yet a further aspect of the present invention provides for the use of the population of T regulatory cells described hereinabove in the treatment and prevention of an allergic condition or an auto-immune disorder.

In particular embodiments of this aspect of the invention, methods are provide which comprise the steps of:
providing peripheral blood cells of the subject to be treated,
contacting the cells with an immunogenic peptide as described herein,
expanding the cells, and
administering the expanded cells to the subject to be treated.

More particularly in methods provided herein an immunogenic peptide is used of which the T-cell epitope is derived from an antigenic protein involved in the disease process to be treated. Most particularly the antigen is a dominant antigen.

The invention further provides methods of treating or preventing an auto-immune disorder in a subject, comprising the steps of administering one or more immunogenic peptides as described herein to said subject. Moreover the invention provides methods for treating or reducing the symptoms an allergic condition in an subject, comprising the steps of administering one or more of the immunogenic peptides as described herein to said subject. More particularly, in methods provided herein, immunogenic peptides are used of which the T-cell epitope is derived from an antigenic protein involved in the disease process to be treated. Most particularly the antigen is a dominant antigen.

Figure 1:
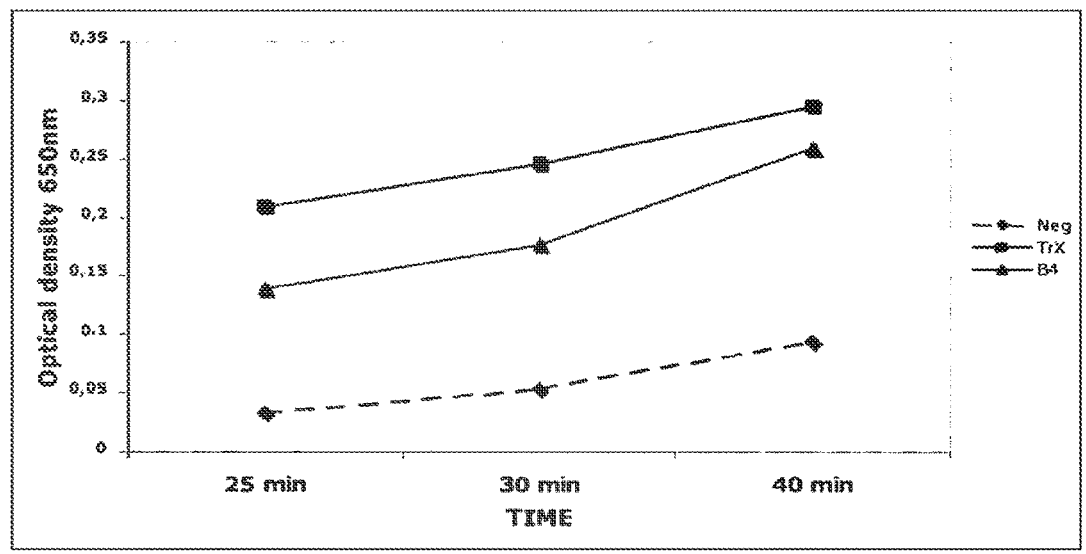
FIG. 1 shows the capacity of p21-35 of Der p 2 to reduce disulfide bridges in the insulin reduction assay (turbidimetric assay) (dashed line: control; solid line with triangles; B4 peptide; solid line with squares: Trx (thioredoxin)

Part C: Left panel: Incubation of WEHI cells (loaded with p21-35met and incubated with R3TB7 Treg (1/1 ratio)) with anti-FasL antibody.

Right panel: Incubation of WEHI cells (loaded with p21-35met and incubated with R3TB7 Treg (1/1 ratio)) with a peptide antagonistic of GZ-B (Z-AAD-CMK) (black squares) or a chemical inhibitor of serine proteases (DCIC: 3,4-dichloroiso-coumarin) (white squares).

Part D: Left panel: Apoptosis measured by Annexin V expression (grey area) of dendritic cells (CD11c+ cells loaded with p21-35 and incubated in the presence of G121 Treg at a 1/1 ratio for 18 hours)

Right panel: as in the left panel, but DC and Treg cells are separated by a semi-permeable membrane in a transwell culture system.

(White area (hidden in panel D) represents annexin V binding on DC without cytotoxic T cells). Results are representative of two independent experiments. Part E: Two populations of WEHI cells were labelled with either 80nM or 300nM of CFSE and incubated for 1 hour with p21-35 or p71-85, respectively. The cells were then incubated with G121 Treg (left panel) or with control CD4+ effector T cells (right panel). Binding of annexin V was analysed by flow cytometry after an incubation of 18 hours.

FIGS. 14A-14F show the suppression of bystander T cells by cytotoxic T cells according to an embodiment of the invention.

Part A: FACS analysis of CFSE stained cells of CD4+ CD25(−) spleen cells, incubated with T cell-depleted splenocytes used as APC, 1 μg/ml anti-CD3 antibody, 1 μg/ml p21-35, and a cytolytic Treg cell line. A ⅓ ratio of Tregs over CD4+CD25(−) T cells was used in uncoated polystyrene culture plates with V-shaped wells to optimise cell contact.

left panels: cytolytic Treg cell line G121
middle panels: cytolytic Treg cell line R3TB7
right panels: control cell culture wherein cytolytic Treg are replaced by unlabeled CD4+CD25(−) splenocytes (right panels). The number of cells, cell divisions and cell size were evaluated by Facs after live cells gating.
top panels: incubation for 48 hours
bottom panels: incubation for 72 hours Part B: Analysis for Annexin V binding on CFSE labelled CD4+CD25(−) T cells after coculture with R3TB7 Treg cell line after 18 hours (middle panel) and after 24 hours (right panel). The left panel shows a control culture (24 hours) without cytolytic Tregs.

Part C: Experiment with the experimental settings of the lower panels of part A, but CFSE divisions were evaluated after 72h of co-culture (except for the left panel), without EGTA and without cytolytic Treg cell line (left panel), in the presence of 2mM EGTA (middle panel) or 4 mM (right panel) of EGTA.

Part D: Labelling of a Der p 1-specific Th2 cell clone with CFSE and cultivation for 72 h with T cell-depleted splenocytes loaded with cognate peptide (amino acids 114 to 128 from Der p 1). Gating was made on propidium iodide negative CFSE positive cells. The left panel shows proliferation determined on a leftward fluorescence shift in the presence of the same unlabeled Th2 cells (ratio 1/1). The second panel from left shows results obtained upon addition of G121 Treg (1/1 ratio with the Th2 clone) plus p21-35 (1 μg/ml) to the culture, in the presence of a control antibody. The next 3 panels (left to right) show the effects obtained when antibodies to FasL, GITR or Lag3 were added from the start of coculture with the cytolytic clone. Each antibody was used at 10 μg/ml. Percentages are for the proportion of PI negative CFSE labelled within total population of CFSE cells.

Part E: Incubation of a CFSE-labelled Th1 clone specific to p71-85 of Der p 2 for 72 hours with an equal number of the same unlabeled clone (left panel). Proliferation is shown as a fluorescence shift to the left. This experiment was repeated but with replacing the unlabeled clone by a cytolytic Treg in a single well (middle panel), or in two wells separated by a transwell membrane (right panel). Cell ratio was 1/1. Results are representative of three independent experiments. Histograms represent PI negative CFSE labelled cells.

Part F: Incubation of T cell-depleted splenocytes with a CFSE-labelled p71-85-specific Th1 clone for 18 hours. The p71-85 peptide was added to activate the clone in each case except for the control (far left panel). To this culture, a p830-844 control cell clone was added with its specific peptide (left panel), or a cytolytic clone (R3TB7) with or without the p21-35 peptide (far right and right panels, respectively). Cell ratio was 1/1. Density dot plots are shown. Results are expressed as average FSC values (upper value, black) and percentages of blasting CFSE cells (lower value, grey). Blast formation was calculated from cell size on CFSE-positive cells in the living lymphocyte gate (established from FSC/SSC plots). The resting lymphocyte gate was adjusted to the region showing the highest density of non-stimulated cells (far left panel). Data are representative of at least 3 experiments.

Figure 15A:
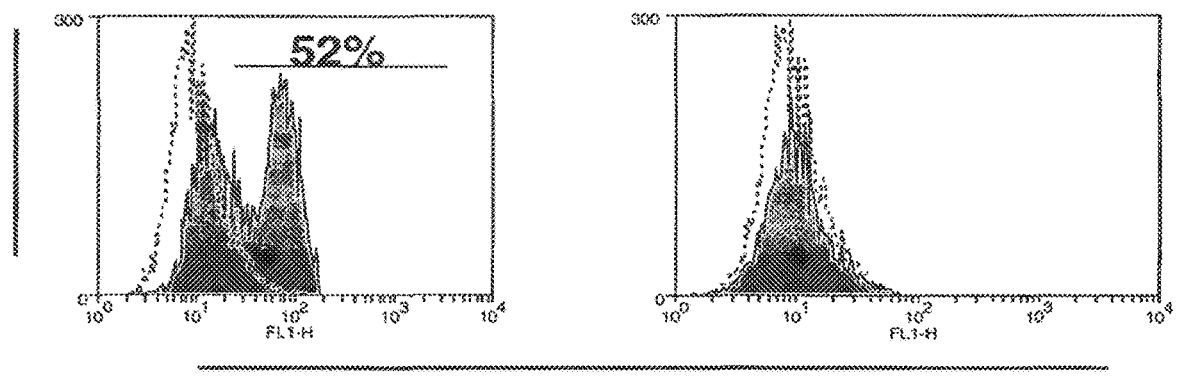

FIGS. 15A-15C show the localisation of cytolytic Tregs to the lungs in allergen-exposed mice and the in vivo induction of apoptosis by antigen presenting B cells according to an embodiment of the invention.

A: Splenic B cells isolated by magnetic beads from naïve BALB/c mice were transduced with a retrovirus vector encoding p21-35 and the gp75 protein. The left panel represents B cells incubated for 18 hours with a cytolytic T cell clone (ratio 2/1). The right panel represents the same assay but carried out with a control CD4+ effector cell. Dashed curves represent anti-caspase-3 staining in B cells cultured without T cells.

B: $5 \times 10^6$ p21-35 transduced B cells were administered IV to each mouse (n=6), followed 5 days later by $5 \times 10^5$ cytolytic Tregs. Two weeks later, mice were sacrificed and cells were prepared from the spleen and lungs by density gradient purification and CD19+ selection using magnetic beads. The presence of mRNA coding for the retroviral construct used to generate transgenic B cells was detected by PCR. A group of mice (n=6) received the transduced B cells but no cytolytic T cells, was treated likewise. Six mice in each group were analysed and representative results are shown in lanes A for spleens of 2 mice treated with the cytolytic Tregs and in lanes B for 2 mice of the control group.

C: $5 \times 10^5$ Vβ8.1+ cytolytic Tregs, or a V8.1+ control T cell clone, were administered IV to naïve BALB/c mice, followed 24 h later by three nasal instillations with 100 microgram Der p 2. Two weeks later, mice were sacrificed and lung lymphocytes prepared by density gradient centrifugation. The proportion of cells expressing Vbeta.8.1 was calculated by Facs within the population of CD4+ cells. Results are expressed as average %±s.e.m. from 6 mice in each group. % CD4 is the percentage of CD4 within the total lymphocytic population; % Vb8.1 is the percentage of cells expressing Vb8.1 within the total CD4 cell population.

FIGS. 16A-16L show the prevention (a-f) and suppression of (g-l) experimental asthma by cytolytic Treg clones according to an embodiment of the invention. Panels A to F show data from mice treated with mp21-35Asn-specific cytolytic Tregs (clones T1 and T3) before IP sensitisation with Der p 2. (The "control T cell clone" is specific for peptide 830-844 of tetanus toxoid, "Der P 2 model" refers to experiments wherein no cells are administered to the cells.)

In panels G to L mice where treated with the above cell lines after IP sensitisation with Der p 2

Panels A and G show total BALF cell numbers;

Panels B and H shows differential BALF cell counts;

Panels C and I shows BALF cytokines as measured by ELISA;

Panels D and J shows a semi-quantitative scoring for lung infiltration by eosinophils and lymphocytes.

Panels E and K show goblet cell counting. Results are expressed as the proportion (%) of goblet cells within the population of epithelial cells after PAS staining;

Panels F and L show airway hyper-reactivity evaluated by inhalation of increasing concentrations of methacholine. PenH values were determined using a whole body plethysmograph. Results are shown as "Area Under The Curve" (AUC) for PenH values. For comparison, AUC values obtained in naïve mice in an independent experiment are shown (naïve). This group gives background values in both prevention and suppression assays.

Data represent results from a minimum of 5 mice per group. Bars represent mean±s.e.m. *P≤5 0.05, **P≤0.01 compared (one-tailed P value) to the Der p 2 model.

Figures 17A, 17B:
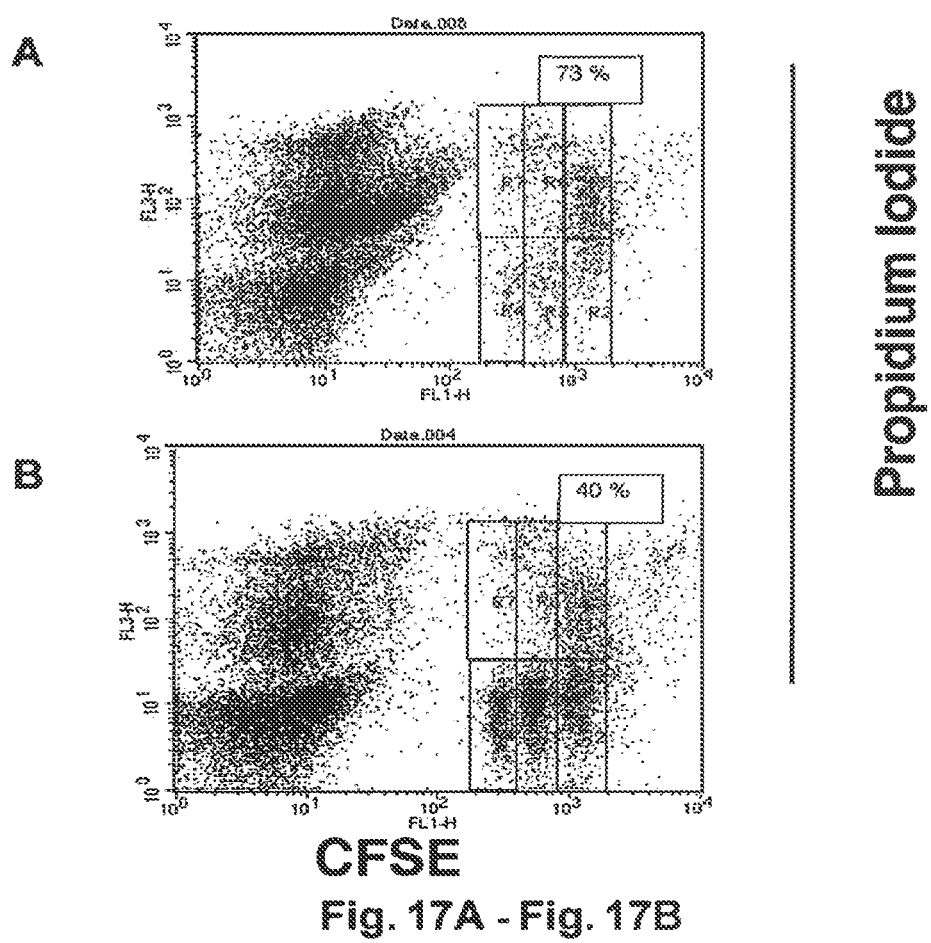

FIGS. 17A-17B show the induction of apoptosis by effector CD4 T cell line specific for Der p1 T cell epitope (114-128), labelled with CFSE and incubated with APC loaded with corresponding peptide (114-128) (upper panel) according to an embodiment of the invention. The lower panel shows baseline mortality (40%) when an identical number of effector cells (unlabelled) replaced the regulatory T cell clone.

Figure 18:
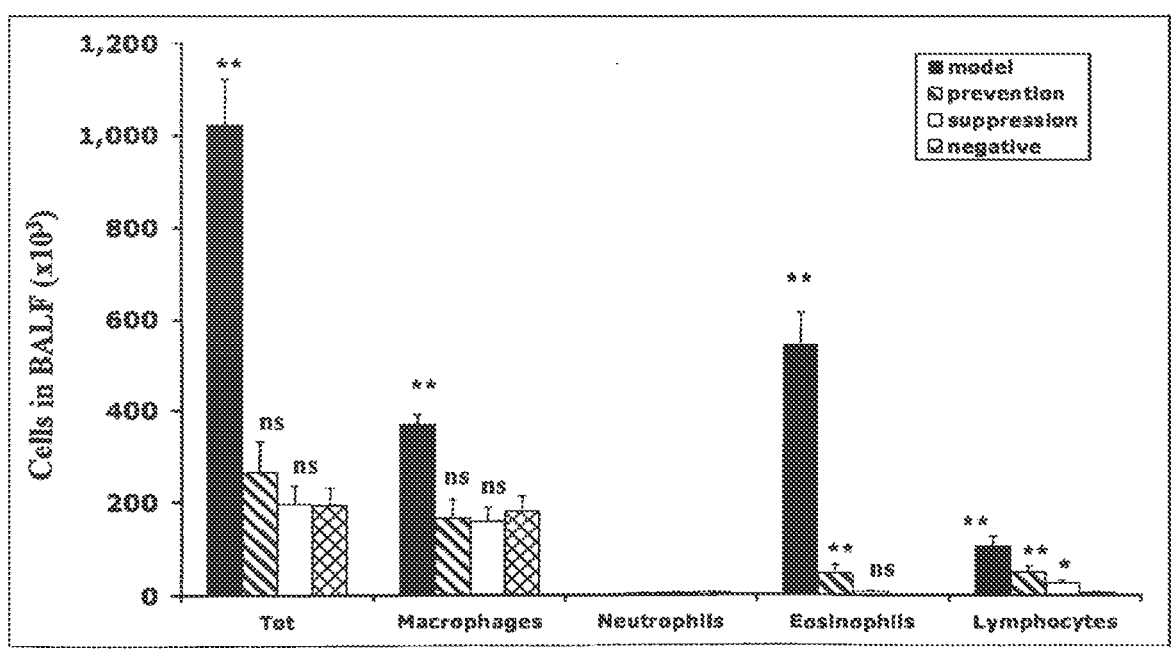
Figure 18:
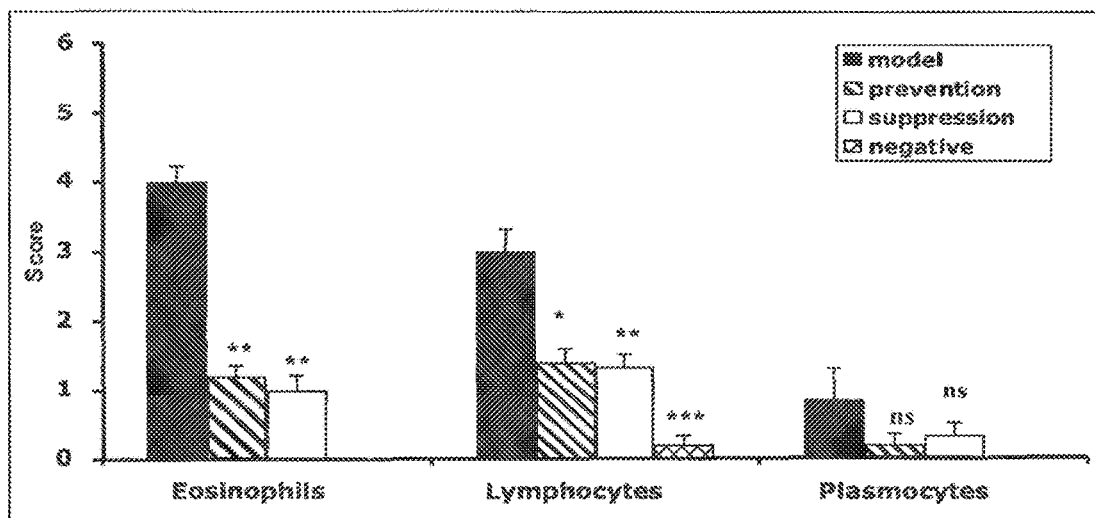

FIG. 18A shows BALF differential cell count was after nasal instillations with either 100 μg Der p1 (model) or NaCl (negative). Mice were adoptively transferred with cytolytic T cells either prior to (prevention) or after is (suppression) the first series of nasal instillation with Der p 1. Bars represent mean±SEM, *p<0.05; **p<0.01 as compared to negative group.

FIG. 18B shows the histology scoring after adoptive transfer of cytolytic T cells according to an embodiment of the invention. Scores were established for eosinophil, lymphocyte and plasmocyte infiltrates using a scale from 0 to 6 (no lesion to massive infiltrate). Mice received 2 series of 3 nasal instillations with either 100 μg Der p 1 (model) or NaCl (negative). Mice were adoptively transferred with cytolytic cells either prior to (prevention) or after (suppression) the first series of nasal instillation with Der p 1. Bars represent mean±SEM, *p<0.05; p<0.01; *p<0.001 as compared to model group.

Figures 19A, 19B:
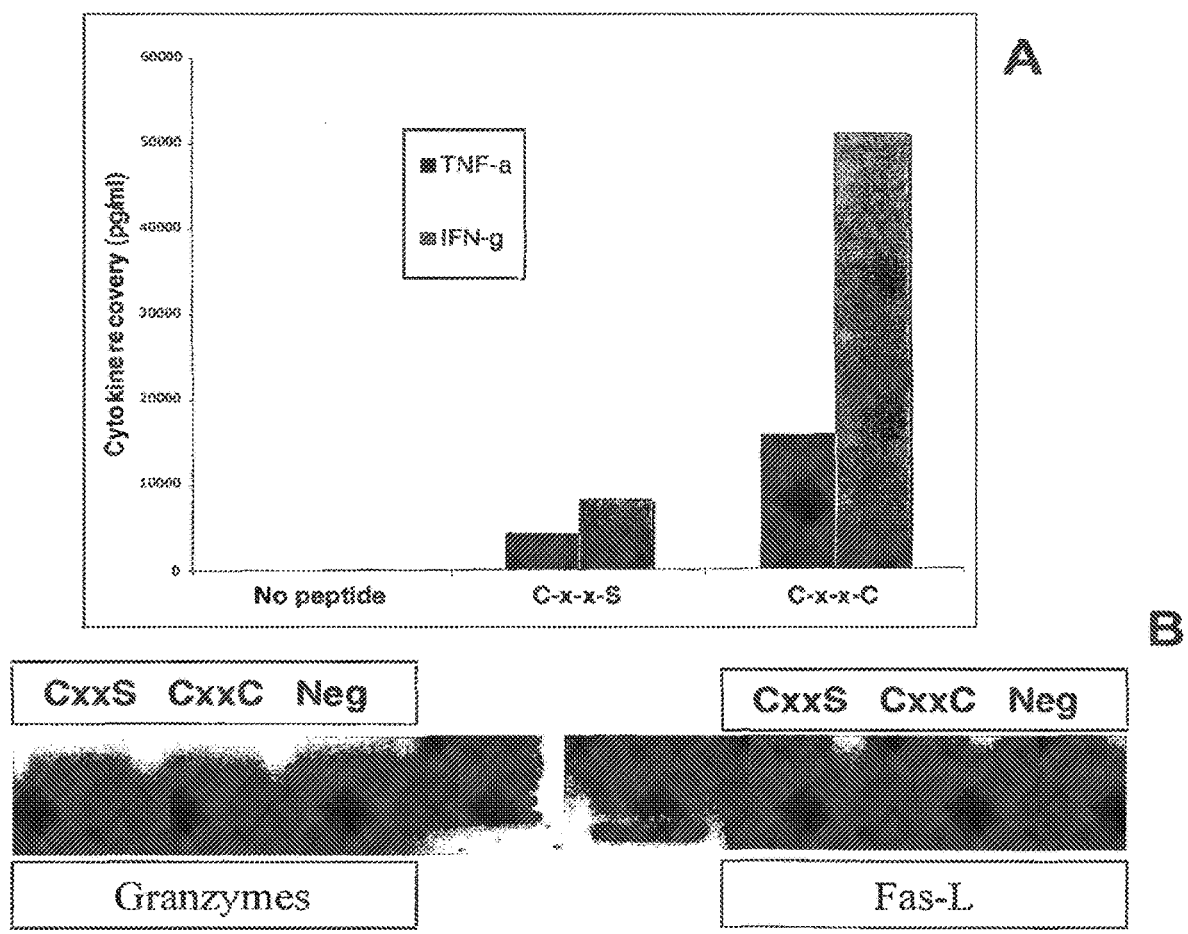

FIG. 19A shows the production of TNF-alpha (black histograms) and IFN-gamma (grey histograms) of cytolytic clone stimulated with APC using no peptide, wildtype p21-35 peptide (C-x-x-S), or Ser24Cys mutated p21-35 (C-x-x-C) according to an embodiment of the invention.

FIG. 19B shows semi-quantitative PCR detection of Granzyme (lanes 1 to 3) and Fas-L (lanes 6 to 8) transcripts. A cytotoxic clone was stimulated with APC loaded with wildtype p21-35 (lanes 1, 6), Ser24Cys modified p21-35 (lanes 2, 7) or without peptide (lanes 3, 8). Lanes 4 and 5 are molecular weight markers.

Figure 20:
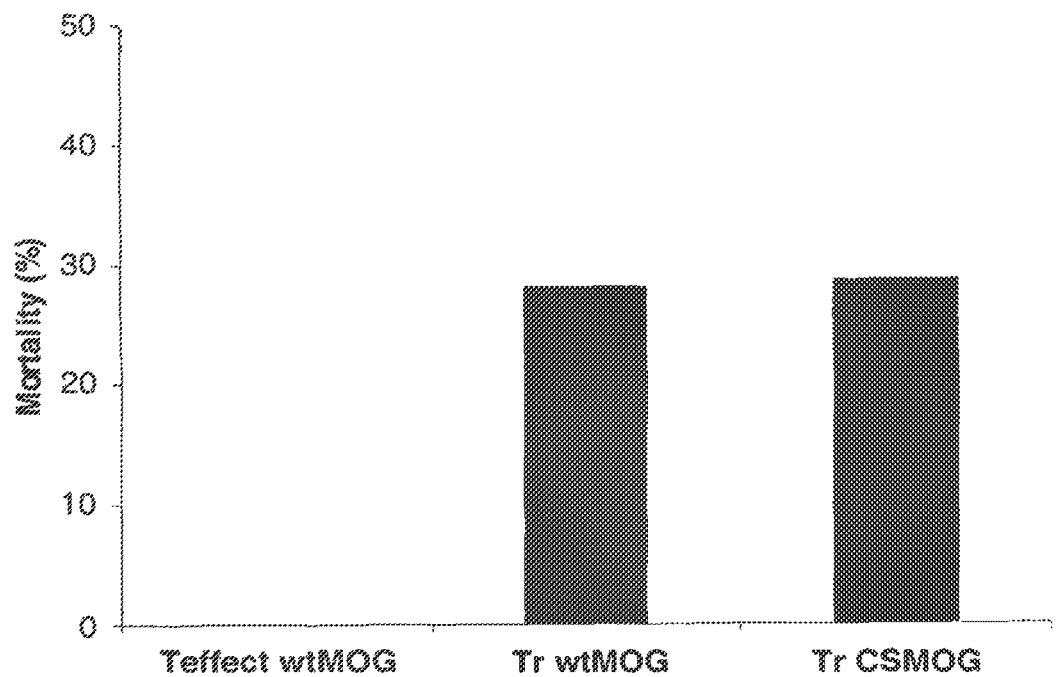

FIG. 20 shows apoptosis of effector T cells labelled with CFSE and co-cultured with APC cells according to an embodiment of the invention. The bars indicate unlabelled T effector cells and wild type MOG peptide: $T_{effect}$ wtMOG; Tr cells and unmodified MOG peptide: Tr wtMOG; Tr cells and modified MOG peptide containing the thioredoxin sequence: Tr CSMOG). CD4+ CD25+ T cells were obtained from animals immunised with MOG peptide containing a thioredoxin consensus sequence (CSMOG). Effector CD4+ CD25− cells were obtained from EAE animals ($T_{effect}$).

Figure 21:
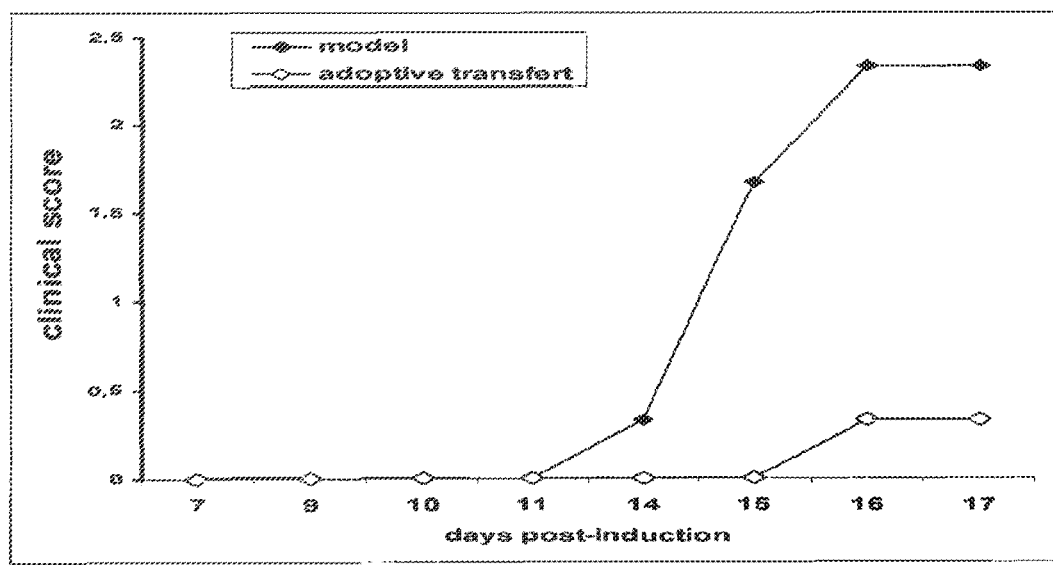

FIG. 21 shows effect on the injection modified MOG peptide on the development of MS in a mouse model. (0: no disease, 1: limp tail, 2: limp tail and loss of weight higher than 10%, 3: partial paralysis of hind limbs, 4: complete paralysis of hind limbs) Model: 3 C57BL/6 mice received, at day 0, SC injection of 100 μg MOG peptide/400 μg *Mycobacterium butyricurn* in CFA and ip injection of 300 ng Bortetella pertussis in NaCl. At day +2, a second injection of B. pertussis was given. Adoptive transfert: 3 mice received iv injection with 500,000 Treg, 24h before disease induction as in model group.

Figure 22:
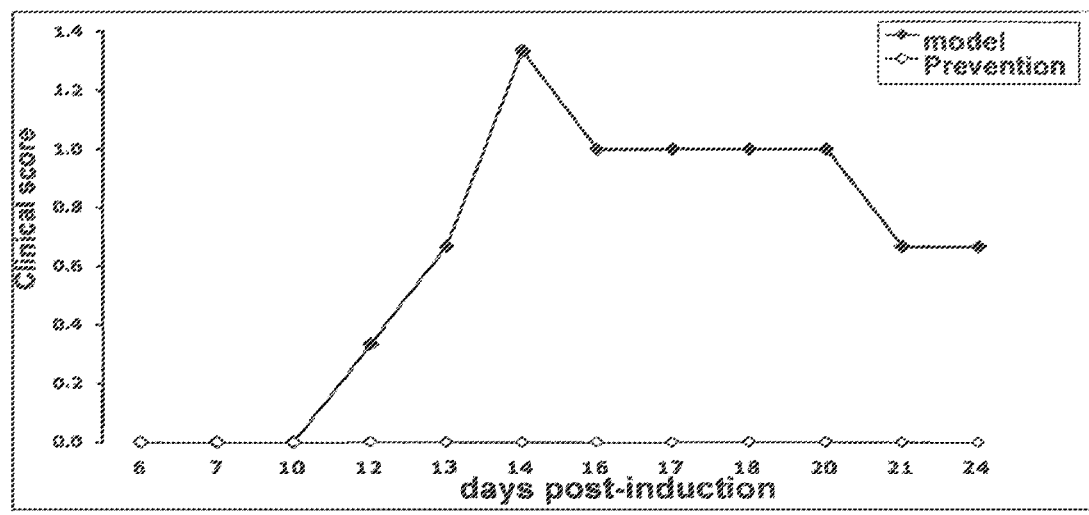

FIG. 22 shows the clinical scoring of mice in with and without prevention by injection of MOG peptide in a model for Multiple Sclerosis.

Figure 23:
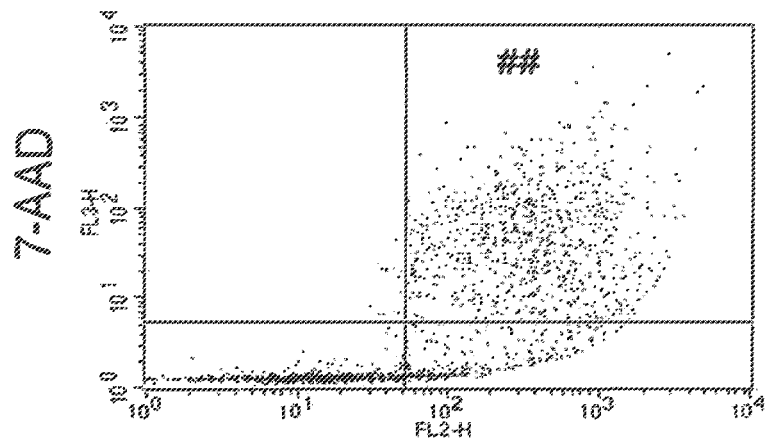

FIG. 23 shows the in vitro induction of apoptosis in CFSE labelled polyclonal CD4 cells from two NOD mice splenocytes. These cells were co-cultured with APC loaded with GAD65 peptide 524-543 [SEQ ID. NO: 34] together with polyclonal CD4 cells purified from modified peptide-treated NOD mice. The figure shows staining of target CD4 cells with 7-AAD and Annexin V-PE. The table represent the percentage of double positive cells (dead cells).

DETAILED DESCRIPTION

Definitions

The term "peptide" as used herein refers to a molecule comprising an amino acid sequence of between 2 and 200 amino acids, connected by peptide bonds, but which can in a particular embodiment comprise non-amino acid structures (like for example a linking organic compound). Peptides according to the invention can contain any of the conventional 20 amino acids or modified versions thereof, or can contain non-naturally occurring amino-acids incorporated by chemical peptide synthesis or by chemical or enzymatic modification.

The term "antigen" as used herein refers to a structure of a macromolecule, typically protein (with or without polysaccharides) or made of proteic composition comprising one or more hapten (s) and comprising T cell epitopes. The term "antigenic protein" as used herein refers to a protein comprising one or more T cell epitopes. An auto-antigen or auto-antigenic protein as used herein refers to a human or animal protein present in the body, which elicits an immune response within the same human or animal body.

The term "food or pharmaceutical antigenic protein" refers to an antigenic protein naturally present in a food or pharmaceutical product, such as in a vaccine.

The term "epitope" refers to one or several portions (which may define a conformational epitope) of an antigenic protein which is/are specifically recognised and bound by an antibody or a portion thereof (Fab', Fab2', etc.) or a receptor presented at the cell surface of a B or T cell lymphocyte, and which is able, by said binding, to induce an immune response.

The term "T cell epitope" in the context of the present invention refers to a dominant, sub-dominant or minor T cell epitope, i.e. a part of an antigenic protein that is specifically recognised and bound by a receptor at the cell surface of a T lymphocyte. Whether an epitope is dominant, sub-dominant or minor depends on the immune reaction elicited against the epitope. Dominance depends on the frequency at which such epitopes are recognised by T cells and able to activate them, among all the possible T cell epitopes of a protein.

Figures 3A, 3B, 3C:
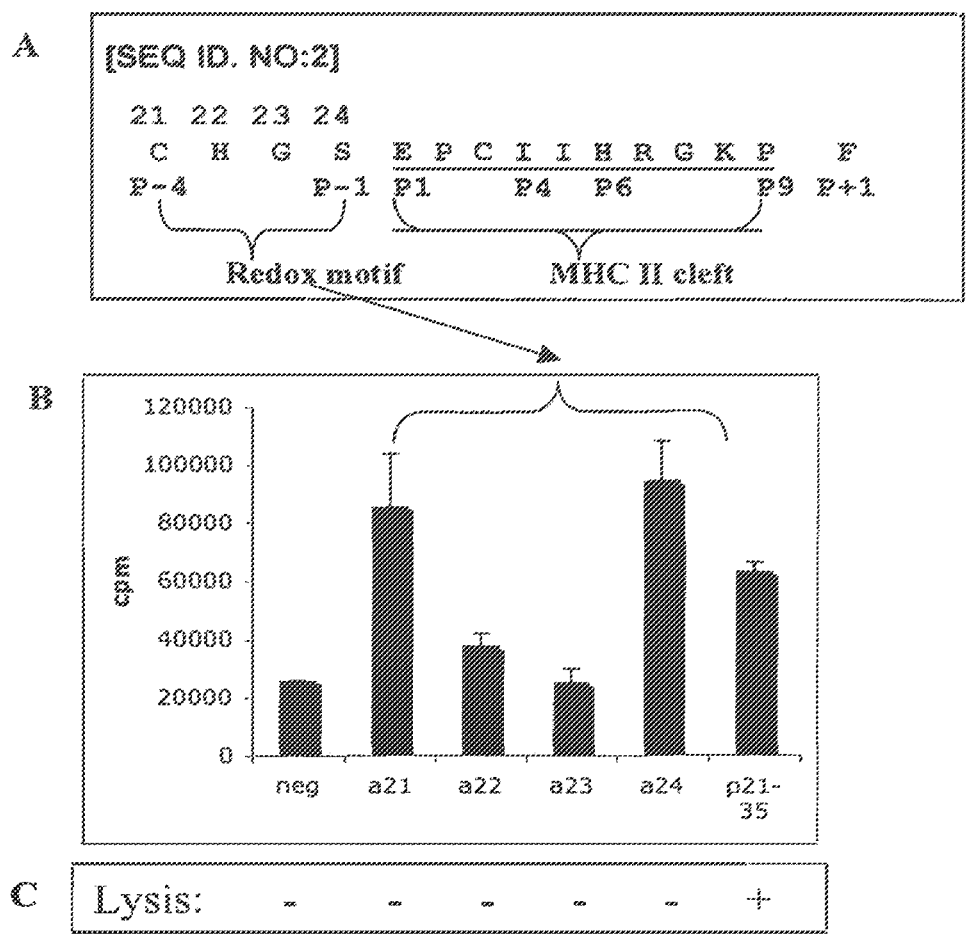
FIGS. 3A-3C show the effect of mutating positions 21 to 24 in P21-35 into Alanine on Treg clone proliferation ($^3$H thymidine incorporation (panel B) and Wehi cell lysis (panel C) according to an embodiment of the invention. The motif and the residues forming the MHC-class II bin Right panel; Incubation (18 hours) of splenic B cells preloaded with p21-35 with a control CD4+ effector T cell clone. White areas with dashed lines represent caspase-3 expression in B cells cultured without T cells; grey areas with solid lines show caspase-3 expression in the presence of the cytolytic Treg clone (left panel) or the CD4+ effector clone (right panel). Staining with Ab against cleaved Caspase 3. Data represent evaluation from a minimum of 3 independent experiments Part B: Left panel: Dendritic cells (CD11c+ dendritic cells activated by LPS) Right panel: WEHI cells Both cell types are loaded with p21-35 and co-cultured with R3TB7 Treg (black areas) or a control non-cytolytic clone of the same specificity (G221N) (white areas). Apoptosis is measured using an Ab against cleaved Caspase 3. Cell count refers to the number of surviving WEHI cells after 18 hours of incubation. Data representative of two experiments. The % suppression indicated is the % of suppression of Wehi growth by R3TB7.

In particular embodiments, a T cell epitope is an epitope recognised by MHC class II molecules, which consists of a sequence of +/−9 amino acids which fit in the groove of the MHC II molecule. Within a peptide sequence representing a T cell epitope, the amino acids in the epitope are numbered P1 to P9, amino acids N-terminal of the epitope are numbered P−1, P−2 and so on, amino acids C terminal of the epitope are numbered P+1, P+2 and so on, as illustrated in FIG. 3A.

The term "homologue" as used herein with reference to the epitopes used in the context of the invention, refer to molecules having at least 50%, at least 70%, at least 80%, at least 90%, at least 95% or at least 98% amino acid sequence identity with the naturally occurring epitope, thereby maintaining the ability of the epitope to bind an antibody or cell surface receptor of a B and/or T cell, Particular embodiments of homologues of an epitope correspond to the natural epitope modified in at most three, more particularly in at most 2, most particularly in one amino acid.

The term "derivative" as used herein with reference to the peptides of the invention refers to molecules which contain at least the peptide active portion (i.e. capable of eliciting cytolytic CD4+ T cell activity) and, in addition thereto comprises a complementary portion which can have different purposes such as stabilising the peptides or altering the pharmacokinetic or pharmacodynamic properties of the peptide.

The term "sequence identity" of two sequences as used herein relates to the number of positions with identical nucleotides or amino acids divided by the number of nucleotides or amino acids in the shorter of the sequences, when the two sequences are aligned. In particular embodiments, said sequence identity is from 70% to 80%, from 81% to 85%, from 86% to 90%, from 91% to 95%, from 96% to 100%, or 100%.

The terms "peptide-encoding polynucleotide (or nucleic acid)" and "polynucleotide (or nucleic acid) encoding peptide" as used herein refer to a nucleotide sequence, which, when expressed in an appropriate environment, results in the generation of the relevant peptide sequence or a derivative or homologue thereof. Such polynucleotides or nucleic acids include the normal sequences encoding the peptide, as well as derivatives and fragments of these nucleic acids capable of expressing a peptide with the required activity. According to one embodiment, the nucleic acid encoding the peptides according to the invention or fragment thereof is a sequence encoding the peptide or fragment thereof originating from a mammal or corresponding to a mammalian, most particularly a human peptide fragment.

The term "organic compound having a reducing activity" refers in the context of this invention to compounds, more in particular amino acid sequences, with a reducing activity for disulfide bonds on proteins. The term "immune disorders" or "immune diseases" refers to diseases wherein a reaction of the immune system is responsible for or sustains a malfunction or non-physiological situation in an organism. Included in immune disorders are, inter alia, allergic disorders and autoimmune diseases.

The terms "allergic diseases" or "allergic disorders" as used herein refer to diseases characterised by hypersensitivity reactions of the immune system to specific substances called allergens (such as pollen, stings, drugs, or food). Allergy is the ensemble of signs and symptoms observed whenever an atopic individual patient encounters an allergen to which he has been sensitised, which may result in the development of various diseases, in particular respiratory diseases and symptoms such as bronchial asthma. Various types of classifications exist and mostly allergic disorders have different names depending upon where in the mammalian body it occurs. "Hypersensitivity" is an undesirable (damaging, discomfort-producing and sometimes fatal) reaction produced in an individual upon exposure to an antigen to which it has become sensitised; "immediate hypersensitivity" depends of the production of IgE antibodies and is therefore equivalent to allergy.

The terms "autoimmune disease" or "autoimmune disorder" refer to diseases that result from an aberrant immune response of an organism against its own cells and tissues due to a failure of the organism to recognise its own constituent parts (down to the sub-molecular level) as "self". The group of diseases can be divided in two categories, organ-specific and systemic diseases.

An "allergen" is defined as a substance, usually a macromolecule or a proteic composition which elicits the production of IgE antibodies in predisposed, particularly genetically disposed, individuals (atopies) patients. Similar definitions are presented in Liebers et al. (1996) *Clin. Exp. Allergy* 26, 494-516.

The term "therapeutically effective amount" refers to an amount of the peptide of the invention or derivative thereof, which produces the desired therapeutic or preventive effect in a patient. For example, in reference to a disease or disorder, it is the amount which reduces to some extent one or more symptoms of the disease or disorder, and more particularly returns to normal, either partially or completely, the physiological or biochemical parameters associated with or causative of the disease or disorder. According to one particular embodiment of the present invention, the therapeutically effective amount is the amount of the peptide of the invention or derivative thereof, which will lead to an improvement or restoration of the normal physiological situation. For instance, when used to therapeutically treat a mammal affected by an immune disorder, it is a daily amount peptide/kg body weight of the said mammal. Alternatively, where the administration is through gene-therapy, the amount of naked DNA or viral vectors is adjusted to ensure the local production of the relevant dosage of the peptide of the invention, derivative or homologue thereof.

The term "natural" when referring to a peptide or a sequence herein relates to the fact that the sequence is identical to a naturally occurring sequence. In contrast therewith the term "artificial" refers to a sequence or peptide which as such does not occur in nature. Optionally, an artificial sequence is obtained from a natural sequence by limited modifications such as changing one or more amino acids within the naturally occurring sequence or by adding amino acids N- or C-terminally of a naturally occurring sequence. Amino acids are referred to herein with their full name, their three-letter abbreviation or their one letter abbreviation.

Motifs of amino acid sequences are written herein according to the format of Prosite. The symbol X is used for a position where any amino acid is accepted. Alternatives are indicated by listing the acceptable amino acids for a given position, between square brackets ('[ ]'). For example: [CST] stands for an amino acid selected from Cys, Ser or Thr. Amino acids which are excluded as alternatives are indicated by listing them between curly brackets ('{ }'). For example: {AM} stands for any amino acid except Ala and Met. The different elements in a motif are separated from each other by a hyphen -. Repetition of an identical element within a motif can be indicated by placing behind that element a numerical value or a numerical range between parentheses. For example: X(2) corresponds to X-X, X(2, 4) corresponds to X-X or X-X-X or X-X-X-X, A(3) corresponds to A-A-A.

The present invention is based upon the finding that a peptide, comprising a T cell epitope and a peptide sequence, having reducing activity is capable of generating a population of regulatory cells which have a cytotoxic effect on antigen presenting cells.

Accordingly, in its broadest sense, the invention relates to peptides which comprise at least one T-cell epitope of an antigen (self or non-self) with a potential to trigger an immune reaction, coupled to an organic compound having a reducing activity, such as a thioreductase sequence motif. The T cell epitope and the organic compound are optionally separated by a linker sequence. In further optional embodiments the peptide additionally comprises an endosome targeting sequence and/or additional "flanking" sequences.

The peptides of the invention can be schematically represented as A-L-B or B-L-A, wherein A represents a T-cell epitope of an antigen (self or non-self) with a potential to trigger an immune reaction, L represents a linker and B represents an organic compound having a reducing activity.

The reducing activity of an organic compound can be assayed for its ability to reduce a sulfhydryl group such as in the insulin solubility assay described in the examples herein wherein the solubility of insulin is altered upon reduction, or with a fluorescence-labelled insulin. The reducing organic compound may be coupled at the amino-terminus side of the T-cell epitope or at the carboxy-terminus of the T-cell epitope.

Generally the organic compound with reducing activity is a peptide sequence. Peptide fragments with reducing activity are encountered in thioreductases which are small disulfide reducing enzymes including glutaredoxins, nucleoredoxins, thioredoxins and other thiol/disulfide oxydoreductases (Holmgren (2000) *Antioxid Redox Signal* 2, 811-820; Jacquot et al. (2002) *Biochem Pharrn* 64, 1065-1069). They are multifunctional, ubiquitous and found in many prokaryotes and eukaryotes. They exert reducing activity for disulfide bonds on proteins (such as enzymes) through redox active cysteines within conserved active domain consensus sequences: C-X(2)-C, C-X(2)-S, C-X(2)-T, S-X(2)-C, T-X(2)-C (Fomenko et al. (2003) *Biochemistry* 42, 11214-11225; Fomenko et al. (2002) *Prot. Science* 11: 2285-2296), in which X stands for any amino acid. Such domains are also found in larger proteins such as protein disulfide isomerase (PDI) and phosphoinositide-specific phospholipase C (Table 1).

TABLE 1

Occurrence of the motif CST-X(2)-CST in representative reducing proteins

| Organism | Protein length | C-X(2)-S position the protein | C-X(2)-S in flanking secondary structure # | and Description |
|---|---|---|---|---|
| D. pteronyssinus | 129 | 21-25 | b-CHGS-coil | Der p 2 allergen |
| E. coil K12 | 115 | 30-35 | b-CGFS-a | Glutaredoxin |
| E. coil K12 | 104 | 14-18 | b-CGTS-a | arsenate reductase |
| S. cerevisiae | 203 | 108-112 | b-CPYS-a | glutaredoxin homologue |
| S. cerevisiae | 231 | 136-140 | b-CSYS-a | glutaredoxin homologue |
| S. cerevisiae | 517 | 62-66 | b-CLHS-a | protein disulfide isomerase |
| H. sapiens | 793 | 72-78 | b-CGHS-a | thioredoxin homologue | b: beta-strand;
a: alpha helix

Accordingly, in particular embodiments, peptides according to the present invention comprise the thioreductase sequence motif [CST]-X(2)-[CST] wherein at least one of [CST] is Cys; thus the motif is either [C]-X(2)-[CST] or [CST]-X(2)-[C]. In the present application such a tetrapeptide will be referred to as "the motif". In particular embodiments peptides of the invention contain the sequence motif [C]-X(2)-[CS] or [CS]-X(2)-[C]. In more particular embodiments peptides contain the sequence motif C-X(2)-S, S-X(2)-C or C-X(2)-C.

As explained in detail further on, the peptides of the present invention can be made by chemical synthesis, which allows the incorporation of non-natural amino acids. Accordingly, in the motif of reducing compounds according to particular embodiments of the present invention, C represents either cysteine or another amino acids with a thiol group such as mercaptovaline. homocysteine or other natural or non-natural amino acids with a thiol function. In order to have reducing activity, the cysteines present in the motif should not occur as part of a cystine disulfide bridge. Nevertheless, the motif may comprise modified cysteines such as methylated cysteine, which is converted into cysteine with free thiol groups in vivo.

The amino acid X in the [CST]-X(2)-[CST] motif of particular embodiments of the reducing compounds of the invention can be any natural amino acid, including S, C, or T or can be a non-natural amino acid. In particular embodiments X is an amino acid with a small side chain such as Gly, Ala, Ser or Thr. In further particular embodiments, X is not an amino acid with a bulky side chain such as Tyr. In further particular embodiments at least one X in the [CST]-X(2)-[CST] motif is His or Pro.

In the peptides of the present invention comprising the motif described above as the reducing compound, the motif is located such that, when the epitope fits into the MHC groove, the motif remains outside of the MHC binding groove. The motif is placed either immediately adjacent to the epitope sequence within the peptide, or is separated from the T cell epitope by a linker. More particularly, the linker comprises an amino acid sequence of 7 amino acids or less.

Most particularly, the linker comprises 1, 2, 3, or 4 amino acids. Alternatively, a linker may comprise 6, 8 or 10 amino acids. In those particular embodiments of the peptides of the invention where the motif sequence is adjacent to the epitope sequence this is indicated as position P−4 to P−1 or P+1 to P+4 compared to the epitope sequence.

Apart from a peptide linker other organic compounds can be used as linker to link the parts of the peptide to each other (e.g. the motif to the T cell epitope sequence).

The peptides of the present invention can further comprise additional short amino acid sequences N or C-terminally of the (artificial) sequence comprising the T cell epitope and the reducing compound (motif). Such an amino acid sequence is generally referred to herein as a 'flanking sequence'. A flanking sequence can be positioned between the epitope and an endosomal targeting sequence and/or between the reducing compound (e.g, motif) and an endosomal targeting sequence. In further embodiments, not comprising an endosomal targeting sequence, a short amino acid sequence may be present N and/or C terminally of the reducing compound and/or epitope sequence in the peptide. More particularly a flanking sequence is a sequence of between 1 and 7 amino acids, most particularly a sequence of 2 amino acids.

In particular embodiments of the peptides of the invention, the motif is located N-terminal from the epitope.

In further particular embodiments, where the motif present in the peptide contains one cysteine, this cysteine is present in the motif in the position remote from the epitope, thus the motif occurs as C-X(2)-[ST] or C-X(2)-S N-terminally of the epitope or occurs as [ST]-X(2)-C or S-X(2)-C C-terminally of the epitope.

In certain embodiments of the present invention, peptides are provided comprising one epitope sequence and a motif sequence. In further particular embodiments, the motif occurs several times (1, 2, 3, 4 or even more times) in the peptide, for example as repeats of the motif which can be spaced from each other by one or more amino acids (e.g. CXXC X CXXC X CXXC), as repeats which are adjacent to each other (CXXC CXXC CXXC) or as repeats which overlap with each other CXXCXXCXXC or CXCCXCCXCC). Alternatively, one or more motifs are provided at both the N and the C terminus of the T cell epitope sequence.

Other variations envisaged for the peptides of the present invention include peptides which contain repeats of a T cell epitope sequence wherein each epitope sequence is preceded and/or followed by the motif (e.g. repeats of "motif-epitope" or repeats of "motif-epitope-motif") Herein the motifs can all have the same sequence but this is not obligatory. It is noted that repetitive sequences of peptides which comprise an epitope which in itself comprises the motif will also result in a sequence comprising both the 'epitope' and a 'motif'. In such peptides, the motif within one epitope sequence functions as a motif outside a second epitope sequence.

In particular embodiments however, the peptides of the present invention comprise only one T cell epitope.

Accordingly, peptides according to the present invention comprise, in addition to a reducing compound, a T cell epitope derived from an antigen, typically an allergen or an auto-antigen, depending on the application. As described below a T cell epitope in a protein sequence can be identified by functional assays and/or one or more in sifico prediction assays. The amino acids in a T cell epitope sequence are numbered according to their position in the binding groove of the MHC proteins. In particular embodiments, the T-cell epitope present within the peptides of the invention consists of between 8 and 25 amino acids, yet more particularly of between 8 and 16 amino acids, yet most particularly consists of 8, 9, 10, 11, 12, 13, 14, 15 or 16 amino acids. In a more particular embodiment, the T cell epitope consists of a sequence of 9 amino acids. In a further particular embodiment, the T-cell epitope is an epitope, which is presented to T cells by MHC-class II molecules. In particular embodiments of the present invention, the T cell epitope sequence is an epitope sequence which fits into the cleft of an MHC II protein, more particularly a nonapeptide fitting into the MHC II cleft.

The T cell epitope of the peptides of the present invention can correspond either to a natural epitope sequence of a protein or can be a modified version thereof, provided the modified T cell epitope retains its ability to bind within the MHC cleft, similar to the natural T cell epitope sequence. The modified T cell epitope can have the same binding affinity for the MHC protein as the natural epitope, but can also have a lowered affinity. In particular embodiments the binding affinity of the modified peptide is no less than 10-fold less than the original peptide, more particularly no less than 5 times less. It is a finding of the present invention that the peptides of the present invention have a stabilising effect on protein complexes. Accordingly, the stabilising effect of the peptide-MHC complex compensates for the lowered affinity of the modified epitope for the MHC molecule. An example hereof is the IIe28Asn substitution of Der p 2 peptide p21-35, which despite a lower affinity for the MHC II cleft, is capable of eliciting the same T cell response as the natural Der p 2 peptide p21-35.

In particular embodiments, the sequence comprising the T cell epitope and the reducing compound within the peptide is further linked to an amino acid sequence (or another organic compound) that facilitates uptake of the peptide into late endosomes for processing and presentation within MHC class II determinants. The late endosome targeting is mediated by signals present in the cytoplasmic tail of proteins and correspond to well-identified peptide motifs such as the dileucine-based [DE]XXXL[LI] or DXXLL motif (e.g. DXXXLL), the tyrosine-based YXXØ motif or the so called acidic cluster motif. The symbol Ø represents amino acid residues with a bulky hydrophobic side chains such as Phe, Tyr and Trp. The late endosome targeting sequences allow for processing and efficient presentation of the antigen-derived T cell epitope by MHC-class II molecules. Such endosomal targeting sequences are contained, for example, within the gp75 protein (Vijayasaradhi et al. (1995) *J Cell Biol* 130, 807-820), the human CD3 gamma protein, the HLA-BM β (Copier et al. (1996) *J. Immunol.* 157, 1017-1027), the cytoplasmic tail of the DEC205 receptor (Mahnke et al. (2000) *J Cell Biol* 151, 673-683). Other examples of peptides which function as sorting signals to the endosome are disclosed in the review of Bonifacio and Traub (2003) *Annu. Rev. Biochem.* 72, 395-447. Alternatively, the sequence can be that of a subdominant or minor T cell epitope from a protein, which facilitates uptake in late endosome without overcoming the T cell response towards the antigen, i.e. allergen or auto-antigen derived T cell epitope.

The late endosome targeting sequence can be located either at the amino-terminal or at the carboxy-terminal end of the allergen or autoantigen-derived peptide for efficient uptake and processing and can also be coupled through a flanking sequence, such as a peptide sequence of up to 10 amino acids. When using a minor T cell epitope for targeting purpose, the latter is typically located at the amino-terminal end of the allergen or autoantigen derived peptide.

Accordingly, the present invention envisages peptides of antigenic proteins and their use in eliciting specific immune reactions. The peptides of the present invention can either correspond to fragments of proteins which comprise, within their sequence, the features of the present invention, i.e. a reducing compound and a T cell epitope separated by at most 10, preferably 7 amino acids or less. Alternatively, and for most antigenic proteins, the peptides of the invention are generated by coupling a reducing compound, more particularly a reducing motif as described herein, N-terminally or C-terminally to a T cell epitope of the antigenic protein (either directly adjacent thereto or with a linker of at most 10, more particularly at most 7 amino acids) so as to obtain the characterising features of the invention. Moreover the T cell epitope sequence of the protein and/or the motif can be modified and/or one or more flanking sequences and/or a targeting sequence can be introduced (or modified), compared to the naturally occurring sequence. Thus, depending on whether or not the features of the present invention can be found within the sequence of the antigenic protein of interest, the peptides of the present invention can comprise a sequence which is 'artificial' or 'naturally occurring'.

The peptides of the present invention can vary substantially in length. In particular embodiments, where the reducing compound corresponds to the motif as described herein, the length of the peptides vary from 12-13 amino acids, i.e. consisting of an epitope of 8-9 amino acids and adjacent thereto the motif as described herein of 4 amino acids, up to 50 or more amino acids. For example, a peptide according to the invention may comprise an endosomal targeting sequence of 40 amino acids, a flanking sequence of about 2 amino acids, a motif as described herein of 4 amino acids, a linker of 4 amino acids and a T cell epitope peptide of 9 amino acids.

Accordingly, in particular embodiments, the complete peptides consist of between 12 amino acids and 20 up to 25, 30, 50, 75, 100 or 200 amino acids. In a more particular embodiments, the peptides consists of between 10 and 20 amino acids. More particularly, where the reducing compound is a motif as described herein, the length of the (artificial or natural) sequence comprising the epitope and motif optionally connected by a linker (referred to herein as 'epitope-motif' sequence), without the endosomal targeting sequence, is critical. The 'epitope-motif' more particularly has a length of 12, 13, 14, 15, 16, 17, 18 or 19 amino acids, optimally of 18 amino acids or less. Such peptides of 12 or 13 to 18 amino acids can optionally be coupled to an endosomal targeting signal of which the size is less critical.

As detailed above, in particular embodiments, the peptides of the present invention comprise a reducing motif as described herein linked to a T cell epitope sequence. According to a particular embodiment the peptides are peptides from proteins which do not comprise within their native natural sequence an amino acid sequence with redox properties in the vicinity (i.e. within a sequence of 11 amino acids N or C terminally) of the epitope of interest, more specifically which do not comprise in their native natural sequence a consensus sequence of thioredoxin, glutaredoxin or thioreductases or homologues thereof, in the vicinity of the epitope of interest. Most particularly, the invention encompasses generating immunogenic peptides from antigenic proteins which do not comprise a sequence selected from C-X(2)-S, S-X(2)-C, C-X(2)-C, S-X(2)-S, C-X(2)-T, T-X(2)-C, or any other consensus sequences which are typical of consensus sequences of thioredoxin, glutaredoxin or thioreductases in the vicinity of the epitope of interest, i.e. within a sequence of 11 amino acids N or C terminally of the epitope sequence. In further particular embodiments, the present invention provides immunogenic peptides of antigenic proteins which do not comprise the above-described amino acid sequences with redox properties within their sequence. In further particular embodiments, the antigenic protein does not naturally comprise the sequence C-H-G-S within a sequence of 11 amino acids N or C terminally of the epitope sequence. More particularly the present invention claims peptides other than peptides comprising epitope EPCIIHRGKP [SEQ ID. NO: 1] of the p21-35 peptide of Der p 2 (CHGSEPCIIHRGKPF [SEQ ID. NO: 2]) and motif C-H-G-S [SEQ ID. NO: 3], in particular those peptides where this motif is located N-terminally from the epitope sequence, as such peptides correspond to peptides generated in the prior art and used for inducing an immune response in the context of epitope mapping of Der p 2 (Wu et al. 2002, J. Immunol. 169, 2430-2435).

In further particular embodiments, the peptides of the invention are peptides comprising T cell epitopes which do not comprise an amino acid sequence with redox properties within their natural sequence.

However, in alternative embodiments, the T cell epitope may comprise any sequence of amino acids ensuring the binding of the epitope to the MHC cleft. Where an epitope of interest of an antigenic protein comprises a motif such as described herein within its epitope sequence, the immunogenic peptides according to the present invention comprise the sequence of a motif as described herein and/or of another reducing sequence coupled N- or C-terminally to the epitope sequence such that (contrary to the motif present within the epitope, which is buried within the cleft) the attached motif can ensure the reducing activity.

In particular embodiments, the peptides of the present invention are not natural but artificial peptides which contain, in addition to a T cell epitope, a motif as described herein, whereby the motif is optionally separated from the T cell epitope by a linker consisting of up to seven, most particularly up to four amino acids.

In a particular embodiment, peptides according to the invention are provided of the Der p 2 protein, comprising a motif as described herein and a Der p 2 epitope. More particularly peptides are provided comprising one or more copies of the nonapeptide epitope EPCIIHRGKP [SEQ ID. NO: 1] of Der p 2 each linked to a reducing motif consisting of the C-X2-C motif. Alternatively, peptides are provided of the Der p 2 protein comprising a T cell epitope other than a sequence comprising EPCIIHRGKP [SEQ ID. NO: 1] linked to a motif C-X(2)-[CST] or [CST]-X(2)-C. The peptides of the invention optionally comprise an endosomal targeting sequence. Most particularly, immunogenic peptides of Der p 2 are provided comprising the C-X2-C motif.

Another aspect of the present invention relates to the processes for generating immunogenic peptides of the present invention described herein.

In a first embodiment of methods according to the present invention a peptide of an antigenic protein capable of eliciting cytolytic CD4+ T cell activity is prepared by providing a peptide consisting of a T-cell epitope of said antigenic protein, and linking to said epitope a reducing compound. More particularly methods according to the invention encompass linking to said T cell epitope a sequence of amino acids corresponding to the motif C-X(2)-[CST] or [CST]-X(2)-C, such that said motif and said epitope are either adjacent to each other or separated by a linker of at most 7 amino acids, more particularly at most 4 amino acids. More particularly, the motif corresponds to C-X2-C. In particular embodiments of the methods of the invention, the T cell epitope of the antigenic protein is selected such that the antigenic protein does not comprise, in its natural sequence, a sequence corresponding to the combined sequence of the epitope and a motif according to the present invention within a region of 11 amino acids N- or C-terminally of said epitope. In further particular embodiments, where the epitope comprises the sequence EPCI-IHRGKP [SEQ ID. NO: 1] of the p21-35 peptide of Der p 2, the motif corresponds to [CT]X2-C or C-X2-[CT], most particularly to C-X2-C. The methods of the present invention generate immunogenic peptides which induce a specific immune response which is not generated, or not to that extent, by the naturally generated T cell epitopes of the antigenic protein. This effect is ensured by the specific combination of T cell epitope and reducing compound, more particularly of T cell epitope and reducing motif.

Accordingly, methods as described above are particularly suited for the generation of immunogenic peptides from allergens or auto-antigens from proteins which do not have a motif such as described herein in their sequence or wherein a motif as described herein is present completely or partially within an epitope sequence of interest or wherein a motif is present outside, but remote (i.e. more than 4, 7, 10 amino acids) from an epitope sequence of interest.

In particular embodiments of the methods described above, one or more further steps are provided whereby a linker is introduced between the T cell epitope and the reducing compound and/or further sequences are added (such as a targeting sequence) and/or one or more flanking sequences and/or modifications are introduced into the epitope sequence of the peptide.

In further embodiments of methods according to the invention of obtaining a peptide capable of eliciting cytolytic CD4+ T cell activity of an antigenic protein, methods are provided which ensure the identification of a suitable immunogenic peptide within an antigenic protein. In these embodiments, the methods of the present invention encompass determining whether the antigenic protein comprises, within its natural sequence, a T cell epitope whereby the protein further comprises within a region of 11, more particularly within a region of 8 amino acids N- or C-terminally of the T cell epitope, a reducing motif as described herein. Accordingly, these embodiments comprise the identification within the antigenic protein of a suitable sequence for use as an immunogenic peptide and the production of a peptide corresponding to the identified sequence. More particularly, the isolated peptides generated in this way comprise a length of between 12 and 19 amino acids. Methods for production of peptides are described below. Where suitable enzymatic cleavage sites are present in the protein, it is further envisaged that the peptides of the present invention can also be generated by enzymatic cleavage from the native protein.

In particular embodiments of the different methods described above, one or more further steps are provided whereby further sequences are added to the peptides obtained, such as a targeting sequence and/or one or more flanking sequences and/or modifications are introduced into the epitope, linker and/or reducing motif of the peptide. These modifications may further enhance the immunogenic properties of the peptide or may improve other characteristics of the peptides such as ease of synthesis, solubility, etc.

The methods described above will allow the generation of an immunogenic peptide according to the present invention only for a selection of antigenic proteins which naturally comprise, in the vicinity of an epitope of interest, a C-X(2)-[CST] or [CST]-X(2)-C motif. In particular embodiments the T cell epitope does not comprise sequence EPCI-IHRGKP [SEQ ID. NO: 1] of the p21-35 peptide of Der p 2. In particular embodiments, the antigenic protein may naturally comprise a C-X(2)-[ST] or [ST]-X(2)-C motif within a sequence of maximally 11 amino acids flanking the epitope of interest, and the methods of the invention generating an isolated peptide comprising said motif and said epitope sequence and modifying said motif to C-X(2)-C so as to further increase the immunogenic properties described herein.

The identification of a suitable T cell epitope of an antigenic protein for use in the generation of peptides as described in the methods above is detailed below.

It has been shown that upon administration (i.e. injection) to a mammal of a peptide according to the invention (or a composition comprising such a peptide), the peptide elicits the activation of T cells recognising the antigen (i.e. the allergen or auto-antigen) derived T cell epitope and provides an additional signal to the T cell through reduction of surface receptor. This supra-optimal activation results in T cells acquiring cytotoxic properties for the cell presenting the T cell epitope, as well as suppressive properties on bystander T cells. In this way, the peptides or composition comprising the peptides described in the present invention, which contain an antigen derived T cell epitope and, outside the epitope, a reducing compound can be used for direct immunisation of mammals, including human beings.

One aspect of the invention thus provides peptides of the invention or derivatives thereof, for use as a medicine. Accordingly, the present invention provides therapeutic methods which comprise administering one or more peptides according to the present invention to a patient in need thereof.

The present invention offers methods by which allergen/antigen-specific T cells endowed with cytotoxic properties can be elicited by immunisation with small peptides. It has been found that peptides which contain (i) a sequence encoding a T cell epitope from an antigen (i.e. allergen, auto-antigen) and (ii) a consensus sequence with redox properties, and further optionally also comprising a sequence to facilitate the uptake of the peptide into late endosomes for efficient MHC-class II presentation, elicit suppressor T-cells.

The immunogenic properties of the peptides of the present invention are of particular interest in the treatment and prevention of immune reactions. Accordingly, another aspect of the present invention provides for the use of the peptides described herein as a medicament, more particularly for the manufacture of a medicament for the prevention or treatment of an immune disorder in a mammal, more in particular in a human.

Another aspect of the present invention thus relates to a method of treatment or prevention of an immune disorder of a mammal in need for such treatment or prevention, by using the peptides of the invention, homologues or derivatives thereof, the methods comprising the step of administering to said mammal suffering or at risk of an immune disorder a therapeutically effective amount of the peptides of the invention, homologues or derivatives thereof such as to reduce the symptoms of the immune disorder. The treatment of both humans and animals, such as, but not limited to pets and horses is envisaged.

The immune disorders referred to above are in a particular embodiment selected from allergic diseases and autoimmune diseases. Allergic diseases are conventionally described as type-1 mediated diseases or IgE-mediated diseases. Clinical manifestations of allergic diseases include bronchial asthma, allergic rhinitis, atopic dermatitis, food hypersensitivity and anaphylactic reactions to insect bites or drugs. Allergic diseases are caused by hypersensitivity reactions of the immune system to specific substances called allergens (such as pollen, stings, drugs, or food). The most severe form of an allergic disorder is anaphylactic shock, which is a medical emergency. Allergens include airborne allergens, such as those of house dust mite, pets and pollens. Allergens also include ingested allergens responsible for food hypersensitivity, including fruits, vegetables and milk.

In order to treat the above diseases, peptides according to the invention are generated from the antigenic proteins or allergens known or believed to be a causative factor of the disease. The allergens that can be used for selection of T-cell epitopes are typically allergens which are selected from the group consisting of:

food allergens present in peanuts, fish e.g. codfish, egg white, crustacea e.g. shrimp, milk e.g. cow's milk, wheat, cereals, fruits of the Rosacea family (apple, plum, strawberry), vegetables of the Liliacea, Cruciferae, Solanaceae and Umbelliferae families, tree nuts, sesame, peanut, soybean and other legume family allergens, spices, melon, avocado, mango, fig, banana, . . . .

house dust mites allergens obtained from *Dermatophagoides* spp or *D. pteronyssinus, D. farinae* and *D. microceras, Euroglyphus maynei* or *Blomia* sp., allergens from insects present in cockroach or Hymenoptera, allergens from pollen, especially pollens of tree, grass and weed, allergens from animals, especially in cat, dog, horse and rodent, allergens from fungi, especially from Aspergillus, Alternaria or Cladosporium, and occupational allergens present in products such as latex, amylase, etc.

The T cell epitope corresponding to an antigenic protein (or immunogen) suitable for use in the context of the present invention is typically a universal or promiscuous T cell epitope (i.e, a T cell epitope capable of binding to a majority of the MHC class II molecules), more particularly present upon an airborne allergen or a foodborne allergen. In particular embodiments, said allergen is selected from the group consisting of rhino-sinusitis allergens, allergic bronchial asthma allergens and atopic dermatitis allergens.

Allergens can also be main allergens present in moulds or various drugs such as hormones, antibiotics, enzymes, etc. (See also the definition in *Clin. Exp. Allergy* 26, 494-516 (1996) and in Molecular Biology of Allergy and Immunology, Ed. R. Bush (1996)). Other allergens related to specific allergic diseases are also well known in the art and can be found on the internet, e.g. on www.allergome.org.

Autoimmune diseases are broadly classified into two categories, organ-specific and systemic diseases. The precise aetiology of systemic auto-immune diseases is not identified. In contrast, organ-specific auto-immune diseases are related to a specific immune response including B and T cells, which targets the organ and thereby induces and maintains a chronic state of local inflammation. Examples of organ-specific auto-immune diseases include type 1 diabetes, myasthenia gravis, thyroiditis and multiple sclerosis. In each of these conditions, a single or a small number of auto-antigens have been identified, including insulin, the acetylcholine muscle receptor, thyroid peroxidase and major basic protein, respectively. It is well recognised that suppression of this organ-specific immune response is beneficial and leads to partial or complete recovery of organ function. There is, however, no therapy, which would suppress such an immune response in an antigen-specific manner. Current therapy rather makes use of non-specific suppression obtained by the use of corticosteroids and immunosuppressive agents, all exhibiting significant side-effects related to their absence of specificity, thereby limiting their use and their overall efficacy. Table 2 shows a non-limiting list of examples of known auto-antigens which are linked to organ specific autoimmune disorders and which are envisaged within the context of the present invention.

TABLE 2

Representative auto-antigens and diseases linked therewith

| Disease | antigen |
|---|---|
| thyroid diseases | thyroglobulin |
| | thyroid peroxidase |
| | TSH receptor |
| type 1 diabetes | insulin (proinsulin) |
| | glutamic acid decarboxylase (GAD) |
| | tyrosine phosphatase IA-2 |
| | heat-shock protein HSP65 |
| | islet-specific glucose6-phosphatase catalytic subunit related protein (IGRP) |
| adrenalitis | 21-OH hydroxylase |
| polyendocrine syndromes | 17-alpha hydroxylase |
| | histidine decarboxylase |
| | tryptophan hydroxylase |
| | tyrosine hydroxylase |
| gastritis & pernicious anemia | H+/K+ ATPase intrinsic factor |
| multiple sclerosis | myelin oligodendrocyte glycoprotein (MOG) |
| | myelin basic protein (MBP) |
| | proteolipid protein (PLP) |
| myasthenia gravis | acetyl-choline receptor |
| ocular diseases | retinol-binding protein (RBP) |
| inner ear diseases | type II and type IX collagen |
| celiac disease | tissue transglutaminase |
| inflammatory bowel diseases | pANCA histone H1 protein |
| atherosclerosis | heat-shock protein HSP60 |

According to the present invention, immunogenic peptides are provided which comprise a T-cell epitope of an antigen (self or non-self) with a potential to trigger an immune reaction, such as an allergen or an auto-antigen, such as those described in Table 2. In a particular embodiment, the T-cell epitope is a dominant T-cell epitope.

Accordingly, in particular embodiments, the methods of treatment and prevention of the present invention comprise the administration of an immunogenic peptide as described herein, wherein the peptide comprise a T-cell epitope of an antigenic protein which plays a role in the disease to be treated (for instance such as those described in Table 2 above). In further particular embodiments, the epitope used is a dominant epitope.

The identification and selection of a T-cell epitope from such antigenic proteins, more in particular from allergens or auto-antigens, for use in the context of the present invention is known to a person skilled in the art.

To identify an epitope suitable for use in the context of the present invention, isolated peptide sequences of an antigenic protein are tested by, for example, T cell biology techniques, to determine whether the peptide sequences elicit a T cell response. Those peptide sequences found to elicit a T cell response are defined as having T cell stimulating activity.

Human T cell stimulating activity can further be tested by culturing T cells obtained from an individual sensitive to e.g. a mite allergen, (i.e. an individual who has an IgE mediated immune response to a mite allergen) with a peptide/epitope derived from the allergen and determining whether proliferation of T cells occurs in response to the peptide/epitope as measured, e.g., by cellular uptake of tritiated thymidine.

Stimulation indices for responses by T cells to peptides/ epitopes can be calculated as the maximum CPM in response to a peptide/epitope divided by the control CPM. A T cell stimulation index (S.I.) equal to or greater than two times the background level is considered "positive." Positive results are used to calculate the mean stimulation index for each peptide/epitope for the group of peptides/epitopes tested.

Non-natural (or modified) T-cell epitopes can further optionally be tested on their binding affinity to MHC class II molecules. This can be performed in different ways. For instance, soluble HLA class II molecules are obtained by lysis of cells homozygous for a given class II molecule. The latter is purified by affinity chromatography. Soluble class II molecules are incubated with a biotin-labelled reference peptide produced according to its strong binding affinity for that class II molecule. Peptides to be assessed for class II binding are then incubated at different concentrations and their capacity to displace the reference peptide from its class II binding is calculated by addition of neutravidin. Methods can be found in for instance Texier et al., (2000) *J. Immunology* 164, 3177-3184.)

According to the present invention, the immunogenic properties of T cell epitopes is increased by linking it to a reducing compound. Particularly, peptides of the present invention comprising at least one T cell epitope and the reducing compound as described herein have a mean T cell stimulation index of greater than or equal to 2.0. A peptide having a T cell stimulation index of greater than or equal to 2.0 is considered useful as a therapeutic agent. More particularly, peptides according to the invention have a mean T cell stimulation index of at least 2.5, at least 3.5, at least 4.0, or even at least 5.0. In addition, peptides have typically a positivity index (P.I.) of at least about 100, at least 150, at least about 200 or at least about 250. The positivity index for a peptide is determined by multiplying the mean T cell stimulation index by the percent of individuals, in a population of individuals sensitive to house dust mite (e. g., at least 9 individuals, at least 16 individuals or at least 29 or 30, or even more), who have T cells that respond to the peptide (thus corresponding to the SI multiplied by the promiscuous nature of the peptide/epitope). Thus, the positivity index represents both the strength of a T cell response to a peptide (S.I.) and the frequency of a T cell response to a peptide in a population of individuals sensitive to house dust mite.

In order to determine optimal T cell epitopes by, for example, fine mapping techniques, a peptide having T cell stimulating activity and thus comprising at least one T cell epitope as determined by T cell biology techniques is modified by addition or deletion of amino acid residues at either the amino- or carboxyterminus of the peptide and tested to determine a change in T cell reactivity to the modified peptide. If two or more peptides which share an area of overlap in the native protein sequence are found to have human T cell stimulating activity, as determined by T cell biology techniques, additional peptides can be produced comprising all or a portion of such peptides and these additional peptides can be tested by a similar procedure. Following this technique, peptides are selected and produced recombinantly or synthetically. T cell epitopes or peptides are selected based on various factors, including the strength of the T cell response to the peptide/epitope (e.g., stimulation index) and the frequency of the T cell response to the peptide in a population of individuals.

Additionally and/or alternatively, one or more in vitro algorithms can be used to identify a T cell epitope sequence within an antigenic protein. Suitable algorithms include, but are not limited to those found on the following websites:
http://antigen.i2r.a-star.edu.sg/predBalbc/;
http://www.imtech.res.in/raghava/mhcbn/;
http://www.syfpeithi.de/home.htm;
http://www-bs.informatik.uni-tuebingen.de/SVMHC;
http://bio.dfci.harvard.edu/Tools/antigenic.html;
http://www.jennerac.uk/MHCPred/.

More particularly, such algorithms allow the prediction within an antigenic protein of one or more nonapeptide sequences which will fit into the groove of an MHC II molecule.

The peptides of the present invention can be generated using recombinant DNA techniques, in bacteria, yeast, insect cells, plant cells or mammalian cells. In view of the limited length of the peptides, they can be prepared by chemical peptide synthesis, wherein peptides are prepared by coupling the different amino acids to each other. Chemical synthesis is particularly suitable for the inclusion of e.g. D-amino acids, amino acids with non-naturally occurring side chains or natural amino acids with modified side chains such as methylated cysteine.

Chemical peptide synthesis methods are well described and peptides can be ordered from companies such as Applied Biosystems and other companies.

Peptide synthesis can be performed as either solid phase peptide synthesis (SPPS) or contrary to solution phase peptide synthesis. The best-known SPPS methods are t-Boc and Fmoc solid phase chemistry:

During peptide synthesis several protecting groups are used. For example hydroxyl and carboxyl functionalities are protected by t-butyl group, lysine and tryptophan are protected by tBoc group, and asparagines, glutamine, cysteine and histidine are protected by trityl group, and arginine is protected by the pbf group. In particular embodiments, such protecting groups can be left on the peptide after synthesis.

Peptides can be linked to each other to form longer peptides using a ligation strategy (chemoselective coupling of two unprotected peptide fragments) as originally described by Kent (Schnolzer & Kent (1992) *Int. J. Pept. Protein Res.* 40, 180-193) and reviewed for example in Tam et al. (2001) *Biopolymers* 60, 194-205 provides the tremendous potential to achieve protein synthesis which is beyond the scope of SPPS. Many proteins with the size of 100-300 residues have been synthesised successfully by this method. Synthetic peptides have continued to play an ever increasing crucial role in the research fields of biochemistry, pharmacology, neurobiology, enzymology and molecular biology because of the enormous advances in the SPPS.

Alternatively, the peptides can be synthesised by using nucleic acid molecules which encode the peptides of this invention in an appropriate expression vector which include the encoding nucleotide sequences, Such DNA molecules may be readily prepared using an automated DNA synthesiser and the well-known codon-amino acid relationship of the genetic code. Such a DNA molecule also may be obtained as genomic DNA or as cDNA using oligonucleotide probes and conventional hybridisation methodologies. Such DNA molecules may be incorporated into expression vectors, including plasmids, which are adapted for the expression of the DNA and production of the polypeptide in a suitable host such as bacterium, e.g. *Escherichia coli*, yeast cell, animal cell or plant cell.

The physical and chemical properties of a peptide of interest (e.g. solubility, stability) is examined to determine whether the peptide is/would be suitable for use in therapeutic compositions. Typically this is optimised by adjusting the sequence of the peptide, Optionally, the peptide can be modified after synthesis (chemical modifications e.g. adding/deleting functional groups) using techniques known in the art.

T cell epitopes on their own are thought to trigger early events at the level of the T helper cell by binding to an appropriate HLA molecule on the surface of an antigen presenting cell and stimulating the relevant T cell subpopulation. These events lead to T cell proliferation, lymphokine secretion, local inflammatory reactions, the recruitment of additional immune cells to the site, and activation of the B cell cascade leading to production of antibodies. One isotype of these antibodies, IgE, is fundamentally important in the development of allergic symptoms and its production is influenced early in the cascade of events, at the level of the T helper cell, by the nature of the lymphokines secreted. A T cell epitope is the basic element or smallest unit of recognition by a T cell receptor where the epitope comprises amino acid residues essential to receptor recognition, which are contiguous in the amino acid sequence of the protein.

However, upon administration of the peptides according to the invention (which comprise a T-cell epitope coupled to a redox sequence) or compositions thereof, the following events are believed to happen:

activation of antigen (i.e. allergen or auto-antigen) specific T cells resulting from cognate interaction with the antigen (i.e. allergen or auto-antigen) derived peptide presented by MHC-class II molecules;

the reductase consensus sequence reduces T cell surface proteins, such as the CD4 molecule (and also CD3), the second domain of which contains a constrained disulfide bridge. This transduces a signal into T cells. Among a series of consequences related to increased oxidative pathway, important events are increased calcium influx and translocation of the NF-kB transcription factor to the nucleus. The latter results in increased transcription of IFN-gamma and granzymes, which allows cells to acquire cytotoxic properties;

the cytotoxicity affects cells presenting the peptide by a mechanism, which involves granzyme B secretion, and Fas-FasL interactions. Destruction of the antigen-presenting target cells prevents activation of other T cells specific for epitopes located on the same antigen, or to an unrelated antigen that would be processed by the same antigen-presenting cell;

an additional consequence of T cell activation is to suppress activation of bystander T cells by a cell-cell contact dependent mechanism. In such a case, T cells activated by an antigen presented by a different antigen-presenting cell is also suppressed provided both cytotoxic and bystander T cells are in close proximity.

The above-postulated mechanism of action is substantiated with experimental data (see examples below). Some experiments have also suggested, in addition, the involvement of the perforin pathway and/or the activation of indoleamine oxidase in target cells, which results in increased tryptophan catabolism, an amino acid essential for cell survival, as well as the production of microparticles by activated Tregs.

Experiments in in vivo models described below have demonstrated that administration (i.e. injection) of a peptide according to the invention or a composition thereof can prevent or suppress an antigen-specific immune response. As an example, in a mouse model of asthma due to sensitisation to an allergen, Der p 2, pre-immunisation with a peptide according to the invention described above prevents lung inflammatory cell infiltration, which is a hallmark of asthma. Non-specific airway hyperreactivity, as measured by inhalation of increasing dosage of methacholine, is essentially prevented by the same experimental protocol. Migration of cells into the broncho-alveolar fluid is also fully prevented (see example 4). Furthermore, adoptive transfer of T cell clones (derived from animals immunised with the composition) fully prevents and suppresses both the infiltration of inflammatory cells and airway hyperreactivity in recipients. Such T cell clones which are elicited by the administration of the peptides according to the invention present a number of phenotypic characteristics, which make them distinct from currently identified Tregs, either natural Tregs or adaptive Tregs. Thus, cytotoxic Tregs show increased expression of surface markers including CD103, CTLA-4, FasL and ICOS (upon activation). They are CD25high even at rest and CD127low (IL7-R). Transcription factor expression includes T-bet but not the transcription repressor Foxp3, considered as a hallmark of natural Tregs. Apart from high production of IFN-gamma, such clones secrete no or only trace amounts of IL-10, IL-4, IL-5, IL-13 or TGF-beta. The above characteristics are not exclusive, but provided as an illustration of the fact that such cytotoxic Tregs are distinguishable from other known Tregs.

Accordingly, in yet a further aspect, the present invention provides methods for generating antigen-specific cytotoxic Tregs either in vivo or in vitro and, independently thereof, methods to discriminate cytotoxic Tregs from other Tregs based on the above-described characteristic expression data.

One aspect of the present invention relates to in vivo methods for the production of the antigen-specific Tregs of the invention. A particular embodiment relates to the method for producing or isolating said Tregs by immunising animals (including humans) with the peptides of the invention as described herein and than isolating the Tregs from said immunised animals. More detailed procedures are described in the Examples section herein and are part of the invention.

A further aspect of the present invention relates to in vitro methods for the production of antigen-specific Tregs of the invention. Tregs are crucial in immunoregulation and have great therapeutic potential. The efficacy of Treg-based immunotherapy critically depends on the Ag specificity of the regulatory T cells. Moreover, the use of Ag-specific Treg as opposed to polyclonal expanded Treg reduces the total number of Treg necessary for therapy. The generation of regulatory T cells in vitro using methods known in the art has a number of important disadvantages. The percentage of Tregs within a sample of isolated peripheral cells is about 5% and the cultivation of Treg cells is difficult, such that the amount of Tregs is always limited. Moreover, the Tregs generated in this way are non-specific and thus are not capable of suppressing a specific immune response, but have only general immunosuppressive effect when administered to a patient. Accordingly, strategies have been developed for the development of selection procedures that allow selection and expansion of highly potent, Ag-specific Tregs. However, the number of antigen-specific Treg cells obtained in this way remains limited.

The present invention provides methods for generating antigen-specific regulatory T cells having cytotoxic activity.

In one embodiment, methods are provided which comprise the isolation of peripheral blood cells, the stimulation of the cell population in vitro by an immunogenic peptide according to the invention and the expansion of the stimulated cell population, more particularly in the presence of IL-2. The methods according to the invention have the advantage that higher numbers of Tregs are produced and that the Tregs can be generated which are specific for the antigenic protein (by using a peptide comprising an antigen-specific epitope).

In an alternative embodiment, the Tregs can be generated in vivo, i.e. by the injection of the immunogenic peptides described herein to a subject, and collection of the Tregs generated in vivo.

The antigen-specific regulatory T cells obtainable by the methods of the present invention are of particular interest for the administration to mammals for immunotherapy, in the prevention of allergic reactions and the treatment of relapses in auto-immune diseases. Both the use of allogenic and autogeneic cells are envisaged.

Accordingly, one aspect of the present invention provides cytotoxic Treg populations characterised as described hereinbelow. More particularly, the populations of Treg populations of the present invention are obtained by the methods described herein.

Accordingly, the present invention provides antigen-specific Tregs with cytotoxic properties according to the invention for use as a medicament, more particularly for use in adoptive cell therapy, more particularly in the treatment of acute allergic reactions and relapses of autoimmune diseases such as multiple sclerosis. The present invention also relates to the use of said isolated Tregs or Treg cell populations generated as described herein, more particularly antigen-specific Treg cell populations generated as described herein for the manufacture of a medicament for the prevention or treatment of immune disorders. Similarly, the invention relates to methods of treatment by using said isolated Tregs or generated Treg population.

A further aspect of the present invention provides methods for discriminating cytotoxic Treg cells from other Treg cells based on expression characteristics of the cells. More particularly, methods according to the invention comprise determining whether the Treg cell population demonstrates one or more of the following characteristics compared to a non-cytotoxic Treg cell population:

an increased expression of surface markers including CD103, CTLA-4, FasL and ICOS upon activation,
high expression of CD25,
expression of CD4, ICOS, CTLA-4, GITR and low or no expression of CD127 (IL7-R),
expression of transcription factor T-bet and egr-2 (Krox-20) but not of the transcription repressor Foxp3,
a high production of IFN-gamma and no or only trace amounts of IL-10, IL-4, IL-5, IL-13 or TGF-beta.

More particularly, the methods of the present invention comprise determining that the cells express CD4, that they do not express IL-10 or TGF-beta, that they express Krox-20 and produce granzymes and Fas ligand. Most particularly these cells are further selected functionally as cells that do not respond to the activation by TCR recognition. In further particular embodiments, the methods encompass determining all of the characteristics described above.

Over recent years much progress has been made in the characterisation of regulatory T cells (Tregs) both in physiological and pathological conditions. More particularly, the potential of using Tregs for the therapy of some diseases has been discussed. The present invention deals with the development of a newly defined subset of antigen-specific adoptive Tregs that differs from previous reported Tregs by the method used for in vitro or in vivo induction and by specific properties. Tregs belong to two broad categories, i.e. natural Tregs and induced (or adaptive) Tregs. Natural Tregs have first been described in the mouse in 1995, and defined as a subset of CD4+ T cells actively selected in the thymus. Such cells are characterised by expression of a number of surface markers, including CD25 on resting cells, GITR, CTLA-4 and LAG-3. More recently, natural Tregs have been further defined by the lack of expression of CD127 (IL-7R). The Foxp3 transcription repressor plays a determining role in the selection of natural Tregs. Mutations of Foxp3 result in the absence of natural Tregs, with an X-linked immune deregulation with polyendocrinopathy, enteropathy, atopic manifestations and lethal infections. Such natural Tregs suppress various inflammatory processes including gastro-intestinal syndromes. At the molecular level, Foxp3 combines with the NEAT transcription factor in competition with AP1 and thereby regulates the transcription of a number of cytokines. The mechanism of action of natural Tregs is under intense scrutiny. In vitro, such cells produce IL-10 and TGF-beta. in viva, however, neutralisation of IL-10 and/or TGF-b does not overcome the suppression, indicating that other mechanisms are at play. In vitro, natural Tregs suppress an adaptive response in a cell contact dependent manner. Interestingly, natural Tregs express granzyme proteases such as granzyme-A (GZ-A) and granzyme-B (GZ-B). Although still controversial, a further or alternative mechanism of action for natural Tregs seems to rely on their capacity to lyse target cells by exocytosis of granzymes. GZ-B deficient Tregs loose partly their capacity to suppress immune response. Adaptive Tregs constitute a heterogeneous family of T cells which have in common to be antigen-specific, to exert a suppressive activity on bystander T cells and to be induced in the periphery. Th3 cells are mainly produced by oral administration of antigen and are found in mesenteric lymph nodes. Such cells exert their suppressive activity by producing high levels of TGF-beta with variable amounts of IL-4 and IL-10. Tr1 cells produce high concentrations of IL-10 and varying amounts of TGF-beta. These are induced in vitro by exposure of naïve CD4+ T cells to high concentrations of IL-10 or combined activation by anti-CD3 and anti-CD46 antibodies. The precise relationship between Th3 and Tr1 cells is not established, in the absence of specific phenotypic markers. Not only an overlap between these two adaptive Tregs seems to exist, but also additional subsets are likely to be defined in forthcoming years. Adaptive Tregs do not express the Foxp3 repressor factor. Apart from the production of suppressive cytokines such as IL-10 and/or TGF-beta, it has been reported that CD4+CD25(−) T cells can be induced to express granzymes, mostly GZ-B, by anti-CD3 and anti-CD46 antibody stimulation. It is not clear whether these non-specific, in vitro induced Tregs exert a cytotoxic activity due to granzyme secretion. The peptides of the invention will, upon administration to a living animal, typically a human being, elicit specific T cells exerting a suppressive activity on bystander T cells. The peptides apparently activate the oxidative metabolism of T cells after cognate interaction and reduce the constrained disulfide bridge of the second extracellular domain of the CD4 molecule.

This mechanism also implies and the experimental results show that the peptides of the invention, although comprising a specific T-cell epitope of a certain antigen, can be used for the prevention or treatment of disorders elicited by an immune reaction against other T-cell epitopes of the same antigen or in certain circumstances even for the treatment of disorders elicited by an immune reaction against other T-cell epitopes of other different antigens if they would be presented through the same mechanism by MHC class II molecules in the vicinity of T cells activated by peptides of the invention.

A further particular aspect of the present invention thus relates to a cell type, being T cells, more in particular Tregs or T suppressor cells, characterised in that they express CD4, that they do not express IL-10 or TGF-beta (whilst other adaptive T cells produce IL-10 and/or TGF beta), that they express Krox-20 and produce granzymes and Fas ligand. Most particularly these cells are further selected functionally as cells that do not respond to the activation by TCR recognition. More particularly, populations of the Treg cell type having the characteristics described herein are provided herein, whereby the anergic response is antigen-specific.

In further particular embodiments, the T reg cells of the invention are characterised in that they have:
expression of CD25, CD4, ICOS, CTLA-4, GITR, and no expression of 00127 (IL7-R),expression of transcription factor T-bet and egr-2 (Krox-20) but not of Foxp3,
an increased expression of markers including FasL and granzymes (B and C) upon activation,
a high production of IFN-gamma.

In a further particular embodiment the invention provides a cell type, being T cells, more in particular Tregs or T suppressor cells, characterised in that they have:
expression of CD25, CD4, ICOS, CTLA-4, GITR, and no expression of CD127 (IL7-R),expression of transcription factor T-bet and egr-2 (Krox-20) but not of Foxp3,
an increased expression of markers including FasL and granzymes (B and C) upon activation,
a high production of IFN-gamma.

Most particularly the Treg cells or cell populations of the invention are characterised in that they have:
an increased expression of surface markers including CD103, CTLA-4, FasL and ICOS upon activation,
high expression of CD25, whilst other adaptive T cells are CD25 negative, expression of CD4, ICOS, CTLA-4, GITR and low or no expression of CD127 (IL7-R),
expression of transcription factor T-bet and egr-2 (Krox-20) but not of the transcription repressor Foxp3, whilst other adaptive T cells are Foxp3 positive,
a high production of IFN-gamma and no or only trace amounts of IL-10, IL-4, IL-5, IL-13 or TGF-beta,
an increased expression of markers including FasL and granzymes (B and C) upon activation.

More particularly, the present invention provides isolated cell populations of the cell type having the characteristics described above, which, in addition are antigen-specific, i.e. capable of suppressing an antigen-specific immune response. Accordingly, the present invention provides isolated antigen-specific Treg cells, characterised as described above. More particularly the present invention provides antigen specific T-reg cells other than those elicited by Der p 2.

The peptides, according to the invention may also be used in gene therapy methods well known in the art and the terminology used herein explaining the use of peptides according to the invention also includes the use of nucleic acids encoding or expressing immunogenic peptides according to the invention.

Accordingly, a further aspect of the present invention relates to nucleic acid sequences encoding the peptides of the present invention and methods for their use.

Different methods of achieving, by way of gene therapy, levels of peptides, homologues or derivatives thereof according to the invention in a mammal in vivo are envisaged within the context of the present invention.

Recombinant nucleic acid molecules encoding protein sequences can be used as naked DNA or in liposomes or other lipid systems for delivery to target cells. Other methods for the direct transfer of plasmid DNA into cells are well known to those skilled in the art for use in human gene therapy and involve targeting the DNA to receptors on cells by complexing the plasmid DNA to proteins. In its simplest form, gene transfer can be performed by simply injecting minute amounts of DNA into the nucleus of a cell, through a process of microinjection. Once recombinant genes are introduced into a cell, they can be recognised by the cells normal mechanisms for transcription and translation, and a gene product will be expressed. Other methods have also been attempted for introducing DNA into larger numbers of cells. These methods include: transfection, wherein DNA is precipitated with calcium phosphate and taken into cells by pinocytosis; electroporation, wherein cells are exposed to large voltage pulses to introduce holes into the membrane); lipofection/liposome fusion, wherein DNA is packed into lipophilic vesicles which fuse with a target cell; and particle bombardment using DNA bound to small projectiles. Another method for introducing DNA into cells is to couple the DNA to chemically modified proteins. Adenovirus proteins are capable of destabilising endosomes and enhancing the uptake of DNA into cells. Mixing adenovirus to solutions containing DNA complexes, or the binding of DNA to polylysine covalently attached to adenovirus using protein crosslinking agents substantially improves the uptake and expression of the recombinant gene. Adeno-associated virus vectors may also be used for gene delivery into vascular cells. As used herein, "gene transfer" means the process of introducing a foreign nucleic acid molecule into a cell, which is commonly performed to enable the expression of a particular product encoded by the gene. The said product may include a protein, polypeptide, anti-sense DNA or RNA, or enzymatically active RNA. Gene transfer can be performed in cultured cells or by direct administration into mammals.

In another embodiment, a vector comprising a nucleic acid molecule sequence encoding a peptide according to the invention is provided. In particular embodiments, the vector is generated such that the nucleic acid molecule sequence is expressed only in a specific tissue. Methods of achieving tissue-specific gene expression are well known in the art. According to one embodiment, this is achieved by placing the sequence encoding a peptide according to the invention under control of a promoter which directs expression in one or more particular tissues.

Expression vectors derived from viruses such as retroviruses, vaccinia virus, adenovirus, adeno-associated virus, herpes viruses, RNA viruses or bovine papilloma virus, may be used for delivery of nucleotide sequences (e.g., cDNA) encoding peptides, homologues or derivatives thereof according to the invention into the targeted tissues or cell population. Methods which are well known to those skilled in the art can be used to construct recombinant viral vectors containing such coding sequences.

Accordingly, the present invention discloses the use of a nucleic acid which is capable of expressing the peptides of the invention, in vivo, for the treatment and/or prevention of allergic and autoimmune diseases. According to one embodiment, the nucleic acid capable of expressing a peptide according to the invention in vivo is a sequence encoding such a peptide, which is operably linked to a promoter. Such a sequence can be administered directly or indirectly. For instance, an expression vector containing the coding sequence for a peptide according to the invention may be inserted into cells, after which the said cells are grown in vitro and then injected or infused into the patient. Alternatively the nucleic acid capable of expressing a peptide according to the invention in vivo is a sequence which modifies endogenous expression of the cells. The gene therapy method may involve the use of an adenovirus vector including a nucleotide sequence coding for peptides, homologues or derivatives thereof according to the invention or a naked nucleic acid molecule coding for a peptide according to the invention. Alternatively, engineered cells containing a nucleic acid molecule coding for a peptide according to the invention may be injected.

Where the administration of one or more peptides according to the invention is ensured through gene transfer (i.e, the administration of a nucleic acid which ensures expression of peptides according to the invention in vivo upon administration), the appropriate dosage of the nucleic acid can be determined based on the amount of peptide expressed as a result of the nucleic acid, such as e.g. by determining the concentration of peptide in the blood after administration. Thus, in a particular embodiment, the peptides of the invention are administered through the use of polynucleotides encoding said peptides, whether in an expression vector or not and thus the present invention also relates to gene therapy methods. Another particular embodiment relates to the use of methods to induce a local overexpression of the peptides of the invention for the treatment or prevention of immune disorders.

Yet another aspect of the present invention provides pharmaceutical compositions comprising one or more peptides according to the present invention, further comprising a pharmaceutically acceptable carrier. As detailed above, the present invention also relates to the compositions for use as a medicine or to methods of treating a mammal of an immune disorder by using said composition and to the use of said compositions for the manufacture of a medicament for the prevention or treatment of immune disorders.

The pharmaceutical composition could for example be a vaccine suitable for treating or preventing immune disorders, especially airborne and foodborne allergy, as well as diseases of allergic origin. As an example described further herein of a pharmaceutical composition, a peptide according to the invention is adsorbed on an adjuvant suitable for administration to mammals, such as aluminium hydroxide (alum). Typically, 50 µg of the peptide adsorbed on alum are injected by the subcutaneous route on 3 occasions at an interval of 2 weeks. It should be obvious for those skilled in the art that other routes of administration are possible, including oral, intranasal or intramuscular. Also, the number of injections and the amount injected can vary depending on the conditions to be treated. Further, other adjuvants than alum can be used, provided they facilitate peptide presentation in MHC-class II presentation and T cell activation. Thus, while it is possible for the active ingredients to be administered alone, they typically are presented as pharmaceutical formulations. The formulations, both for veterinary and for human use, of the present invention comprise at least one active ingredient, as above described, together with one or more pharmaceutically acceptable carriers. A particular embodiment of the present invention relates to pharmaceutical compositions, comprising, as an active ingredient, one or more peptides according to the invention, in admixture with a pharmaceutically acceptable carrier. The pharmaceutical composition of the present invention should comprise a therapeutically effective amount of the active ingredient, such as indicated hereinafter in respect to the method of treatment or prevention. Optionally, the composition further comprises other therapeutic ingredients. Suitable other therapeutic ingredients, as well as their usual dosage depending on the class to which they belong, are well known to those skilled in the art and can be selected from other known drugs used to treat immune disorders.

The term "pharmaceutically acceptable carrier" as used herein means any material or substance with which the active ingredient is formulated in order to facilitate its application or dissemination to the locus to be treated, for instance by dissolving, dispersing or diffusing the said composition, and/or to facilitate its storage, transport or handling without impairing its effectiveness. They include any and all solvents, dispersion media, coatings, antibacterial and antifungal agents (for example phenol, sorbic acid, chlorobutanol), isotonic agents (such as sugars or sodium chloride) and the like. Additional ingredients may be included in order to control the duration of action of the monoclonal antibody active ingredient in the composition. The pharmaceutically acceptable carrier may be a solid or a liquid or a gas which has been compressed to form a liquid, i.e. the compositions of this invention can suitably be used as concentrates, emulsions, solutions, granulates, dusts, sprays, aerosols, suspensions, ointments, creams, tablets, pellets or powders. Suitable pharmaceutical carriers for use in said pharmaceutical compositions and their formulation are well known to those skilled in the art, and there is no particular restriction to their selection within the present invention. They may also include additives such as wetting agents, dispersing agents, stickers, adhesives, emulsifying agents, solvents, coatings, antibacterial and antifungal agents (for example phenol, sorbic acid, chlorobutanol), isotonic agents (such as sugars or sodium chloride) and the like, provided the same are consistent with pharmaceutical practice, i.e. carriers and additives which do not create permanent damage to mammals. The pharmaceutical compositions of the present invention may be prepared in any known manner, for instance by homogeneously mixing, coating and/or grinding the active ingredients, in a one-step or multi-steps procedure, with the selected carrier material and, where appropriate, the other additives such as surface-active agents. They may also be prepared by micronisation, for instance in view to obtain them in the form of microspheres usually having a diameter of about 1 to 10 µm, namely for the manufacture of microcapsules for controlled or sustained release of the active ingredients.

Suitable surface-active agents, also known as emulgent or emulsifier, to be used in the pharmaceutical compositions of the present invention are non-ionic, cationic and/or anionic materials having good emulsifying, dispersing and/or wetting properties. Suitable anionic surfactants include both water-soluble soaps and water-soluble synthetic surface-active agents. Suitable soaps are alkaline or alkaline-earth metal salts, unsubstituted or substituted ammonium salts of higher fatty acids ($C_{10}$-$C_{22}$), e.g. the sodium or potassium salts of oleic or stearic acid, or of natural fatty acid mixtures obtainable form coconut oil or tallow oil. Synthetic surfactants include sodium or calcium salts of polyacrylic acids; fatty sulphonates and sulphates; sulphonated benzimidazole derivatives and alkylarylsulphonates. Fatty sulphonates or sulphates are usually in the form of alkaline or alkaline-earth metal salts, unsubstituted ammonium salts or ammonium salts substituted with an alkyl or acyl radical having from 8 to 22 carbon atoms, e.g. the sodium or calcium salt of lignosulphonic acid or dodecylsulphonic acid or a mixture of fatty alcohol sulphates obtained from natural fatty acids, alkaline or alkaline-earth metal salts of sulphuric or sulphonic acid esters (such as sodium lauryl sulphate) and sulphonic acids of fatty alcohol/ethylene oxide adducts. Suitable sulphonated benzimidazole derivatives typically contain 8 to 22 carbon atoms. Examples of alkylarylsulphonates are the sodium, calcium or alcanolamine salts of dodecylbenzene sulphonic acid or dibutyl-naphtalenesulphonic acid or a naphtalene-sulphonic acid/fomnaldehyde condensation product. Also suitable are the corresponding phosphates, e.g. salts of phosphoric acid ester and an adduct of p-nonylphenol with ethylene and/or propylene oxide, or phospholipids. Suitable phospholipids for this purpose are the natural (originating from animal or plant cells) or synthetic phospholipids of the cephalin or lecithin type such as e.g. phosphatidyl-ethanolamine, phosphatidylserine, phosphatidylglycerine, lysolecithin, cardio-lipin, dioctanylphosphatidylcholine, dipalmitoyiphoshatidylcholine and their mixtures.

Suitable non-ionic surfactants include polyethoxylated and poly-propoxylated derivatives of alkylphenols, fatty alcohols, fatty acids, aliphatic amines or amides containing at least 12 carbon atoms in the molecule, alkylarenesulphonates and dialkylsulphosuccinates, such as polyglycol ether derivatives of aliphatic and cycloaliphatic alcohols, saturated and unsaturated fatty acids and alkylphenols, said derivatives typically containing 3 to 10 glycol ether groups and 8 to 20 carbon atoms in the (aliphatic) hydrocarbon moiety and 6 to 18 carbon atoms in the alkyl moiety of the alkylphenol. Further suitable non-ionic surfactants are water-soluble adducts of polyethylene oxide with poylypropylene glycol, ethylenediaminopolypropylene glycol containing 1 to 10 carbon atoms in the alkyl chain, which adducts contain 20 to 250 ethyleneglycol ether groups and/or 10 to 100 propyleneglycol ether groups. Such compounds usually contain from 1 to 5 ethyleneglycol units per propyleneglycol unit. Representative examples of non-ionic surfactants are nonylphenol polyethoxyethanol, castor oil polyglycolic ethers, polypropylene/polyethylene oxide adducts, tributylphenoxypolyethoxyethanol, polyethyleneglycol and octylphenoxypolyethoxyethanol. Fatty acid esters of polyethylene sorbitan (such as polyoxyethylene sorbitan trioleate), glycerol, sorbitan, sucrose and pentaerythritol are also suitable non-ionic surfactants. Suitable cationic surfactants include quaternary ammonium salts, particularly halides, having 4 hydrocarbon radicals optionally substituted with halo, phenyl, substituted phenyl or hydroxy; for instance quaternary ammonium salts containing as N-substituent at least one C8C22 alkyl radical (e.g, cetyl, lauryl, palmityl, myristyl, oleyl and the like) and, as further substituents, unsubstituted or halogenated lower alkyl, benzyl and/or hydroxy-lower alkyl radicals.

A more detailed description of surface-active agents suitable for this purpose may be found for instance in "McCutcheon's Detergents and Emulsifiers Annual" (MC Publishing Crop., Ridgewood, N.J., 1981), "Tensid-Taschenbucw', 2 d ed, (F-lanser Verlag, Vienna, 1981) and "Encyclopaedia of Surfactants, (Chemical Publishing Co., New York, 1981). Peptides, homologues or derivatives thereof according to the invention (and their physiologically acceptable salts or pharmaceutical compositions all included in the term "active ingredients") may be administered by any route appropriate to the condition to be treated and appropriate for the compounds, here the proteins and fragments to be administered. Possible routes include regional, systemic, oral (solid form or inhalation), rectal, nasal, topical (including ocular, buccal and sublingual), vaginal and parenteral (including subcutaneous, intramuscular, intravenous, intradermal, intraarterial, intrathecal and epidural). The preferred route of administration may vary with for example the condition of the recipient or with the diseases to be treated. As described herein, the carrier(s) optimally are "acceptable" in the sense of being compatible with the other ingredients of the formulation and not deleterious to the recipient thereof. The formulations include those suitable for oral, rectal, nasal, topical (including buccal and sublingual), vaginal or parenteral (including subcutaneous, intramuscular, intravenous, intradermal, intraarterial, intrathecal and epidural) administration. The formulations may conveniently be presented in unit dosage form and may be prepared by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product. Formulations of the present invention suitable for oral administration may be presented as discrete units such as capsules, cachets or tablets each containing a predetermined amount of the active ingredient; as a powder or granules; as solution or a suspension in an aqueous liquid or a non-aqueous liquid; or as an oil-in-water liquid emulsion or a water-in-oil liquid emulsion. The active ingredient may also be presented as a bolus, electuary or paste. A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

For local treatments for example on the skin, such as of the joint, the formulations are optionally applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc), particularly 0.2 to 15% w/w and more particularly 0.5 to 10% w/w. When formulated in an ointment, the active ingredients may be employed with either a paraffinic or a water-miscible ointment base. Alternatively, the active ingredients may be formulated in a cream with an oil-in-water cream base. If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG400) and mixtures thereof. The topical formulations may desirably include a compound which enhances absorption or penetration of the active ingredient through the skin or other affected areas. Examples of such dermal penetration enhancers include dirnethylsulfoxide and related analogues. The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Optionally, a hydrophilic emulsifier is included together with a lipophilic emulsifier which acts as a stabiliser, typically by including both an oil and a fat. Together, the emulsifier(s) with or without stabiliser(s) make up the so-called emulsifying wax, and the wax together with the oil and fat make up the so-called emulsifying ointment base which forms the oily dispersed phase of the cream formulations.

The choice of suitable oils or fats for the formulation is based on achieving the desired cosmetic properties, since the solubility of the active compound in most oils likely to be used in pharmaceutical emulsion formulations is very low. Thus the cream should optionally be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, and particularly butyl stearate, 2-ethylhexyl palmitate or a blend of branched chain esters known as Crodamol CAP may be used. These may be used alone or in combination depending on the properties required. Alternatively, high melting point lipids such as white soft paraffin and/or liquid paraffin or other mineral oils can be used. Formulations suitable for topical administration to the eye also include eye drops wherein the active ingredient is dissolved or suspended in a suitable carrier, especially an aqueous solvent for the active ingredient. The active ingredient is optionally present in such formulations in a concentration of 0.5 to 20%, advantageously 0.5 to 10% particularly about 1.5% w/w. Formulations suitable for topical administration in the mouth include lozenges comprising the active ingredient in a flavoured basis, usually sucrose and acacia or tragacanth; pastilles comprising the active ingredient in an inert basis such as gelatin and glycerine, or sucrose and acacia; and mouthwashes comprising the active ingredient in a suitable liquid carrier. Formulations for rectal administration may be presented as a suppository with a suitable base comprising for example cocoa butter or a salicylate. Formulations suitable for nasal administration wherein the carrier is a solid include a coarse powder having a particle size for example in the range 20 to 500 microns (including particle sizes in a range between 20 and 500 microns in increments of 5 microns such as 30 microns, 35 microns, etc), which is administered in the manner in which snuff is taken, i.e. by rapid inhalation through the nasal passage from a container of the powder held close up to the nose. Suitable formulations wherein the carrier is a liquid, for administration as for example a nasal spray or as nasal drops, include aqueous or oily solutions of the active ingredient, Formulations suitable for aerosol administration may be prepared according to conventional methods and may be delivered with other therapeutic agents. Formulations suitable for vaginal administration may be presented as pessaries, tampons, creams, gels, pastes, foams or spray formulations containing in addition to the active ingredient such carriers as are known in the art to be appropriate. Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

Typical unit dosage formulations are those containing a daily dose or unit daily sub-dose, as herein above recited, or an appropriate fraction thereof, of an active ingredient. It should be understood that in addition to the ingredients particularly mentioned above the formulations of this invention may include other agents conventional in the art having regard to the type of formulation in question, for example those suitable for oral administration may include flavouring agents. Peptides, homologues or derivatives thereof according to the invention can be used to provide controlled release pharmaceutical formulations containing as active ingredient one or more compounds of the invention ("controlled release formulations") in which the release of the active ingredient can be controlled and regulated to allow less frequency dosing or to improve the pharmacokinetic or toxicity profile of a given invention compound. Controlled release formulations adapted for oral administration in which discrete units comprising one or more compounds of the invention can be prepared according to conventional methods. Additional ingredients may be included in order to control the duration of action of the active ingredient in the composition. Control release compositions may thus be achieved by selecting appropriate polymer carriers such as for example polyesters, polyamino acids, polyvinyl pyrrolidone, ethylene-vinyl acetate copolymers, methylcellulose, carboxymethylcellulose, protamine sulfate and the like. The rate of drug release and duration of action may also be controlled by incorporating the active ingredient into particles, e.g. microcapsules, of a polymeric substance such as hydrogels, polylactic acid, hydroxymethylcellulose, polyniethyl methacrylate and the other above-described polymers. Such methods include colloid drug delivery systems like liposomes, microspheres, microemulsions, nanoparticles, nanocapsules and so on. Depending on the route of administration, the pharmaceutical composition may require protective coatings. Pharmaceutical forms suitable for injection include sterile aqueous solutions or dispersions and sterile powders for the extemporaneous preparation thereof. Typical carriers for this purpose therefore include biocompatible aqueous buffers, ethanol, glycerol, propylene glycol, polyethylene glycol and the like and mixtures thereof. In view of the fact that, when several active ingredients are used in combination, they do not necessarily bring out their joint therapeutic effect directly at the same time in the mammal to be treated, the corresponding composition may also be in the form of a medical kit or package containing the two ingredients in separate but adjacent repositories or compartments. In the latter context, each active ingredient may therefore be formulated in a way suitable for an administration route different from that of the other ingredient, e.g. one of them may be in the form of an oral or parenteral formulation whereas the other is in the form of an ampoule for intravenous injection or an aerosol.

The experimental part of the present invention shows a subset of antigen-specific, in vivo induced and easy to expand T cells with regulatory properties. The latter include: (1) induction of APC apoptosis after MHC-class II dependent cognate activation, affecting both dendritic and B cells, and demonstrated in vitro and in vivo, and; (2) suppression of bystander T cells by a contact-dependent mechanism in the absence of IL-10 and/or TGF-β. The present invention further discloses methods to distinguish induced cytolytic Tregs from both natural and adaptive Tregs. Based on characterisation of 15 clones, the surface phenotype is defined as CD25hi, CTLA-4hi, GITR+ and ICOS+, but CD127(−). Such clones express low levels of CD62L and CD103 but not CCR7. Cytokine production was limited to IFN-gamma, with no TGF-beta or IL-10. All clones were Foxp3(−) but strongly positive for T-bet and Egr-2, together with high transcript levels for granzyme B. Natural Tregs are defined by expression of Foxp3 and absence of CD127, produce high levels of IL-10, at least in vitro, and are specific for autoantigens. Among the numerous adaptive T cells described so far, most share the production of IL-10 (and TGF-beta in some cases such as in Th3 cells) and are Foxp3 and CD25 negative. Central to cytolytic Tregs is the strong expression of T-bet. T-bet is induced by IFN-γ via a STAT1-dependent pathway and exerts different activities, including suppression of IL-2 transcription, induction of granzyme transcription and is a maturation factor for Th1 differentiation.

No transcript for IL-2 was found in the T cell clones of the present invention and, interestingly, exogenous IL-2 did not restore IL-2 transcription, even after repeated stimulation cycles in vitro. This suggests that cytolytic Tregs have undergone an epigenetic alteration, which would sustain their regulatory activity both in vitro and in vivo. Although T-bet is required for the maturation of the Th1 subset, its expression does not necessarily qualify cells as belonging to such lineage. Induction of granzyme B by T-bet has been observed with CD8+ cytolytic T cells. The Tregs described here are anergic in the sense that they were unable to proliferate and/or produce IL-2 upon cross-linking of their antigen receptor. Interestingly, this anergic state could be overcome by addition of IL-2. A high expression was observed of the transcription factor Egr-2 (Krox-20), which upregulates cell cycle inhibitors such as $p21^{clip1}$ and $p27^{kip}$. It is known that IL-2 can override Egr-2-mediated suppression, possibly via activation of NF-kB. The latter upregulates granzyme transcription, which might synergise with T-bet for the production of granzyme. It should be kept in mind that the regulatory properties are not lost when cells are stimulated by addition of IL-2. In a particular embodiment, this is a property of the present cytolytic Tregs, a seemingly stable cell subset that exerts its regulatory activity upon IL-2 dependent activation. Induction of apoptosis is the mechanism at the basis of regulatory activity. This was demonstrated at both the level of APC and bystander T cells by showing activation of caspase 3 and/or annexin V binding. It was shown that the two main pathways leading to apoptosis were activated in cytolytic Tregs. Both GrB and perforin production were induced by activation of Tregs, with increased transcription for GrB but not granzyme A. GrB, as opposed to GrA, induces apoptosis by at least two mechanisms, namely direct and indirect activation of pro-caspase 3, the latter through the release of cytochrome C by mitochondria and caspase 9 activation. Specific inhibitors of GrB showed significant reduction in apoptosis induction, and only at concentrations close to cell cytotoxicity. Whether perforin is required for such an activity is doubtful, as EGTA did not block apoptosis to any significant degree. The second pathway by which apoptosis can be induced is the Fas-FasL pathway. Interestingly, FasL is present in exocytose granules together with granzymes, and anchors to the membrane upon cell activation, which constitutes the main pathway for FasL expression in T cells. FasL signals through Fas leading to caspase 8 activation, with a downstream activation of caspase 3 and caspase 9 through mitochondrial release of cytochrome C, thereby synergising with GrB. Partial inhibition of apoptosis was obtained using a FasL-specific antibody. The relative participation of the GrB and FasL pathways is dictated by the extent of FasL expression. Thus, Wehi cells, which have a constitutive high expression of Fas are readily lysed by Tregs, as compared for instance with dendritic cells, Whether the combined action of GrB and FasL accounts for all cytolytic activity is not fully established, as preliminary experiments have shown that the combination of the two inhibitors did not abolish target cell apoptosis. Granzymes are known to be secreted by some Tregs. Thus, granzyme B is involved in the mechanism by which natural Tregs control immune responses, both in human and in the mouse, GrB KO mice have a defect in regulation. It is, however, difficult to establish to what extend induced Tregs use granzymes to exert their regulatory activity. One report shows that a proportion of Tr1-like Tregs activated by anti-CD3 and anti-CD46 antibodies express GrB. A yet-to-be solved difficulty with granzymes is the lack of specific and efficient inhibitors. Chemical or peptide inhibitors, such as those used in the present invention (Example 11), required high concentrations to be active. The use of the Fas-FasL pathway has not been earlier reported in adaptive Tregs, and very few data indicate that natural CD4+CD25+ Tregs could also use Fas-L as mechanism. Noteworthy, apoptosis induction is observed with dendritic cells and with B cells, suggesting that both primary and secondary immune responses can be regulated. In addition, Tregs recognising a single T cell epitope from even complex antigens have the capacity to suppress the response to the entire protein by eliminating the antigen-presenting cell. This is well illustrated by the in vivo data, in which the response toward a full allergen, Der p 2, is suppressed after adoptive transfer of a single Treg clone. This effect is reinforced by the suppression of bystander T cells even when the latter are activated by interaction with a different APC, provided cell contact is possible between Tregs and effector T cells. Interestingly, Tregs can regulate effector T cells at various maturation stages, Th0, Th1 or Th2. Importantly, cytolytic Tregs induce apoptosis in target cells and not necrosis. Apoptotic APC may play a role in suppression. It has indeed been demonstrated that apoptotic cells taken up by antigen-presenting cells induce tolerance, while necrotic cells rather induce inflammation. In vivo, the nearly complete suppression of inflammation within lungs should certainly be considered as a token for target cell apoptosis instead of necrosis. An aspect of the present invention is the demonstration that B cell apoptosis also occurs in vivo. Thus, mice adoptively transferred with transgenic B cells expressing p21-35 followed by cytolytic Tregs of corresponding specificity show complete disappearance of B cells, as detected in the spleen. It is unlikely that transgenic B cells would have migrated to other sites. No evidence for such cells was found in lungs or in the liver. The functional properties of p21-35 transgenic cells are identical to those of B cells incubated with the peptide in a conventional loading assay. It is shown here that transgenic B cells are induced into apoptosis in vitro by co-culture with cytolytic Tregs, indicating good evidence for the in vivo relevance of APC cytolysis. Particular attention was paid to the possible involvement of IL-10. Natural Tregs as well as most if not all described subsets of adaptive Tregs produce IL-10 (Levings et al. (2002) *Int. Arch. Allergy Immunol.* 129, 263-276, One of these subtypes was induced after respiratory exposure to allergen and expressed Foxp3, GATA3, and produced no IFN-γ (Akbari et al. (2002) *Nature medicine* 8, 1024-1032). Another type was induced during strong Th1 polarising conditions (*Listeria monocytogenes* as adjuvant), expressed Foxp3, T-bet, and produced IFN-γ (Stock et al. (2004) *Nat. Immunol.* 5, 1149-1156). Both subsets were able to inhibit airway hyper-reactivity and inflammation via an IL-10 dependent mechanism. There was no evidence for IL-10 production by the Foxp3 negative cytolytic Tregs nor activation of STAT5 or SP1. The observation that the induction of apoptosis required direct cell contact as shown in transwell experiments, and the known suppression of IL-10 transcription by IFN-gamma, the latter being produced at high levels by all of the cytolytic Tregs, were taken as evidence against a significant involvement of IL-10 in cytolytic Treg activity. Remarkably, a mild adjuvant such as alum is all that was required. Interestingly, immunisation with the mp21-35 peptide made in CFA/IFA was even more effective in suppressing airway inflammation and hyperreactivity, but this was to the detriment of accumulation of large numbers of Th1 lymphocytes into lungs. In addition, this shows that immunisation in CFA failed to elicit cytolytic Tregs. Methylation of cysteine increased MHC class II presentation, but this is attributable to increased stability of peptide and increased uptake by APC. Interestingly, it was not possible to induce cytolytic Tregs towards a second major T cell epitope of Der p 2, p71-85. Substitution of isoleucine 28 by asparagine reduced binding affinity to MHC class II molecules, which was shown not to be detrimental to the elicitation of cytolytic Tregs. Altered peptides carrying T cell epitopes have been reported to either increase binding affinity and/or TCR recognition, or to induce tolerance, an outcome often difficult to predict. In the present case, both effector and cytolytic Tregs recognised the same epitope, and could be expanded in vitro with p21-35 in either its wild type or mutated sequence.

An interesting aspect of the present study was the demonstration that cytolytic Tregs migrated towards the lung upon airway exposure to the allergen Der p 2, and this, in the absence of peripheral allergen sensitisation. Chemokines involved in attracting T lymphocytes to the lung are not precisely identified. The cytolytic Tregs described here express CD103 but not CCR7, which should confer them with the capacity to migrate to inflamed tissues. Other chemokines such as CCR5 and CCR3 were not detected. However, the model system used here, in which mice adoptively transferred with cytolytic Tregs are submitted to 2 series of 3 nasal instillations at one-week interval, does not elicit significant inflammation in the lungs, as shown in control mice submitted to allergen inhalation only. In an experimental model of asthma, including peripheral sensitisation and allergen inhalation, it was shown that Tregs have the capacity to prevent and suppress both inflammatory infiltration and airway hyperreactivity, which are the hallmarks of bronchial asthma. An LPS-free recombinant form of a main allergen, Der p 2, was used, which is involved in a large proportion of patients suffering from allergic asthma. In parallel studies, it was determined that the p21-35 peptide activated CD4+ effector T cells from patients sensitised to Der p 2. A p21-35 specific T cell clone derived from such a patient shows properties comparable to those of mouse cytolytic Tregs, which suggests that cytolytic Tregs are generated as part of a normal immune response to an allergen such as Der p 2.

These observations support the utility of cytolytic Tregs according to the invention for treating allergic asthma in the clinic. Cytolytic Tregs are activated and easily expanded by MHC class II-restricted epitope presentation, and do not produce suppressive cytokines, which provides the specificity required for clinical use. In addition, such Tregs are obtained upon immunisation using conventional adjuvant, namely alum, with no requirement for bacteria-derived material such as mycobacterium or CFA. Most encouraging is the observation that airway hyperreactivity to a non-specific stimulant, namely metacholine, was significantly reduced even after allergen sensitisation. This was unexpected, as airway inflammation and hyperreactivity are not necessarily linked. In fact, in the model of asthma to Der p 2, the two phenomena are dissociated from each other.

The present invention will now be illustrated by means of the following examples which are provided without any limiting intention. Furthermore, all references described herein are explicitly included herein by reference.

EXAMPLES

Example 1: P21-35 Contains a Thioredoxin/Glutaredoxin Consensus Sequence

Table 1 shows the amino acid sequence homology between a fragment of p21-35 and C-X(2)-S redox motifs in proteins from different organisms.

FIG. 1 shows the capacity of p21-35 to reduce disulfide bridges in the insulin reduction assay (turbidimetric assay). Herein, an insulin solution (1 mg/ml) containing DL-Dithiothreitol was incubated with a reducing protein or peptide or control for 20 minutes at 25° C. The increase in optical density at 650 nm (Y axis) due to precipitation of reduced insulin at pH 7 was then measured at different time points (X axis). A recombinant tetramer of p21-35 (B4) [SEQ ID. NO: 4] was used with recombinant thioredoxin as positive control.

Figure 2:
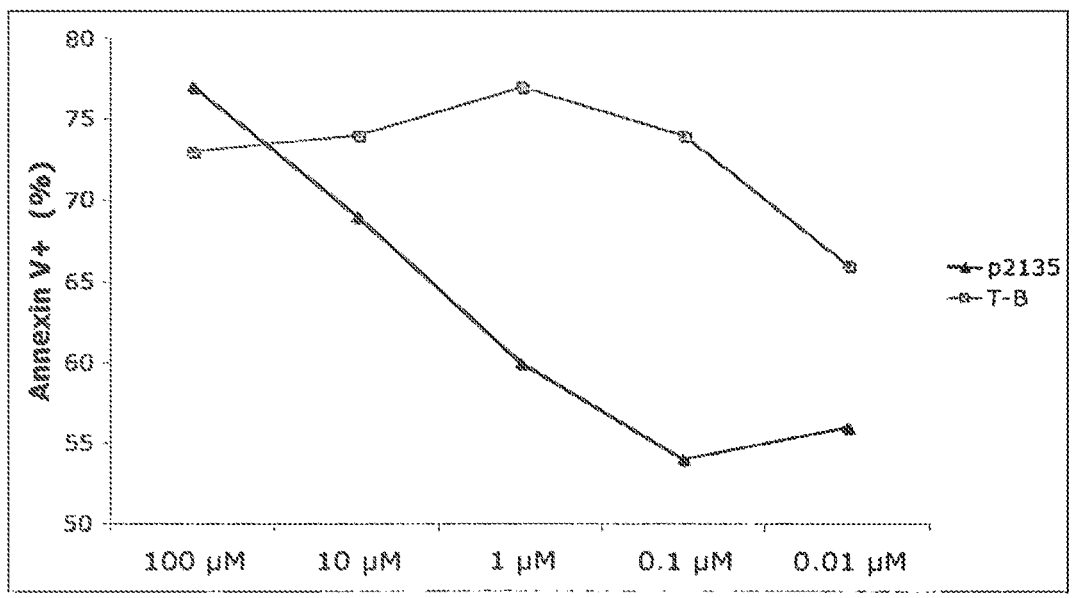
FIG. 2 shows the increase of uptake of p21-35 by antigen-presenting cells (assayed by apoptosis of target Wehi B cells) by addition of a subdominant T cell epitope (grey line with squares: T-B peptide (p21-35 linked to the minor T epitope (p830-844) of tetanus toxin; black line with triangles: p21-35 peptide).

Example 2: Uptake of p21-35 by Antigen-Presenting Cells is Increased by Addition of a Subdominant T Cell Epitope (FIG. 2)

Induction of apoptosis of WEHI B cells was used as a measure of antigen uptake and presentation. WEHI B cells ($2\times10^4$) where mixed with a peptide p21-35 specific Treg clone (ratio 1/1) and decreasing concentrations of peptide p21-35 (X axis), or the same peptide linked to a minor T epitope from tetanus toxin (p830-844; T-B). After 18 hours, cells were labelled with anti-CD19-PE antibodies (a marker of WEHI cells) and Annexin V-FITC, an apoptosis marker. Samples were then analysed by flow cytometry. Results are representative of the proportion of WEHI cells positive for Annexin V. A 100-fold increase in the capacity to induce apoptosis was observed when peptide p21-35 was linked to a minor T cell epitope, as indicated in FIG. 2.

Example 3: Amino Acid Residues Involved in the Thioredoxin-Like Consensus Sequence are Instrumental for Expression of Regulatory Properties Panel A of FIG. 3 shows the location of the thioredoxin-like sequence motif within peptide p21-35. The CHGS [SEQ ID. NO: 3] sequence is adjacent to the MHC-class II binding cleft. Alanine substitution of residue 21C or residue S24 of the thioredoxin-like C-X(2)-S motif does not impair T cell epitope recognition as measured by the proliferation ($^3$H-thymidine incorporation) of a Treg clone, is indicated in panel B of FIG. 3. Proliferation was carried out using $5\times10^4$ WEHI cells incubated for 1 h at 37° C. with 6 µM of peptide. The cells were then washed and co-cultured for 4 days with $5\times10^4$ T cells. $^3$H-thymidine was added 24 h before the end of the culture. Radioactivity was counted on cells adsorbed on fibre glass filters. Substitution of residues 21 and 24 abrogate the capacity of the Treg clone to lyse antigen-presenting cells in an apoptosis induction assay (see panel C of FIG. 3) carried out as described in Example 2.

Figure 4A:
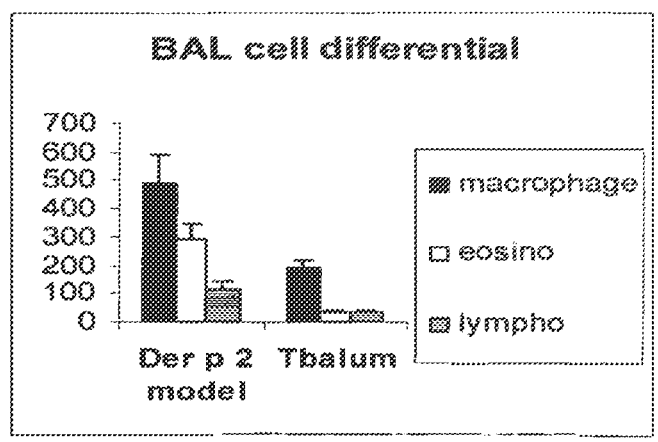
Figures 4B, 4C:
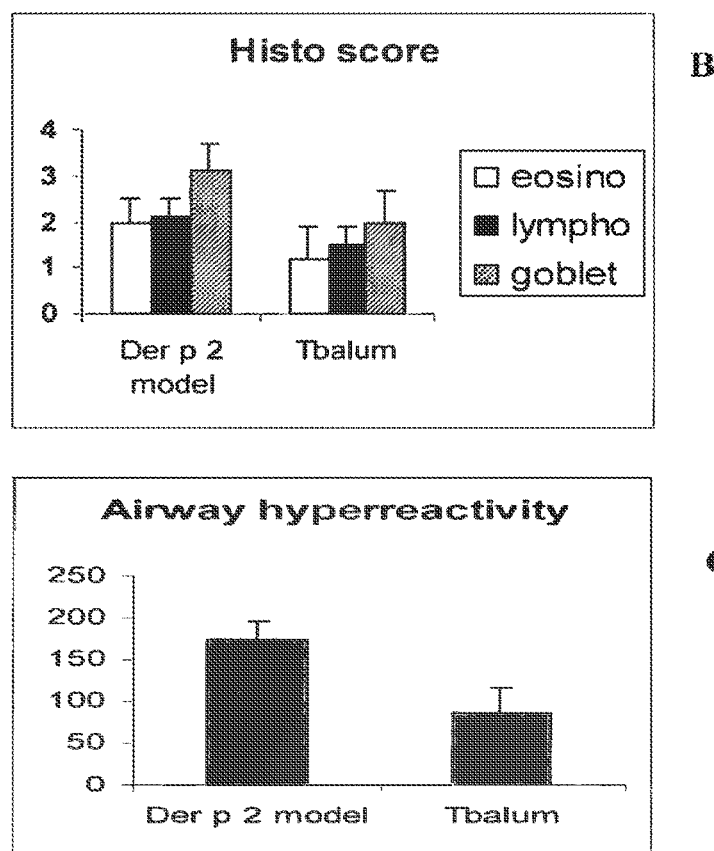

Example 4: Generation of Tregs with Physiological Properties Upon Injection of T-Bb in Mice The capacity of the peptide T-B to prevent Der p 2-induced asthma was evaluated as follows. A group of 8 BALB/c mice (indicated as Tbalum in FIG. 4) received 3 footpath injections (20 µg per injection) carried out at 2-week interval with the T-B peptide adsorbed on alum. Two weeks after the last injection, all mice received IP injections of alum-adsorbed full length rDer p 2 (40 µg per injection) on 3 occasions with a 2-week interval, followed by nasal instillations of rDer p 2 in saline (100 µg rDer p 2 in 50 µl PBS per instillation). The results were evaluated by comparison with a group of mice treated by rDer p 2 (indicated as "Der p 2 model" in FIG. 4) but which did not receive peptide injections. The Figure indicates that pre-immunisation with the peptide significantly reduces BAL cell counts evaluated on cytospins (FIG. 4 panel A), lung histology scores (FIG. 4, panel B) and airway hyperreactivity (FIG. 4 panel C) assessed by reactivity to increased concentrations of methacholine.

Figure 5:
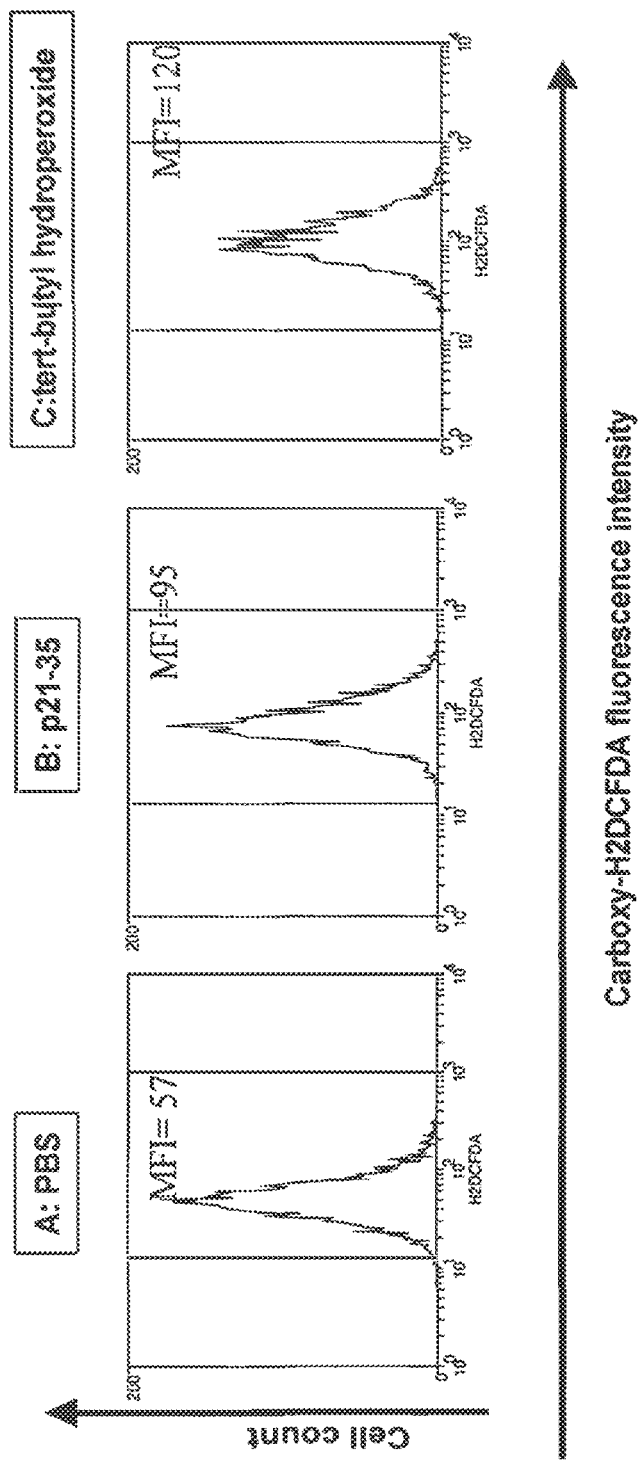

Example 5: Effect of P21-35 on the Oxidative Metabolism of Cognate Treg Cells A Treg clone ($10^5$ cells) specific for p21-35 was incubated for 90 minutes with PBS (FIG. 5, panel A), peptide p21-35 (20 µg/ml in 200 µl PBS; FIG. 5, panel B) or tert-butyl hydroperoxide (100 µM in PBS; FIG. 5, panel C), which is an inducer of Reactive Oxygen Species (ROS). Cells were then labelled for 30 minutes with carboxy-H2DCFDA (12 µM), a fluorogenic marker for ROS in live cells, and then analysed by flow cytometry. The picture shows that peptide p21-35 stimulates the oxidative metabolism of cognate Treg cells and induces a doubling in the fluorescence intensity due to ROS increase.

Figure 6:
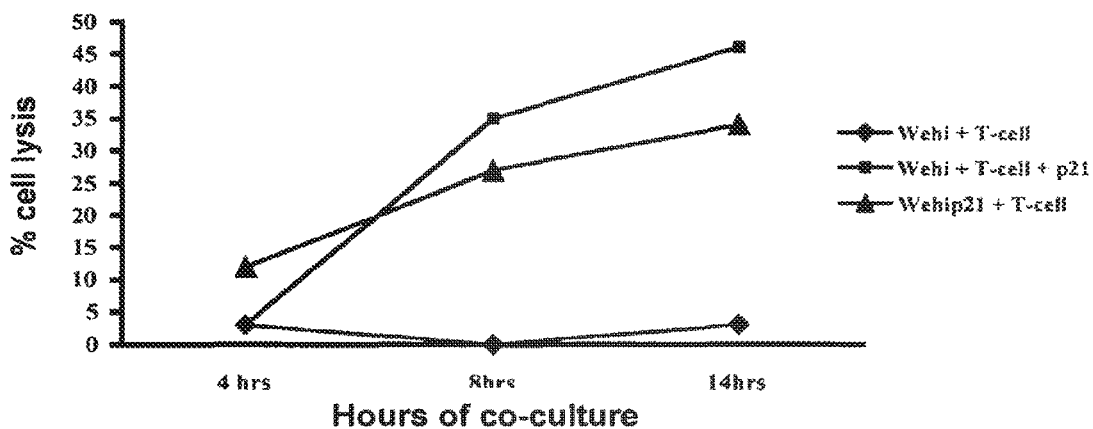

Example 6: TREG Cell Clones Exhibit Cytotoxic Properties on Antigen-Presenting Cells The cytotoxic properties of a Treg line (G121) was tested on the WEHI B cell line used as an antigen-presenting cell. FIG. 6 shows the % of cells lysed over a 14-h period of time in the presence of the cytotoxic cell line alone (WEHI ($10^4$ cells)+T cell ($10^4$ cells)) the T cell line with addition of the p21-35 peptide (WEHI+T cell+p21), or WEHI cells pre-loaded with the p21-35 peptide (WEHIp21+T cell). Lysis of WEHI cells was measured using the JAM assay (a quantitative assay of DNA fragmentation): $10^4$ WEHI cells were pre-incubated with $^3$H-thymidine (4.5 µCu/ml, 1 ml) for 10 h at 37° C. and then washed before co-culture with the Treg line. The release of $^3$H-thymidine in supernatants was taken as a measure of WEHI cell lysis. The data shows that the presence of the peptide is required to activate the T cell line.

Figures 7A, 7B, 7C, 7D:
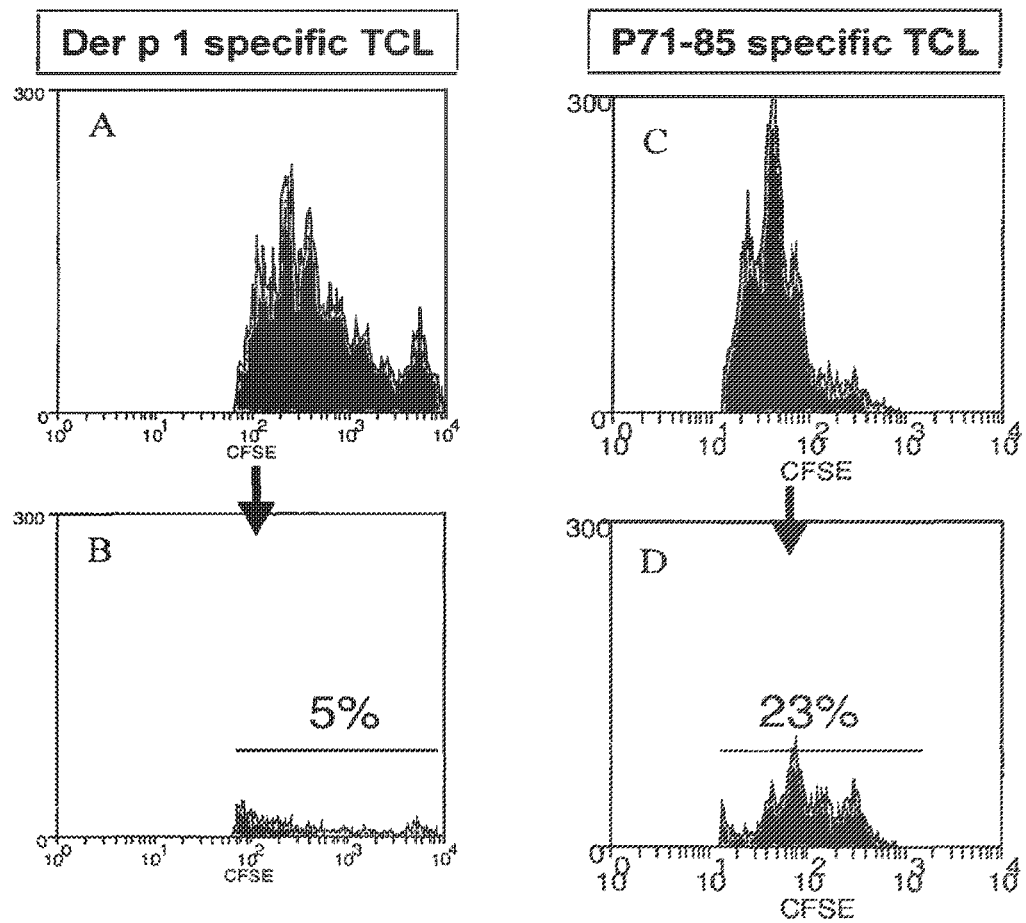

Example 7: Treg Cell Clones Suppress the Activation of T Cells Specific for Another Epitope on the Same Antigen, or Specific for Another Antigen by Cytotoxicity (FIG. 7)

T cell lines (TCL; $10^5$ cells) specific for Der p 1, an allergen unrelated to Der p 2 or specific for an alternative major T cell epitope (p71-85) located on Der p 2 were labelled with CFSE (which is a label for cytoplasmic proteins, making it possible to evaluate the number of cell divisions based on intensity of staining, which reduces to 50% each time the cell divides) (12.5 nanoM) (FIG. 7). The proliferation of such CFSE-labelled Der p 1 specific TCL (Panel A and B) or p71-85 TCL (panel C and D) was measured before (panel A and C) or after (panel B and D) incubation with the cytotoxic Treg clone (ratio 1/1). Antigen-presenting cells were preloaded with both the specific allergen (Der p 1 or Der p 2; 0.5 ml containing 10 µg/ml in each case) and peptide 21-35 (0.5 ml containing 10 µg/ml). After 72 hours of incubation, cells were harvested, stained with propidium iodide and analysed in a flow cytometer. Histograms and percentages in parts B and D of the Figure represent the proportion of residual living CFSE-positive cells (live cells were discriminated by being propidium iodide negative). The Figure shows that the cytotoxic Treg clone specific for peptide 21-35 strongly decreased the proliferation of each of the 2 bystander T cells (CFSE divisions). Most of the CFSE-stained cells became positive for the apoptosis marker propidium iodide, indicating that bystander T cells were killed in the assay.

Example 8: Determination of the Phenotypic Profile of Treg Cells

Figure 8:
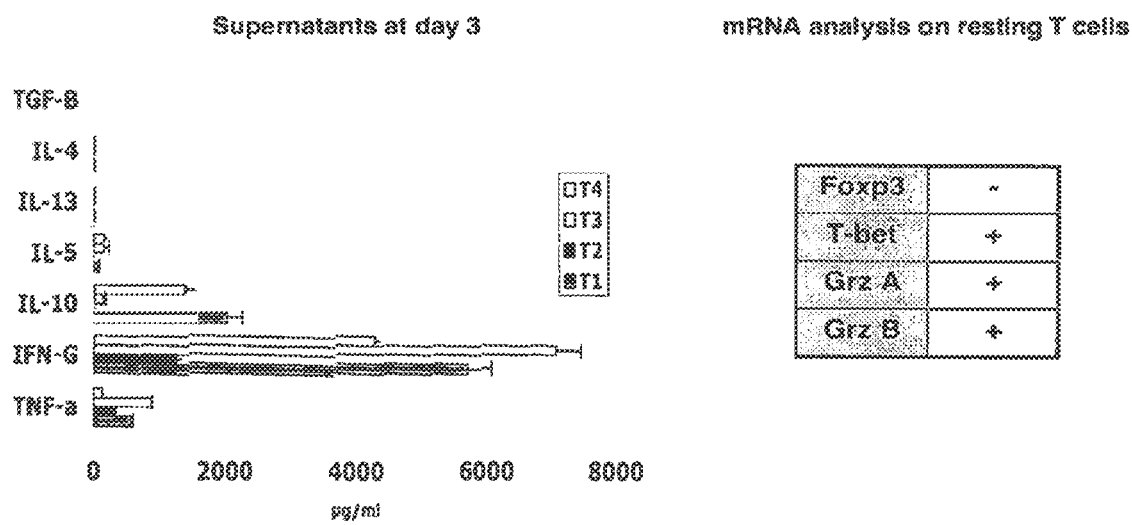

FIG. 8 shows cytokine production of four p21-35 specific Treg clones derived from mice treated with the peptide T-B composition as in Example 4 (left panel). Supernatants of cell culture were analysed for cytokine content after four days of stimulation with antigen-presenting cells (irradiated splenocytes from naïve mice, $10^5$ cells) and peptide p21-35 (2 µg/ml, 200 µl). Treg clones mainly produced lFN-γ (IFN-G) and only trace amounts of TNF-α (TNF-a) and IL-10. The right panel shows the m-RNA analysis of such Treg cells. Transcripts for transcription repressor Foxp3 were not detected, but T-bet, Granzyme A and Granzyme B show strong transcription levels.

Figure 9:
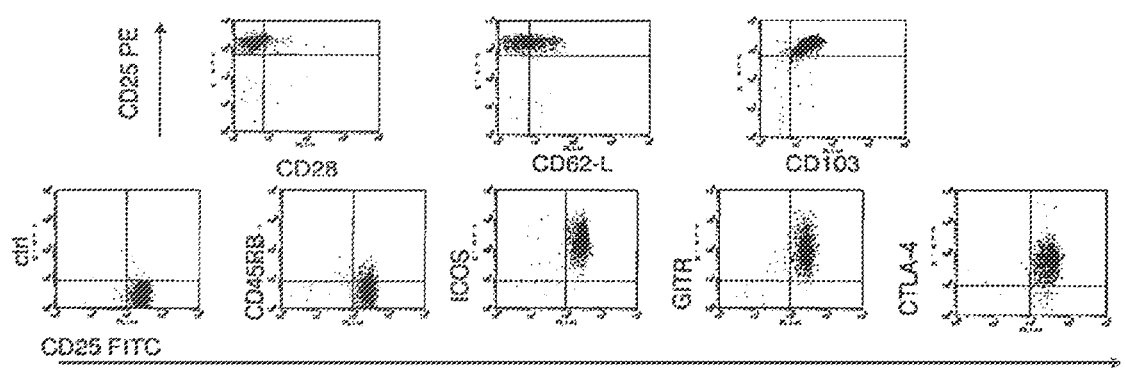

FIG. 9 shows the expression levels of various genes in a 21-35 peptide specific T cell clone at rest by fluorescence-activated cell sorting (Facs). In Table 4, the mean fluorescent intensity is provided of four different clones (T1 to T4) ($2\times10^5$ cells). High levels of CD25, ICOS, GITR, CD103 and intracellular CTLA-4 were observed. CD28 was not or poorly expressed. CD62-L and CD45RB were expressed at low levels. All antibodies were from Becton-Dickinson (NJ, USA).

TABLE 4

| mean fluorescence of fluorescent antibody labelled Treg clones | | | | | | |
|---|---|---|---|---|---|---|
| CD28 | CD62L | CD103 | CD45RB | ICOS | GITR | CTLA-4 |
| T1 | 5 | 36 | 21 | 6 | 251 | 127 | 98 |
| T2 | 12 | 27 | 25 | 10 | 245 | 150 | 110 |
| T3 | 4 | 39 | 27 | 6 | 263 | 110 | 92 |
| T4 | 4 | 36 | 14 | 7 | 253 | 129 | 87 |

Figure 10:
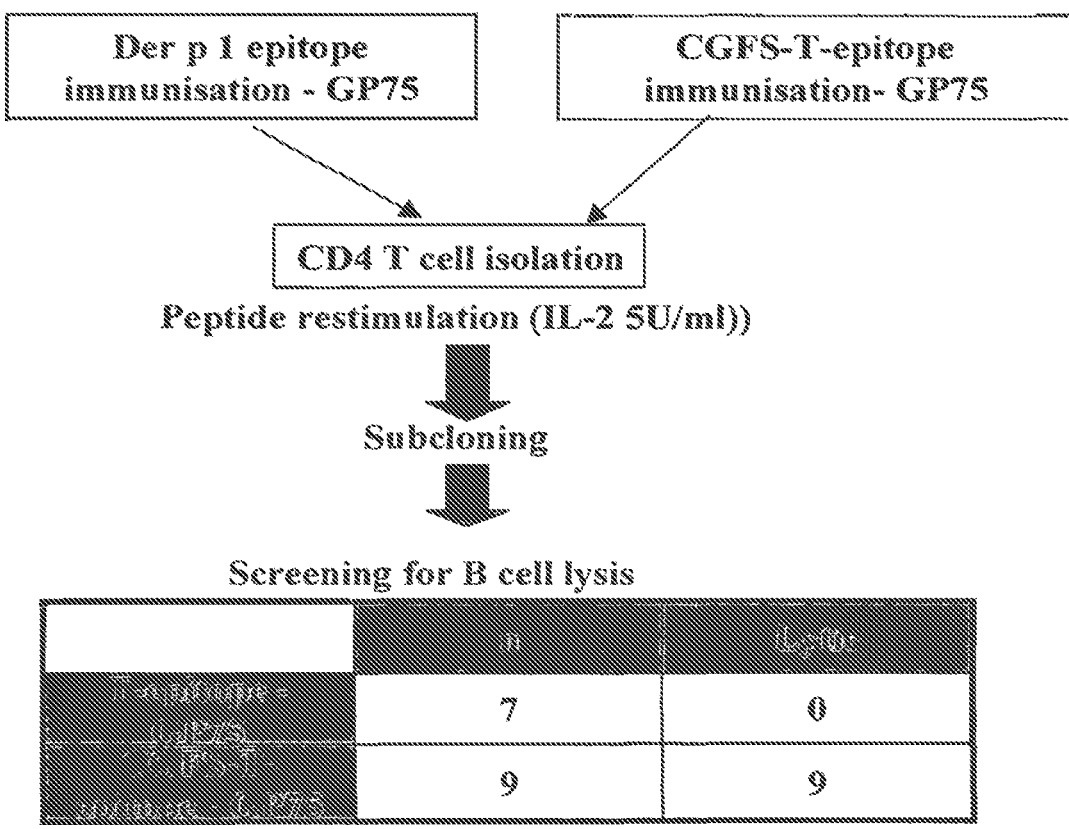

Example 9: Treg Cells with Cytotoxic Properties are Elicited by Immunisation with a Peptide Made of a Dominant T Cell Epitope of the Allergen Der P 1 Linked to a Glutaredoxin-Like Consensus Sequence (FIG. 10)

A dominant T cell epitope of the allergen Der p 1 recognised by BALBfc mice SNYCQIYPPNANKIR p114-128 [SEQ ID. NO: 5] was synthesised in line with the sequence CGFS (motif sequence [SEQ ID. NO: 6]), which carries a glutaredoxin-like consensus sequence from E. coli k12. The latter was added at the amino-terminal end of the T cell epitope (taking s114 as P1).

The full peptide has the sequence CGFSSNYCQIYPPNANKIR [SEQ ID, NO: 7]. The sequence containing the Der p 1 T cell epitope without the glutaredoxin-like consensus sequence [SEQ ID. NO: 5] was used as a control. Both peptides were joined by a linker sequence SGGSGGSGG [SEQ ID. NO: 8] at the amino-terminal end of the sequence to the amino terminal end of the sequence IITIAVVAALLLVAAIFGVASCLI RSRST-KNEANQPLLTDS [SEQ ID. NO: 9], corresponding to the transmembrane domain and the truncated cytosolic tail of the gp75 protein, in order to target the T cell epitope to the late endosome (the dileucine-based motif is underlined).

The full sequence of the peptide comprising targeting sequence, linker, motif and epitope sequence is:

[SEQ ID. NO: 10]
CGFS SNYCQIYPPNANKIR SGGSGGSGG

IITIAVVAALLLVAAIFGVASCLIRSRSTKNEANQPLLTDS, whereas the control peptide without the sequence CGFS [SEQ ID. NO: 6] has the sequence:

[SEQ ID. NO: 11]
SNYCQIYPPNANKIR SGGSGGSGG

IITIAVVAALLLVAAIFGVASCLIRSRSTKNEANQPLLTDS

Groups of BALB/c mice were immunised subcutaneously (20 µg) with the experimental peptide [SEQ ID. NO: 10] or the control peptide [SEQ ID, NO: 11] adsorbed onto aluminium hydroxide. Three injections were performed at 2-week intervals. Ten days after the last immunisation, mice were sacrificed and CD4+ T cells prepared from the spleen using magnetic beads, CD4+ T cells (2×10⁶ cells) were then stimulated in vitro by the Der p 1 T cell epitope (20 µg) presented by adherent spleen cells serving as antigen-presenting cells.

Ten days after stimulation the number of specific T cell lines obtained in each group was calculated by limiting dilution analysis. Each cell line was evaluated for its capacity to lyse WEHI cells, a B cell line selected for its efficacy in antigen-presentation by MHC class-II determinants, as described in Example 6. Only cells obtained from animals immunised with the peptide containing the glutaredoxin consensus sequence had acquired the capacity to lyse WEHI cells, and lysis occurs only in the presence of the cognate Der p 1 T cell epitope.

FIG. 10 shows that T cell clones with Treg properties could only be derived from mice that received the construct made of the Der p 1 epitope linked to a glutaredoxin-like redox motif and gp75, but not from mice that received the control peptide. All T cell clones obtained after treatment with the construct and re-stimulated in vitro were cytotoxic.

Example 10: Use of a Dominant T Cell Epitope of MOG Protein in an In Vivo Model for Multiple Sclerosis Multiple sclerosis can be induced in experimental models by immunisation with the Myelin Oligodendrocyte Glycoprotein (MOG) peptide VGWYRSPFSRVVHLYR [SEQ ID. NO: 12], which corresponds to amino acid residues 37-52 of the MOG protein. This peptide contains a dominant T cell epitope. The P1 position, i.e, the first amino acid anchored into the MHC class II groove is Y40 (the P1-P9 sequence is underlined). The 3 amino acids of the amino terminal end of the peptide are replaced by the sequence CGPS [SEQ ID, NO: 13], which corresponds to the human thioredoxin sequence, residues 21 to 24), resulting in the peptide CGPSYRSPFSRVVHLYR [SEQ ID. NO: 14]. The experimental peptide [SEQ ID. NO: 14] and the control peptide [SEQ ID. NO: 12] are joined by the linker sequence SGGSGGSGG [SEQ ID. NO: 8] at the amino-terminal end of the sequence VSVSAVTLGLGLIIFSLGVIS WRRAGHSSYTPLPGSNYSEGWHIS [SEQ ID. NO: 15] corresponding to the transmembrane domain and the cytosolic tail of the HLA-DMR protein, in order to target the T cell epitope to the late endosome (the tyrosine-based peptide motif is underlined).

The sequences of the targeted peptide are:

[SEQ ID. NO: 16]
VSVSAVTLGLGLIIFSLGVISWRRAGHSSYTPLPGSNYSEGWHIS

SGGSGGSGG CGPS YRSPFSRVVHLYR and

[SEQ ID NO: 17]
VSVSAVTLGLGLIIFSLGVISWRRAGHSSYTPLPGSNYSEGWHIS

SGGSGGSGG YRSPFSRVVHLYR

A group of C57BL/6 mice is adoptively transferred with a CD4+ MOG-specific effector T cell clone following a protocol meant to induce a multiple sclerosis-like syndrome. This involves administration of the MOG peptide in complete Freund's adjuvant and 2 injections of Pertussis toxin. This protocol elicits an expansion of the effector T cell clone, which results in the development of signs compatible with multiple sclerosis within 12 days after the MOG peptide administration.

A second group of C57BL/6 mice is first adoptively transferred with a MOG-specific regulatory T cell clone (obtained using the peptides [SEQ ID. NO: 16 and 17] described above), followed after 1 day by the full protocol of disease induction.

It is observed that the clinical score developed by mice pre-treated with a cytolytic T cell clone is significantly reduced as compared to mice receiving only the effector T cell clone.

Methods and Materials

Mice. Six to eight-week-old BALB/c mice were obtained from in-house facilities. The in vivo studies were approved by the University of Leuven's Ethical Committee.

Reagents. Peptides derived from Dermatophagoides pteronyssinus group 2 allergen (Der p 2) Der p 1 and tetanus toxoid were synthesised (purity, >85%). Sequences are: p21-35, CHGSEPCIIHRGKPF [SEQ ID. NO: 2]; p114-128 (amino-acids 114-128 from Der p 1), SNYCQIYPPNANKIR [SEQ ID. NO: 5]; p830 (amino-acids 830-844 from tetanus toxoid), QYIKANSKFIGITEL [SEQ ID. NO: 18]; mp21-35 QYIKANSKFIGITELGGCHGSEPCIIHRGKPF [SEQ ID. NO: 19]; mp21-35Asn QYIKANSKFIGITEL-GGCHGSEPCNIHRGKPF [SEQ ID. NO: 20]. Recombinant full-length Der p 2 was produced in Pichia pastoris.

Allergen sensitisation. Animals were sensitised on day 1, 14 and 28 by an i.p. injection of 40 µg recombinant allergen absorbed on 6 mg AL(OH)₃. On day 43, 44, and 45, mice were exposed to 100 µg allergen in 50 µl saline by intranasal instillation, followed by a first measurement of pulmonary function by whole body plethysmograph. A second series of nasal instillations was performed on day 50, 51 and 52 followed by assessment of pulmonary function by whole body plethysmograph.

Cell purification. Splenic CD4 T cells were obtained after peptide immunisation. After Ficoll density gradient purification (Nycomed Pharma), they were enriched by negative selection using the CD4 cell Isolation Kit (Miltenyi Biotec) and LS separation columns. Splenic dentritic cells were positively selected using CD11c Microbeads (Miltenyi Biotec) on LS separation columns. They were stimulated with 5 µg/ml LPS (Sigma) for 5 hours, then washed and kept for 18 hours in a CO2 incubator; live cells were recovered by eliminating dead and apoptotic cells with annexin V microbeads on LS columns and MidiMacs (all from Miltenyi Biotec).

B lymphocytes were prepared from spleen cells of naïve BALB/c mice by positive selection using CD19 microbeads (Miltenyi Biotec). As antigen presenting cells, splenocytes were depleted from T cells by CD90 microbeads (Miltenyi Biotec) on LD depletion columns. In some assays, splenic adherent cells were prepared by incubating splenocytes for 2 h at 37° C. in culture medium. Non-adherent cells were removed and the remaining cells were recovered for assays.

Lung lymphocytes were prepared by collagenase (Sigma) digestion and Percoll (Pharmacia) centrifugation as previously described (Abraham et al. (1990) *J. Immunol.* 144, 2117-2122).

Cell culture. Dendritic cells, T cells and B cells were cultured in RPMI 1640 medium containing 5% FCS, 50 µM 2-ME, 200 µg/ml Gentamicin (Invitrogen). Wehi 231 cells were purchased from the European collection of cell cultures (ECACC).

The effector T cell clone G221N is specific for peptide p21-35. G121, R3TB7, T1 and T3 identify cytolitic T cell clones tested in this study (in Example 11).

Peptide processing assays. G221N, an effector T cell clone specific for peptide p21-35 was tested in a proliferation assay were splenic adherent cells were used as APC. They were pretreated with either 0.2 µM leupeptin, 0.1 mM chloroquine, 60 µM colchicin or left untreated for 30 min. After 3 washes with PBS, APC were loaded for 1 hour with peptide p21-35, mp21-35 or Der p 2 at 37° C. They were then washed twice with culture medium and added to the G221N clone ($10^5$ each) for 72 h. To block endocytosis APC were also treated with NaN3/deoxyglucose (2 mg/ml, 50 mM, respectively) during all the incubation time with the peptides followed by 3 washes with cold PBS. Proliferation was assayed by the addition of 1 µCi/well of [$^3$H]thymidine (ICN) during the last 18 h. Cells were harvested and incorporated isotope counted (cpm). Data were expressed as stimulation index calculated by dividing the cpm obtained for G221N T cells stimulated with peptide loaded APC by the value obtained with unloaded APC.

Derivatisation of regulatory T cell clones. BALB/c mice were immunised by 3 footpad injections of 20 µg/ml peptide mp21-35Asn in alum at 2 weeks intervals. Ten days after the last injection, spleen CD4+ T cells were stimulated with T cell depleted splenocytes from naïve mice in the presence of peptide mp21-35Asn. After 10 days, cells were restimulated in the same conditions but with 10 U/ml mouse II-2 (Roche). After the fifth restimulation, T cells were subcloned in the presence of 10 U/ml IL-2 by limiting dilution. The subsequent specific stimulations were carried out in the presence of 20 U/ml mouse IL-2. The G121 T cell line was derived as previously described (Janssens et al. (2003) *J. Immunol.* 171, 4604-4612).

FACS analysis. A FACSCalibur (Becton Dickinson) was used for analytical flow cytometry and data were analysed with CellQuest software. Ten days after the last restimulation, T cells were stained with antibodies to CD25, CD28, CD62-L, CD103, CD45RB, ICOS, CTLA-4, and CD11c, (Pharmingen), GITR, Foxp3, Granzyme-B, T-bet(4B10), perforin, CD127, and Vb8.1 TCR, (eBioscience).

Bystander suppression assays. Target CD4+CD25− T cells and T helper clones were labelled with 125nM CFSE (Molecular Probes) for 15 minutes in PBS at 37° C. The reaction was stopped by washing the cells with PBS containing 30% FBS. These cells ($3\times10^5$) were cocultured with $10^5$ cytotoxic CD4+ T cell clones and cell depleted splenocytes with 1 µg/ml anti-CD3 antibody (eBioscience), For suppression of T helper clones, $10^5$ cells were co-cultured with the same number of cytotoxic cells and T cell depleted splenocytes. After 48 h or 72 hours, cells were collected and analysed by flow cytometry.

For some cultures, blocking antibodies against FAS-L, GITR, LAG-3 were used at 10 µg/ml (eBioscience). Transwell assays were performed in 24 well plates (Becton Dickinson).

Apoptosis detection. Annexin V-FITC or -PE were used to detect cell death in B cells, dendritic cells and T cells (Annexin V detection kit, BD Biosciences). In some experiments, apoptosis was measured by intracellular detection of activated caspase-3 with FITC- or PE-labelled antibodies (Pharmingen) or by nuclear labelling with a propidium iodide (PI) staining solution (Pharmingen) according to manufacturer instructions.

For inhibition of GZ-B activity, Z-AAD-CMK (Calbiochem) or 3,4-dichloroiso-coumarin (DCIC) (SIGMA) were added at indicated concentrations during all the co-culture period.

Cytokine detection. One million Treg cells were restimulated with 3 million irradiated T cell-depleted splenocytes for 72 hours. Supernatants were assessed for the presence of different cytokines. IL-10 and IL-13 were evaluated using the OptElA mouse Elisa kit (BD Biosciences). TGF-13 and IL-13 were evaluated with the DuoSet anti-mouse TGF-b1 or DuoSet anti-mouse IL-13 assay kits, respectively (R&D Systems). II-2, IL-4, IL-5, IFN-γ and TNF-α production were analysed by flow cytometry using the Th1/Th2 Cytokine CBA kit (BD Biosciences).

For polyclonal CD4+ cells stimulation, $10^6$ cells were stimulated with $5\times10^5$ irradiated T cell depleted splenocytes (from naïve mice) and 10 µg/ml Der p 2 for 72 h.

Polyclonal CD4+ cell proliferation. $10^5$ Splenic CD4 cells from peptide treated mice were stimulated with $10^5$ T cell depleted splenocytes and 10 µg/ml mp21-35, 5 µg/ml peptide p830 or 10 µg/ml Der p 2. ($^3$H)-thymidine incorporation was assayed as already described. Results are shown as average isotope counting (cpm)±s.e.m. from 6 mice individually tested in triplicates.

Airway hyper-reactivity. Airway hyper-reactivity (AHR) was measured in unrestrained mice using a whole body plethysmograph (EMKA) according to published methods (Hamelmann et al. (1997) *Am. J. Resp. Crit. Care Med.* 156, 766-775). The peak enhanced pause (PenH) was used as a parameter for bronchoconstriction. Animals were exposed for 1 minute to increasing doses of aerosolised methacholine (from 10 to 100 mg/ml), followed by 3 minutes rest during which breathing parameters were evaluated. PenH values were expressed as means of measurements carried out every 30 seconds over a 3-minute period after each methacholine exposure. Lung compliance were measured with FlexiVent system (Scireq).

Bronchioalveolar lavage fluid collection (BALF). Three days after methacholine challenge, mice were sacrificed, the trachea was isolated and a canula was inserted. BALF was collected by washing with 1 ml of saline containing 5% BSA (used for cytokine detection) and then followed by 2×1 ml of saline. Cell count was established. Cytospins were prepared by centrifugation at 1400 rpm for 6 min and stained (Diff-Quik method). One hundred cells were counted in 3 different fields for cell identification.

Lung Histology. Lungs were fixed with 4% formaldehyde, dehydrated and embedded in paraffin for sectioning (7 μm-thick slides) and stained with hematoxylin/eosin. Eosinophils were detected by May-Grünwald Giemsa staining. Goblet cells in airway mucosa were identified by the periodic acid-Schiff reaction (PAS). PAS positive cells were counted and expressed as percentage of total epithelial cells. For each mouse, 5 fields were examined from each lung section, from the central bronchi as well from small bronchi. The density of eosinophils and lymphocytes infiltration was graded as follow: absent: 0; light but not systematic: 1; light: 2; light to medium: 3; medium: 4; medium to high: 5; high: 6.

All slides were examined by two persons, including a pathologist who was unaware of the groups to which mice belonged.

For analysis of transferred T cells, lungs were fixed with paraformaldehyde, cryoprotected with 20% sucrose overnight and snap frozen in OCT media. Cryostat sections (9 μm) were cut, fixed in acetone and mounted with antifade reagent (ProLong Gold; Invitrogen) and analysed with confocal microscopy. Analysis was performed on a Zeiss Axioplan2 connected to a 3CCD video camera (DXC-930P, Sony), and KS300 software (Zeiss).

Targetted expression of peptide in B lymphocytes. The onco-retroviral pMND-SN vector was obtained from Dr. D. Kohn, USC. A fusion construct containing p21-35 (amino acids 21 to 35 of Der p 2) and the carboxy-terminal end of gp75 (amino acids 488 to 539) connected with a linker, Ser-Gly-Gly-Ser-Gly-Gly-Ser-Gly-Gly [SEQ ID. NO: 8], was made by PCR and cloned into pMND vector. The resulting vector pMND-p21gp75 was used in conjuction with vectors coding for viral proteins to transiently transfect 293T cells and onco-retroviral producer cells were obtained as previously described (Janssens W. et al., *Human gene therapy* 14, 263-276 (2003)). Splenic B cells preactivated for 24 hours with 50 μg/ml bacterial LPS were cocultured with filtered viral vector-containing supernatant in the presence of polybrene (6 μg/ml) and LPS (50 pg/ml). B cells were then washed extensively before adoptive transfer to naïve BALB/c mice.

Analysis of mRNA. Polymerase chain reaction (PCR) and reverse transcriptase PCR (RT-PCR) were performed as previously described (Janssens W. et at (2003), *Human gene therapy* 14, 263-276. For T cells, $10^6$ cells were analysed on day 12 after restimulation. Primer sequences were: Granzyme A, (forward) 5' ctctggtccccggggccatc 3' [SEQ ID. NO: 21] and (reverse) 5' tatgtagtgagccccaagaa 3' [SEQ ID. NO: 22]; for Granzyme B, (forward) 5' ctccacgtgctttcaccaaa 3' [SEQ ID. NO: 23] and (reverse) 5' ggaaaatagtacagagaggca 3° [SEQ ID. NO: 24]; for β-actin, (forward) 5' cattgtgatggactccggagacgg 3' [SEQ ID. NO: 25] and (reverse) 5' catctcctgctcgaagtctagagc 3' [SEQ ID. NO: 26]. The annealing temperature was 55° C. for 27 cycles.

Detection of transduced B cells in vivo. Mice that received pMND-p21gp75 transduced B cells followed by T cell clone transfer were sacrificed and splenic B cells were purified with CD19 microbeads (Miltenyi Biotec). Five pg total RNA was reverse transcribed for the preparation of cDNA. PCR was carried out on cDNA using retroviral vector-specific primers, (forward) 5' ccctttatccagccctcactc 3' [SEQ ID. NO: 27] and (reverse) 5' cctggggactttccacaccc 3' [SEQ ID. NO: 28]. Annealing temperature was 56° C. for 28 cycles.

Statistical analysis. Non-parametric assays were used for evaluating differences between means (Mann-Whitney U test). For assessing airway hyperreactivity, the area under the curve was calculated and differences evaluated by the Mann-Whitney U test.

Example 11: In Vivo-Induced Cytolytic CD4+CD25+ Regulatory T Cells Prevent and Suppress Experimental Asthma. Elicitation of Antigen-Specific Regulatory T Cells In Vivo A first cytolytic CD4+CD25+ T cell clone (G121) was obtained from mice immunised with the synthetic peptide p21-35, encompassing a major T cell epitope of the allergen Der p 2. The frequency of such cytolytic T cells was extremely low as compared to that of CD4+ effector cells of the same specificity. Attempts to obtain T cells with the same properties using alternative adjuvants such as alum were unsuccessful.

Figure 11A:
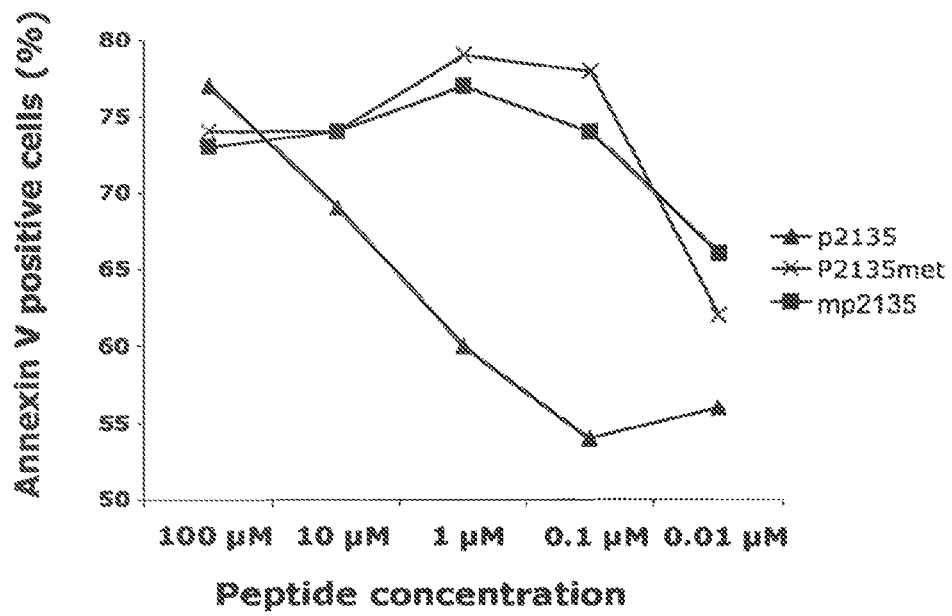

This could be due to inefficient peptide presentation due for example to rapid degradation and/or inefficient late endosome uptake. The in vitro capacity of various forms of peptide was tested to induce apoptosis of a B cell line (Wehi cells) used as antigen-presenting cell (APC) by the G121 regulatory T cell clone. Methylation of the two cysteines may enhance the stability of the peptide (p21-35met). Alternatively, coupling p21-35 to a peptide carrying a known subdominant T cell epitope could increase late endosome uptake. In the BALB/c mouse, the sequence encompassing amino-acid residues 830 to 844 of tetanus toxoid represents such a minor epitope (QYIKANSKFIGITEL, [SEQ ID. NO: 18]). A synthetic peptide covering amino acids 830-844 of tetanus toxoid, linked by two glycines to p21-35 was therefore produced (QYIKANSKFIGITELGGCHGSEPC-NIHRGKPF, [SEQ ID. NO: 20], and for stability reasons, the two cysteines were also methylated (modified peptide, mp21-35). mp21-35 was 100-fold more efficient in inducing Wehi cell apoptosis in the presence of the G121 Treg, as compared to p21-35 (FIG. 11a). Methylation of the 2 cysteine residues of p21-35 (p21-35met) also increased MHC class II presentation, and this stabilised peptide was as efficient as mp21-35. A control peptide made by reversing the order of the two components of mp21-35 was inefficient at inducing WEHI cell apoptosis.

Figure 11B:
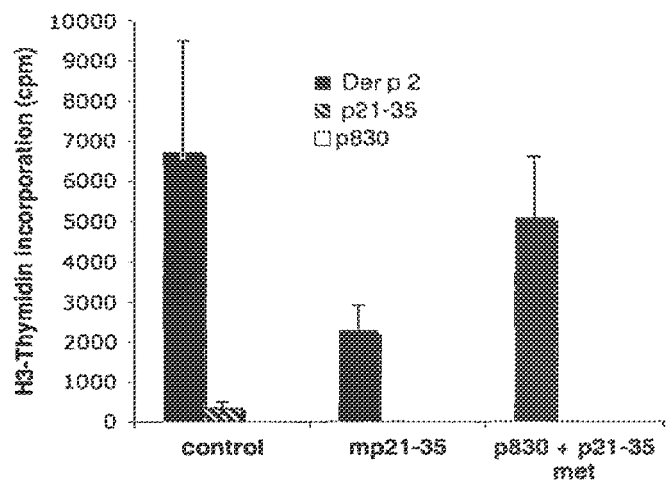
Figure 11C:
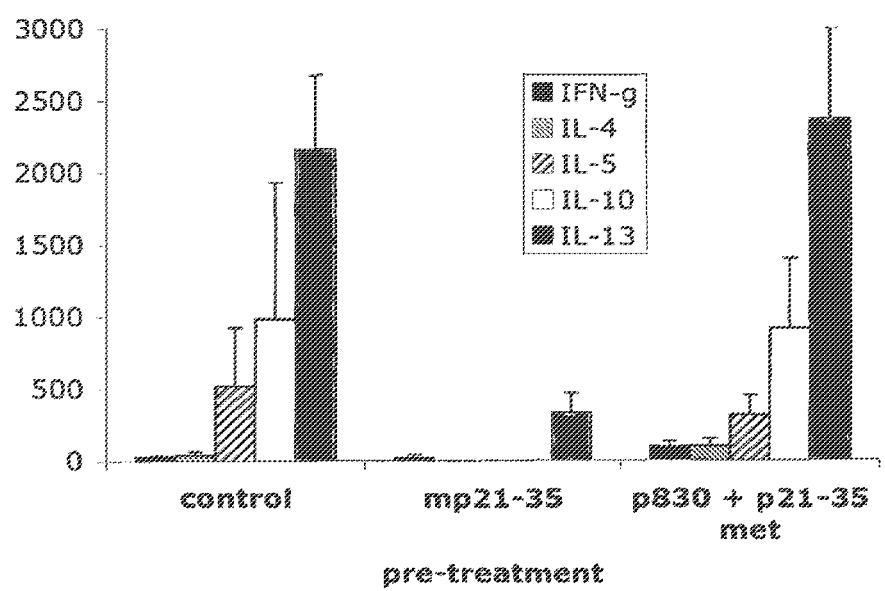

The methylated form of p21-35 (p21-35met) or the coupled variant (mp21-35) were tested for efficient in vivo elicitation of cytolytic T cells. BALB/c mice were immunised with Der p 2 in alum. in vitro restimulation of spleen CD4+ T cells resulted in robust proliferation when Der p 2 was used for stimulation but little response to p21-35 presentation (FIG. 11b: saline control group). Subsequently, the capacity of mp21-35 to prevent CD4+ T cell proliferation by pre-immunisation of BALB/c mice was tested with either mp21-35 or a mixture of p830-844 and p21-35met, namely the two peptide components of mp21-35. This was followed by IP administration of Der p 2 in alum, as above. A significant reduction of Der p 2-induced proliferation was observed only when mp21-35 was used for pre-immunisation (FIG. 11b). The production of cytokines made by CD4+ spleen cells stimulated with Der p 2 was identical in the control group and in the group pre-immunised with the two separate peptide components (FIG. 11c), showing a Th2-like response. In the group pre-treated with mp21-35, cytokine production was reduced to undetectable concentrations.

Figure 11D:
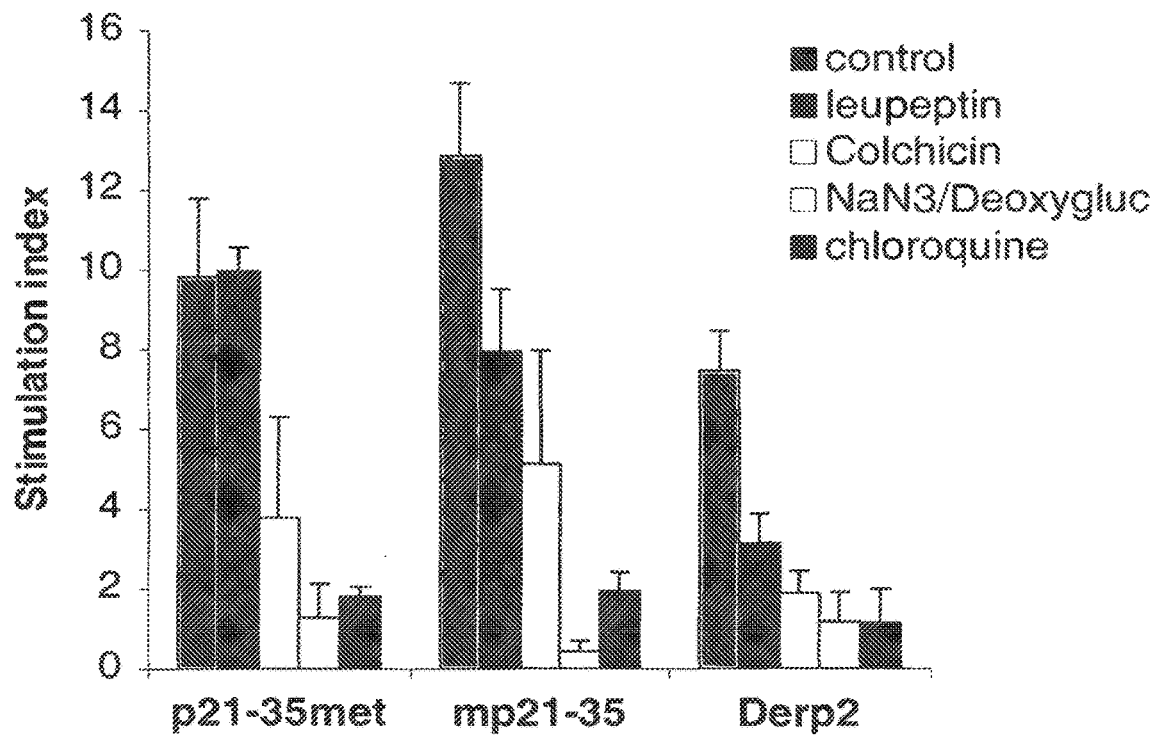

Noteworthy, in vitro stimulation of CD4+ splenocytes obtained from mice pre-treated with either mp21-35 or the mixture of peptides elicited no proliferation to p830-844 (FIG. 11b), or cytokine production, indicating that the tetanus toxoid-derived peptide did not interfere with the generation of Tregs.

mp21-35 had to be processed for efficient presentation, as shown by assessing activation of a p21-35 effector T cell (G221N) in the presence of various inhibitors (FIG. 11d). This shows that p21-35met, mp21-35 and Der p 2 required internalisation into antigen-presenting cells (inhibited by NaN3/deoxyglucose), fusion with and acidification of the late endosomes (inhibited by colchicine and chloroquine, respectively). Peptide processing was not required for p21-35met, as shown by absence of inhibition by addition of leupeptin, a serine/cysteine protease inhibitor, reflecting the capacity of MHC class II molecules to accommodate sequences of up to 15 amino acids.

Taken together, these data indicate that mp21-35 was efficiently processed in vivo, by contrast to a mixture of its two components, and that pre-immunisation with mp21-35 prevented allergen-specific T cell activation. Based on findings showing that regulation can be more readily achieved with analogues of T cell epitopes, the capacity of various single amino acid p21-35 mutants to elicit CD4+ T cell after IP immunisation in alum was determined. In particular, a mutant peptide with an Ile28Asn mutation, a position known to correspond to the P4 MHC class II anchoring residue, showed only slightly reduced capacity to induce T cell proliferation. The mutated form of mp21-35 (mp21-35Asn) was therefore use in the remainder of the experiments in this Example.

Derivatisation and Phenotypic Characterisation of Treg Clones

T cell clones were derived for phenotypic analysis from the spleen of mice injected with either mp21-35Asn in alum, mp21-35Asn in CFA/IFA (complete or incomplete Freund adjuvant), Der p 2 or saline as a control. A total of 17 clones were obtained, which expansion was fully dependent of addition of IL-2. These clones were maintained at rest for 10 days before assessing expression of CD25. Positive clones were then screened for their capacity to induce apoptosis of p21-35-loaded Wehi cells using annexin V binding as read-out. All CD4+CD25+ T cell clones (8/8) derived from mice immunised with mp21-35Asn in alum were shown to be cytolytic, while no such clones were obtained with mp21-35Asn in CFA/IFA (0/5) or from mice immunised with Der p 2 (0/4). Interestingly, a small number of CD4+ effector T cells were obtained from non-immunised mice (see below) but none were cytolytic.

Figure 12A:
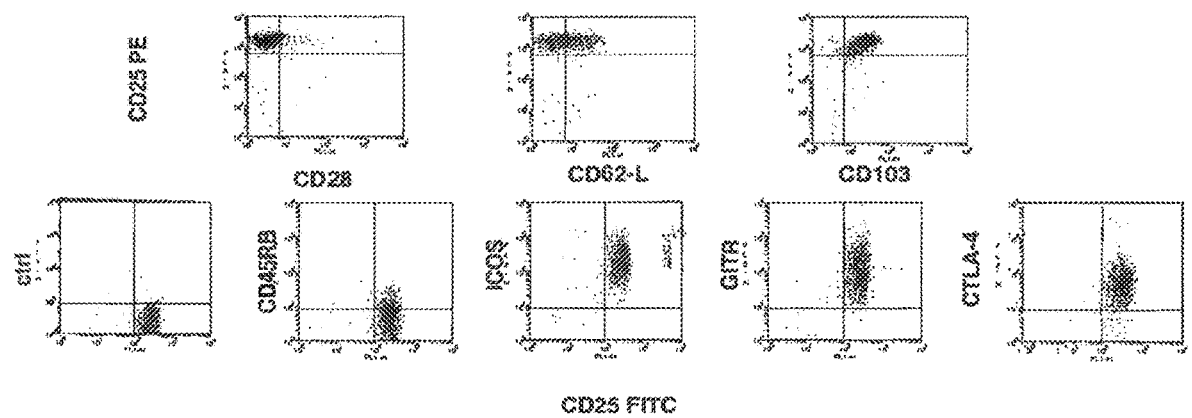

The phenotype of cytolytic Tregs was characterised. Similar results were obtained for a total of 15 clones obtained from separate immunisations. Representative Facs results for surface markers are shown in FIG. 12a (one representative clone) and in Table 5 (4 clones), indicating homogenous expression levels.

TABLE 5

Presence of surface markers on 4 cytolytic clones obtained with peptide mp21-35Asn (expressed as MFI)

| | CD28 | CD26L | CD103 | CD45RB | ICOS | GITR | CTLA-4 |
|---|---|---|---|---|---|---|---|
| T1 | 5 | 36 | 21 | 6 | 251 | 127 | 96 |
| T2 | 12 | 27 | 25 | 10 | 245 | 150 | 110 |

TABLE 5-continued

Presence of surface markers on 4 cytolytic clones obtained with peptide mp21-35Asn (expressed as MFI)

| | CD28 | CD26L | CD103 | CD45RB | ICOS | GITR | CTLA-4 |
|---|---|---|---|---|---|---|---|
| T3 | 4 | 39 | 27 | 6 | 263 | 110 | 92 |
| T4 | 4 | 36 | 14 | 7 | 253 | 129 | 87 |

Figure 12B:
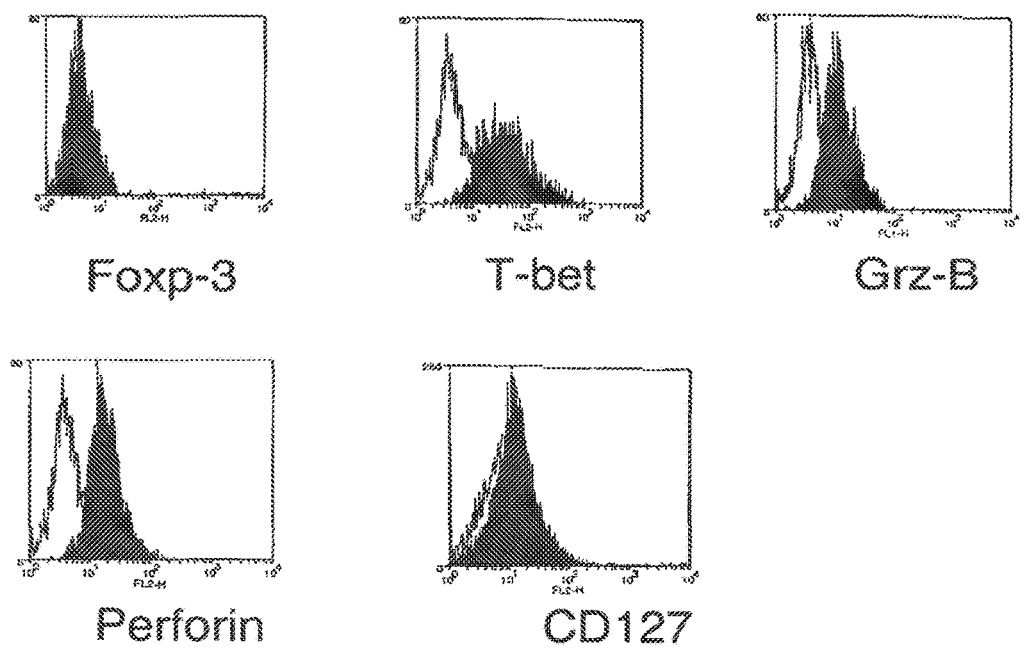
Figure 12C:
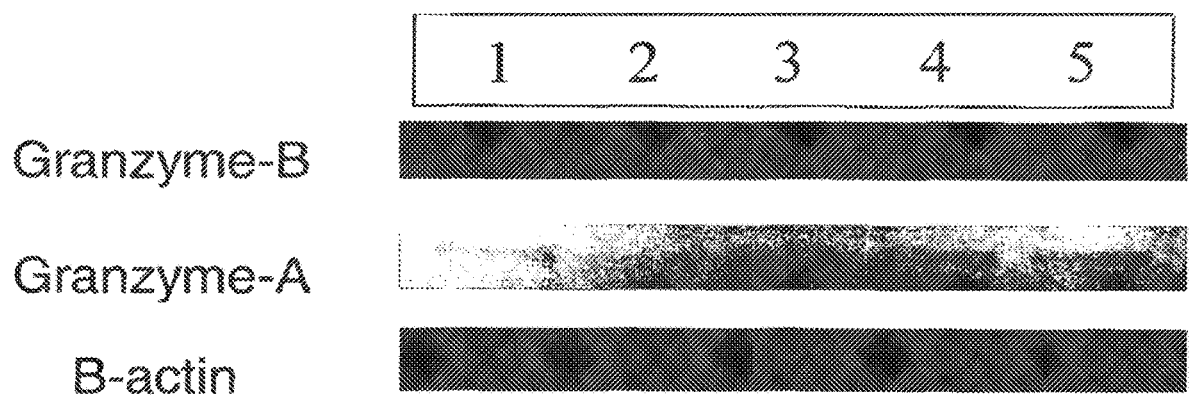
Figure 12D:
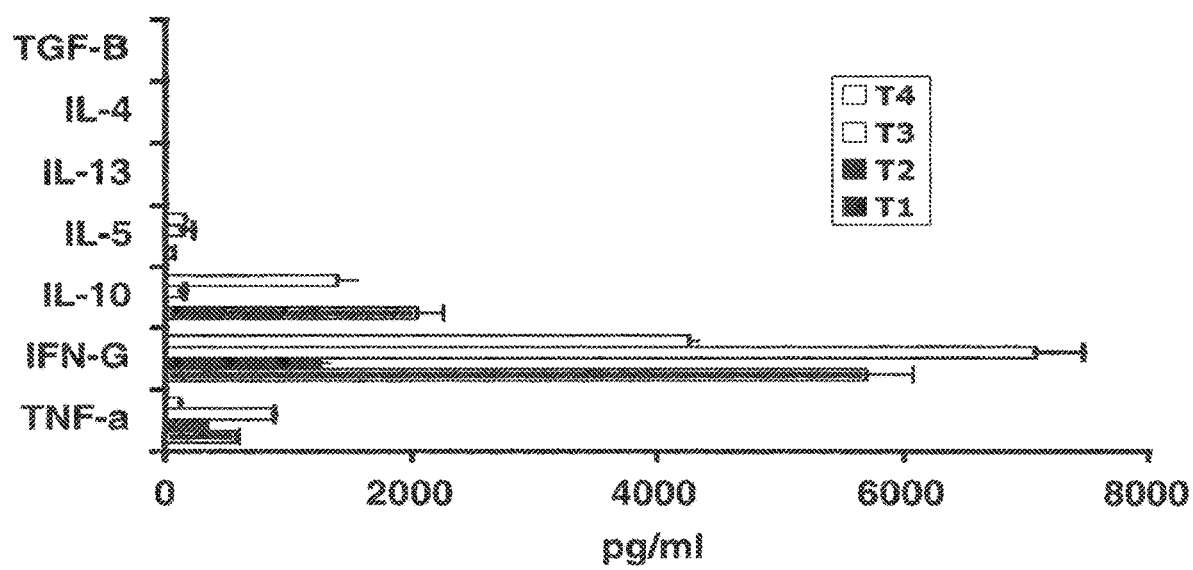

All clones expressed high levels of CTLA-4, GITR and ICOS, with significant, though low expression of CD62L and 00103, and hardly detectable expression of the chemokine receptor CCR7. T-bet was uniformly expressed but not Foxp3, whilst CD127 was only faint (FIG. 12b). In addition, Treg clones express high levels of Granzyme B and perforin. RT-PCR experiments show detectable levels of Granzyme A mRNA, but at a much lower level than Granzyme B (FIG. 12c). The cytokine secretion pattern showed almost exclusively IFN-gamma, but no or very little IL-10 and no TGF-β (FIG. 12d). Surface-bound TGF-β was not detected.

All cytolytic Tregs were anergic as they did not respond to antigen activation in the absence of added IL-2. The latter reversed anergy without restoring IL-2 transcription and with no loss of regulatory properties, as shown after restimulation cycles. This suggest an epigenetic alteration, possibly related to hyper-expression of T-bet. In addition, these clones expressed high levels of egr-2, known to activate the transcription of cell cycle negative regulators.

These cells expressed high levels of CD44, but showed low expression of CD45RB (and CD62L as mentioned above), identifying them as memory cells. Absence of production of suppressive cytokines suggests that their mechanism of action requires cell-cell contact. Expression of granzymes and perforin ranked such clones among T cells with a cytolytic potential. Lastly, the Vβ usage of cytolytic Tregs was determined, which indicates a predominance of Vβ8.1, with some clones belonging to the Vβ7 family. The beta chain of a number of clones was sequenced, showing significant differences in CDR3, which indicated that the response towards the p21-35 peptide was oligoclonal.

Treg clones were therefore evaluated functionally to determine both the mechanism of target cell lysis and their capacity to elicit bystander T cell suppression.

Induction of Apoptosis in Antigen Presenting Cells

Figure 13A:
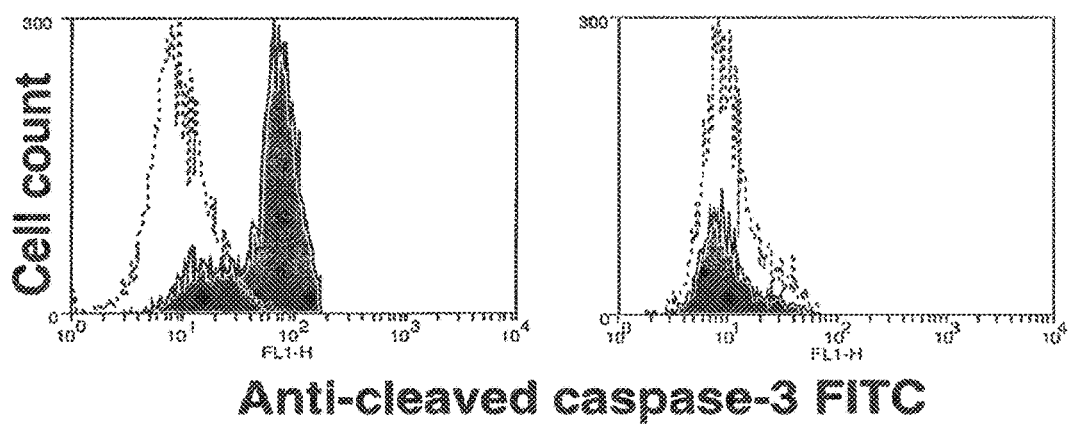

Lysis of antigen-presenting cells was obtained with both B cells and dendritic cells. Splenic B cells from naïve BALB/c mice, preloaded with p21-35 were induced to caspase 3 activation only when incubated with the R3T87 cytolytic T cell clone (i.e. another T cell clone with cytolytic activity, obtained in a similar way) (FIG. 13a: left panel), but not when a control CD4+ effector p21-35-specific T cell was added (FIG. 13a right panel). The same experiments were repeated using Annexin V as an apoptosis marker, providing the same results.

Figures 13B, 13C, 13D:
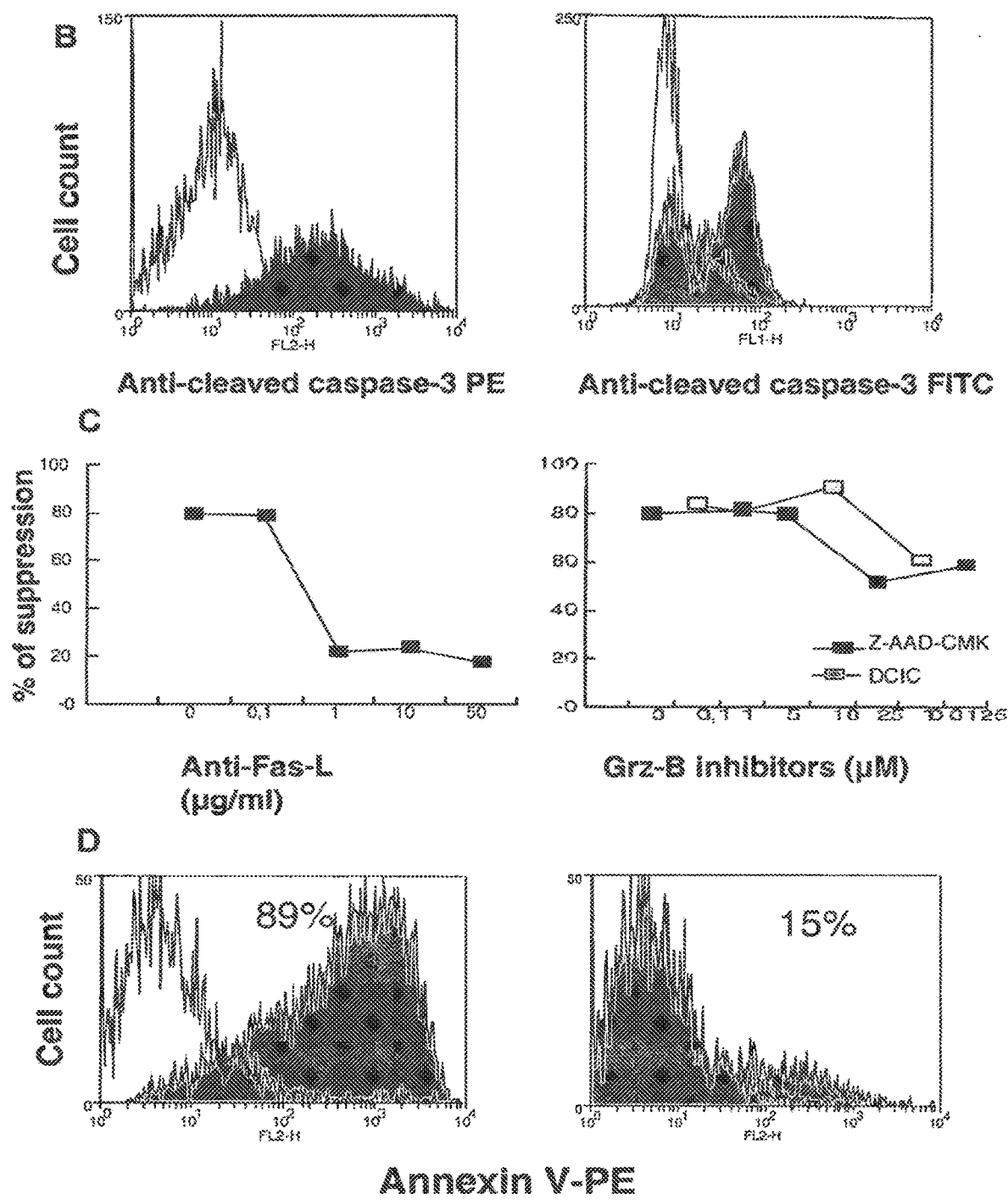
Figure 13:
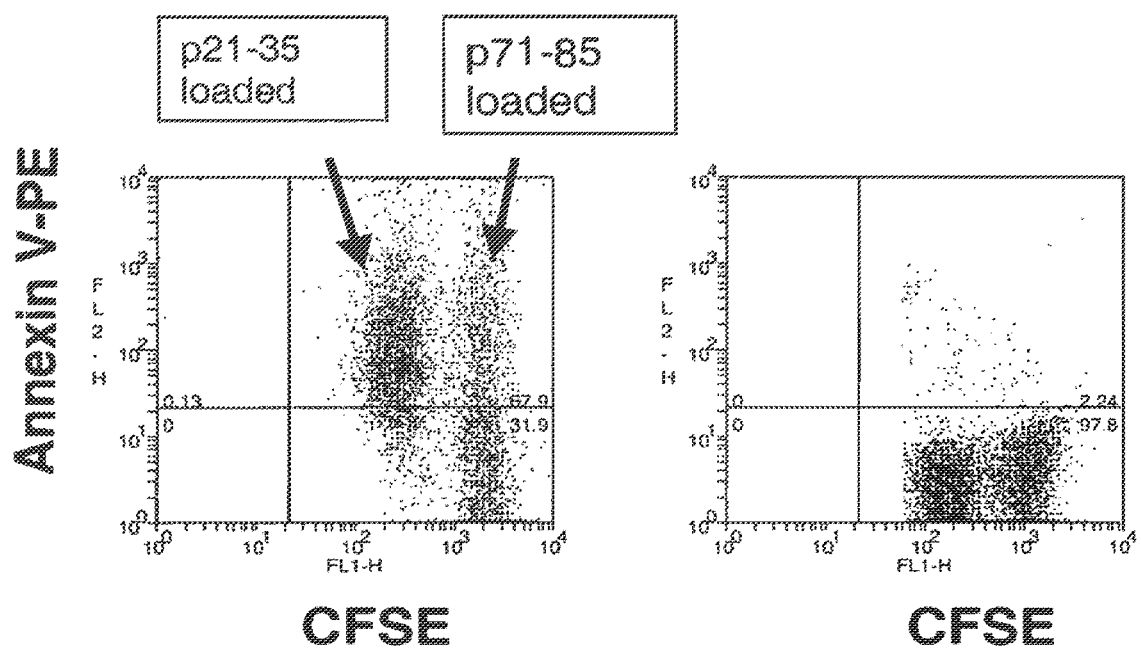

Experiments were carried out with p21-35-loaded CD11c dendritic (FIG. 13b: left panel) or WEHI cells (FIG. 13b: right panel). Upon incubation with R3TB7 virtually all dendritic cells (DC) or Wehi cells were induced into apoptosis as measured by caspase 3 activation. The same experiments were carried out with Annexin V and showed identical results.

Apoptosis can be induced by either the Fas-FasL pathway or by secretion of cytotoxic granules containing granzymes. Attempts were made to inhibit each of these pathways. Addition of increasing concentrations of an antibody towards FasL, or of granzyme B inhibitors, to a cell culture containing p21-35 loaded WEHI cells and a cytolytic T cell clone, increased the number of surviving WEHI cells in a dose-dependent manner (FIG. 13c). In a number of experiments it was shown that the anti-FasL antibody restored up to 80% of WEHI cell survival. Only partial restoration of survival was obtained with granzyme B inhibitors and only when high doses, close to cell cytotoxicity, were used, indicating that granzyme B did not account for much of the cell cytolysis. In additional experiments, EGTA was used as an inhibitor of granule exocytosis, which also showed only partial restoration of Wehi cell survival.

It was further evaluated whether target cell lysis required contact between cells. To this end, CD11+ DC loaded with p21-35 were used (or mp21-35Asn in parallel experiments), When loaded DC cells were incubated with the G121 cytolytic T cell clone, lysis was observed in 89% of the cells as measured by Annexin V expression (FIG. 13d, left panel). When the same experiments were carried out in a transwell system, DC lysis was limited to 15%, indicating that lysis required direct contact between cells (FIG. 13d, right panel).

To further ascertain that APC lysis required direct contact with cytolytic T cells through MHC class II presentation of p21-35, an experiment was carried out in which two identical populations of Wehi cells were loaded with either p21-35 or with an irrelevant peptide (p71-85). These two populations could be distinguished by differential CFSE labelling. It can be seen from FIG. 13e that, while WEHI cells presenting p21-35 were fully lysed, only 40% of p71-85-loaded cells were affected.

Altogether, it emerges that cytolytic T cell clones induced apoptosis of DC and B cells by a mechanism requiring the formation of an immune synapse by MHC class II-dependent peptide presentation. Significant participation of Fas-FasL is demonstrated, but only limited involvement of granzyme B.

Bystander T Cell Suppression

The mechanism of bystander T cell suppression was examined with polyclonal CD4+CD25(–) T cells and with various CD4+ effector T cell clones.

Figure 14:
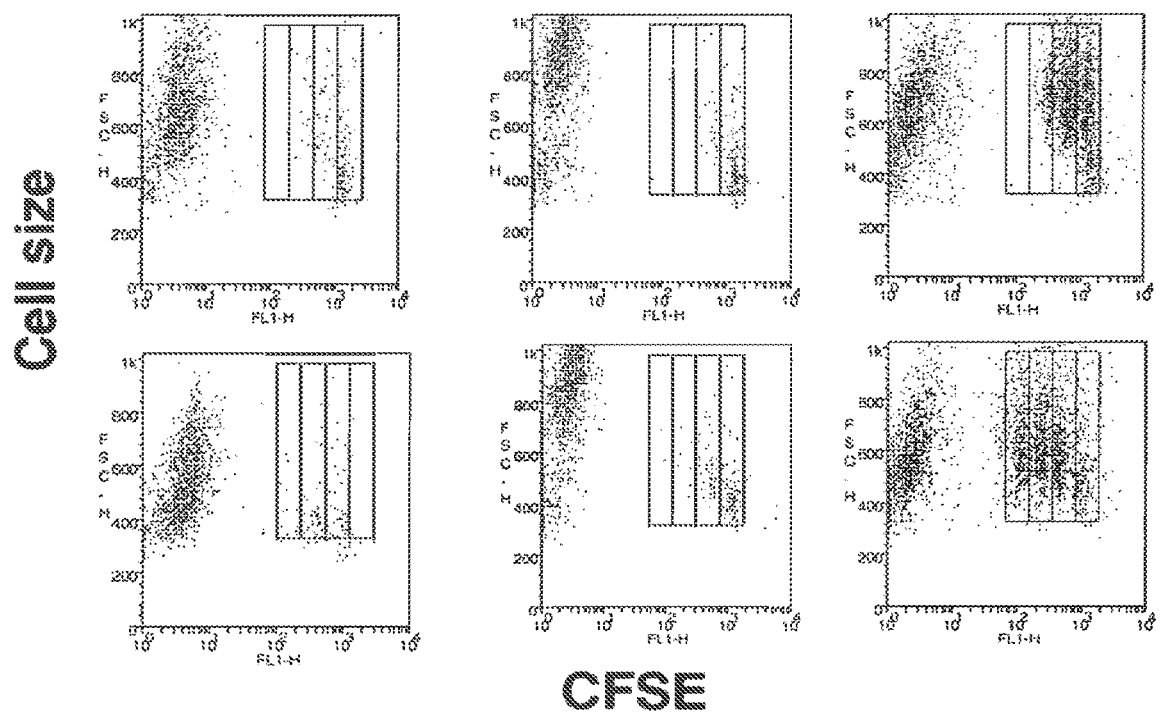
Figure 14B:
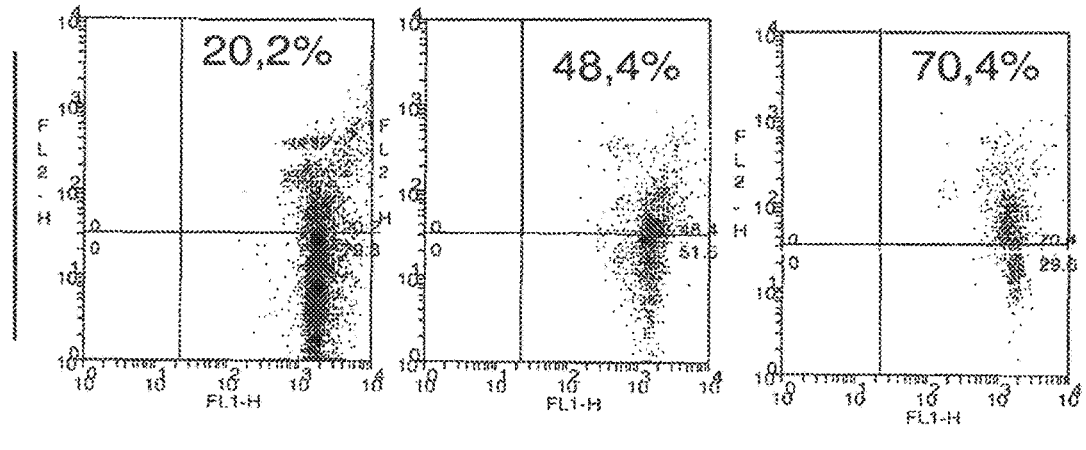

First, the capacity of Tregs was assayed to suppress the proliferation of CD4+CD25(–) T cells after anti-CD3 activation in the presence of antigen-presenting cells. The results obtained for two cytolytic T cell clones (G121 and R3TB7) is shown in FIG. 14a. The number of detectable CD4+CD25(–) T cells, as well as the number of observed divisions dramatically dropped within 48 h incubation when either one of the two cytolytic clones were added (upper left and middle panels). This effect was even more pronounced at 72 h for the second T cell clone (lower middle panel). Interestingly, only activated CD4+CD25(–) T cells were lysed, as can be seen from the vertical axis representing blast formation. The control experiment in which Treg was replaced by an identical number of unlabeled CD4+CD25(–) T cells (right panels) eliminated a possible artefact related to variable numbers of total cells in the culture medium.

Next, the kinetics of suppression were analysed. In the experiments shown in FIG. 14b, it can be seen that 48 and 70% of CFSE-labelled CD4+CD25(–) T cells express Annexin V after 18 and 24 h co-incubation with a cytolytic Treg (R3TB7), respectively, using the same assay system as in FIG. 14a.

Figure 14C:
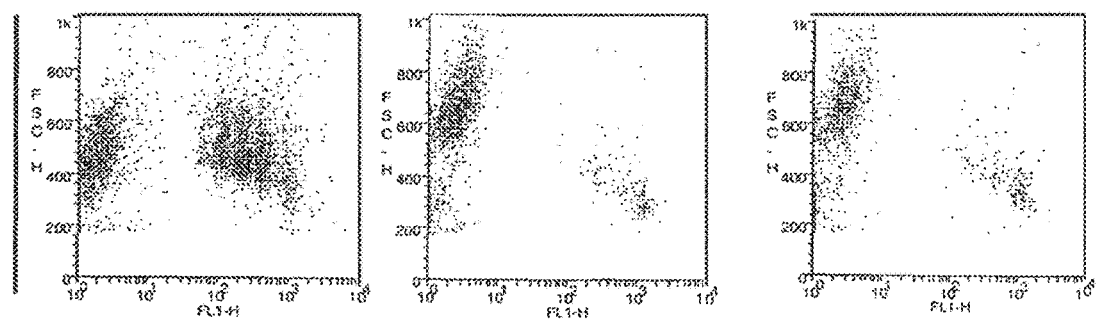

Such a rapid effect suggests the involvement of secretory pathways similar to those used by CD8+ cytotoxic T cells. The experiments were therefore repeated to verify whether inhibition of granules exocytosis by addition of EGTA to the culture would inhibit suppression. Basically no inhibition of the suppression of bystander T cells examined at 72 h with 2 concentrations of EGTA (FIG. 14c).

Next, it was evaluated whether T cell clones of defined specificity and different phenotypes could be suppressed by cytolytic T cells when activated by cognate recognition of corresponding antigens, instead of non-specific anti-CD3 activation. To this end, three clones were derivatised from BALB/c mice, namely a Th2 cell specific for a second unrelated allergen from the same source (Der p 1), a Th1 cell specific for a second major T cell epitope of Der p 2 (amino-acids 71-85) and a Th0 clone specific for the 830-844 subdominant T cell epitope of tetanus toxoid. Each of these 3 clones was used in all the assay systems reported here. Results are shown for one single clone in each assay, but results were confirmed in all possible combinations of assays and clones.

Figure 14D:
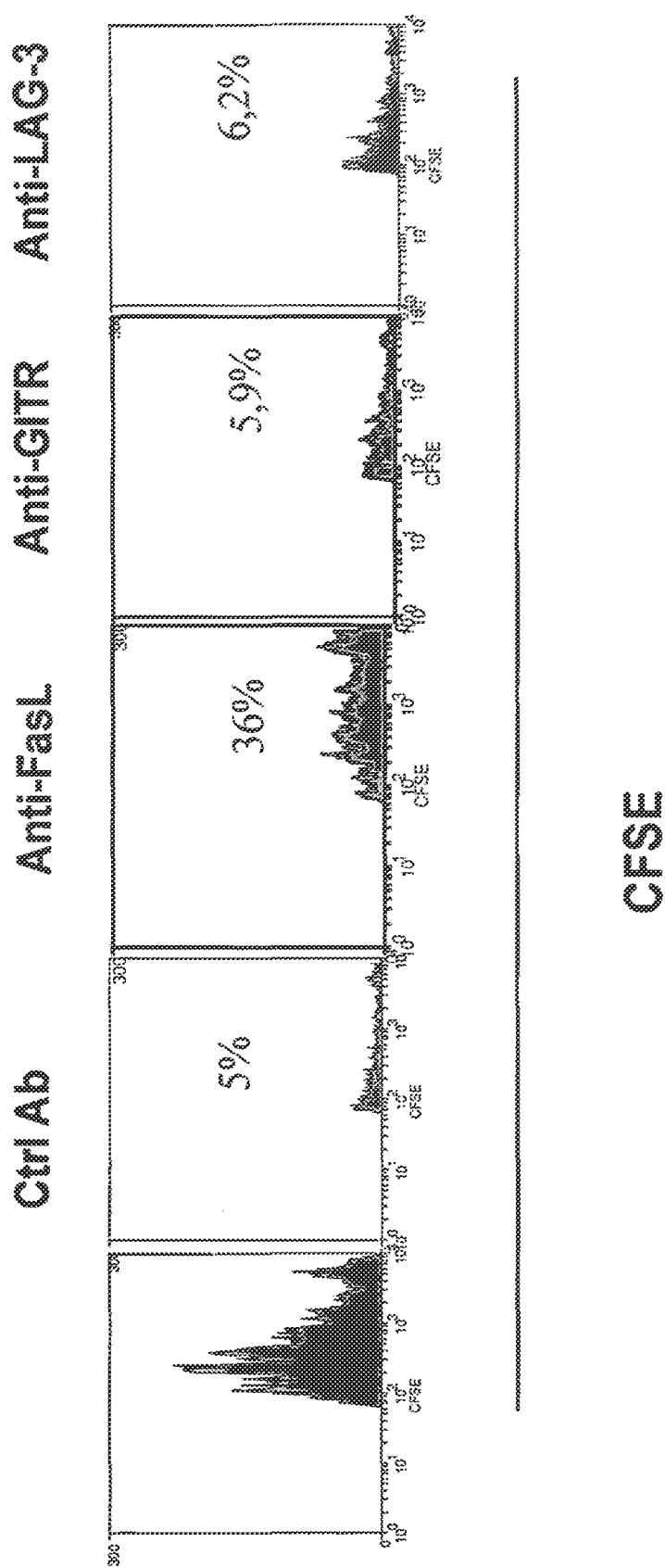

In a first set of assays, the proliferation of a T cell clone was measured using CFSE-labelled cells after presentation of the corresponding antigen by T cell depleted splenocytes. To eliminate an artefact due to competition for nutrient in the culture medium, an equal quantity of the unlabeled Th2 clone was added to the CFSE-labelled Th2 clone. A Th2 clone specific for Der p 1 readily proliferated as measured over a time period of 72 h (FIG. 14d). In parallel assays, APC were also loaded with p21-35 and a cytolytic T cell clone added at a 1/1 ratio to the Der p 1 specific Th2 clone. The Figure shows that only 5% of the Th2 clone survived after 72 hours incubation. The Figure also shows that addition of specific antibodies to FasL over the entire incubation period resulted in a partial inhibition of suppression (36% residual Th2 clone), whilst an anti-GITR or anti-Lag3 antibody had no effect. Identical results were obtained with a Th1 clone to Der p 2 and with a Th0 clone to tetanus toxoid. The clones were therefore amenable to suppression by cytolytic T cells independently of their maturation state, provided activation occurred through MHC class II cognate interaction.

Figure 14E:
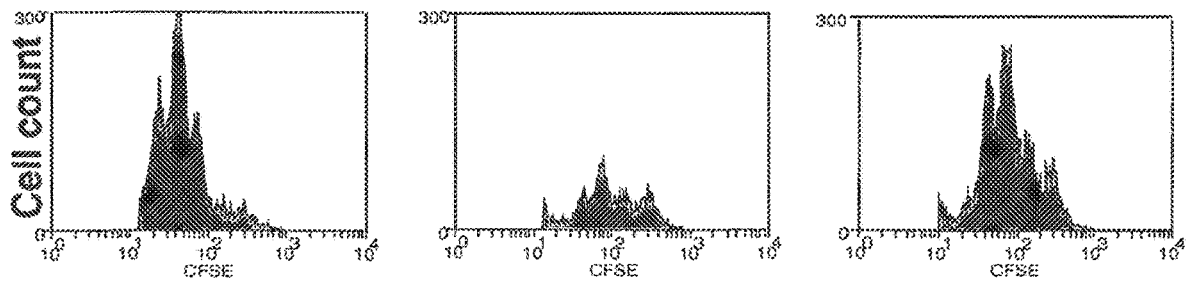

The question as to whether contact interaction was required between the cytolytic T cells and bystander T cells was examined in a transwell culture system. Results are shown in FIG. 14e. T cell depleted splenocytes loaded with both p21-35 and p71-85 sustained the proliferation of a p71-85 specific Th1 clone. Addition of a p21-35 cytolytic Treg suppressed proliferation (middle panel), When peptide-loaded APC were separated in a transwell culture system and the cytolytic cell line added to one compartment, with the 71-85 specific Th1 clone in the second compartment, no suppression was observed (right panel). It could therefore be concluded that suppression was not mediated by soluble factors. These experiments were confirmed using the Th2 cell clone to Der p 1.

Figure 14F:
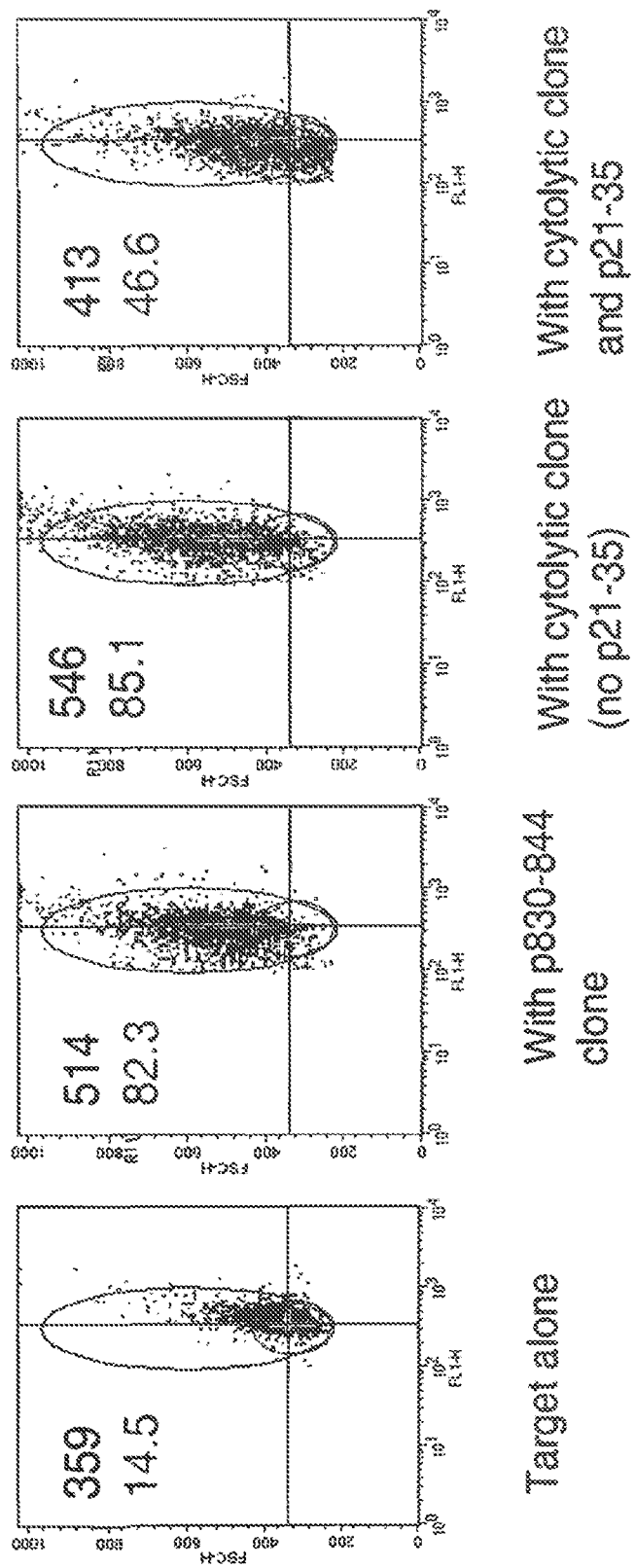
Figure 15:
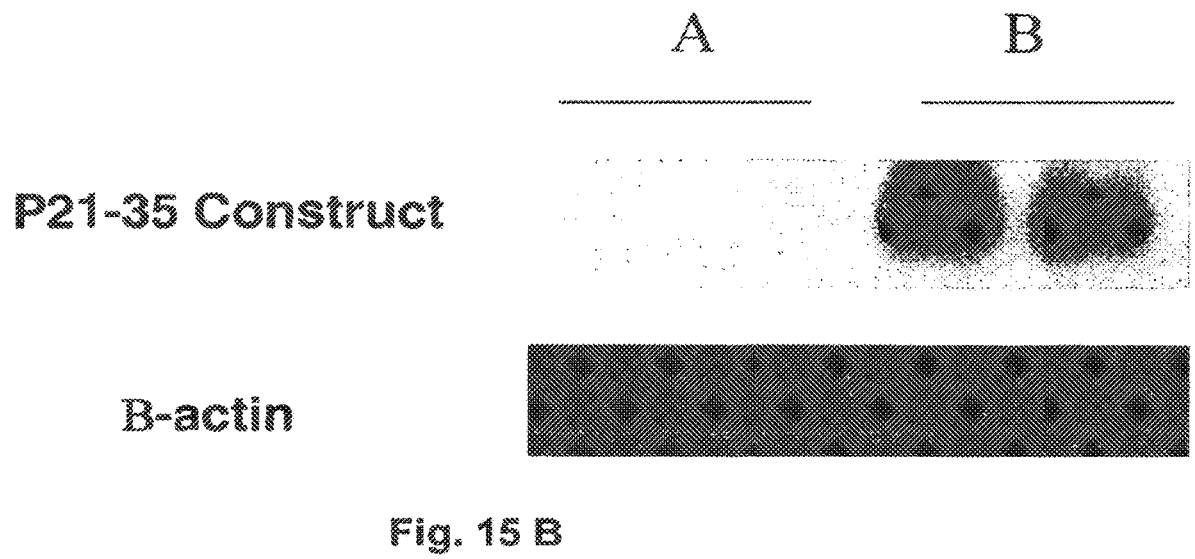

Cytolytic Tregs efficiently prevented bystander T cells blast formation. The average cell size of bystander T cells is only marginally increased when co-cultured in the presence of activated cytolytic Treg (R3TB7) as shown in FIG. 14f. This was accompanied with an increased proportion of cell death as measured with the CFSE-labelled bystander cells. The percentage of cell death was 26% for bystander cells alone, 36% with the control p830-844 clone used in place of the cytolytic clone, 34% with the cytolytic clone without activation, and 51% with the cytolytic clone in the presence of the activating peptide.

In order to exclude that bystander suppression could be partly due to artefacts, due to the lysis of APC, additional assays were carried out in which two distinct populations of APC (Wehi-231 B cells), each incubated with either p21-35 or with a readout peptide (the Der p 1 derived T cell epitope or p830-844 of tetanus toxoid). The two APC were cultured in the same well and both a cytolytic T cell clone and a CFSE-labelled effector cell. It was observed that the labelled T cell clone was suppressed. APC presentation of p21-35, required to activate cytolytic Tregs, was replaced by a combination of anti-CD3 and anti-CD28 antibodies. Under such circumstances the proliferation of effector cells activated by cognate recognition was also suppressed, Taken together with experiments reported in FIG. 14e, this shows that cytolytic T cell clones suppressed bystander T cells in the absence of APC apoptosis induction.

Cytolytic Tregs Lyse p21-35-Loaded B Cells In Vivo

Cytolytic Tregs induce apoptosis of APC in vitro. To determine whether this activity was relevant in an in vivo setting, transgenic B cells expressing p21-35 in the context of MHC class II determinants were used. Such transgenic B cells persist for at least 3 months in the spleen after adoptive transfer. First, it was verified whether cytolytic Tregs could induce apoptosis of transgenic B cells in vitro, 52% of B cells are induced in apoptosis after 18 h incubation with a cytolytic T cell clone (FIG. 15a). Expression of the construct in spleens of control mice (lanes B), but not in spleens of mice transferred with both transgenic B cells and Tregs (lanes A) is shown in FIG. 15b. No viral construct was detected in lung cells, in the absence of allergen exposure. These data indicated that cytolytic T cells maintained their capacity to lyse B cells presenting the cognate antigen after in vivo transfer.

Cytolytic Tregs Accumulate into the Lungs Upon Allergen Exposure

The memory phenotype of the Tregs, combined to the absence of CCR7 and low levels of CD103, suggest that they can migrate to the lungs, where they can exert their suppressive activity.

Two different cytolytic T cell lines were labelled with either CFSE or SNARF (both markers for cytoplasmic proteins, emitting at different wavelengths) and used in separate experiments. Accumulation of CFSE-labelled cells was found in perivascular and peribronchial lung areas (data not shown). Control mice receiving labelled Tregs but no allergen instillations showed virtually no lung fluorescence.

To establish whether Tregs represent a significant proportion of lymphocytes accumulating in lungs, and to discard a possible artefact related to the inherent toxicity of fluorescence labelling, unlabeled Tregs were adoptively transferred to BALB/c mice. In these experiments, use was made of the fact that cytolytic cells expressed Vβ8.1 and counted the proportion of positive cells over the entire CD4+ population accumulating in lungs after nasal instillation with allergen. Under such conditions, it is known that very little lymphocytes are attracted to lungs in the Der p 2 model of asthma. In the group of mice transferred with the cytolytic T cell clone more than 90% of CD4+ cells expressed Vβ8.1, whilst only 25 and 20% of such cells were detected in the group treated with the control Vβ8.1.+ cell line, and in a control group of mice that received Der p 2 by inhalation but no T cells, respectively (FIG. 15c).

It is therefore concluded that cytolytic Tregs accumulated into the lungs upon allergen challenge by nasal instillation.

Cytolytic Treg Clones Prevent and Suppress Experimental Asthma

The above-described experiments suggested that cytolytic T cell clones could be of value for the control of specific immune responses in vivo. The requirement for MHC class II cognate interaction and induction of apoptosis of APC could provide an opportunity to suppress the entire response towards single antigens. In addition, their accumulation in lung tissue could favour their regulatory activity on some of the features associated with asthma.

This was tested by adoptively transferring cytolytic T cells specific for p21-35 in both a preventive and suppressive settings. The experimental asthma model to Der p 2 was used as described above, Two cytolytic T cell lines were used, as obtained from BALB/c mice immunised with mp21-35Asn.

Figures 16A, 16B, 16C, 16D, 16E, 16F:
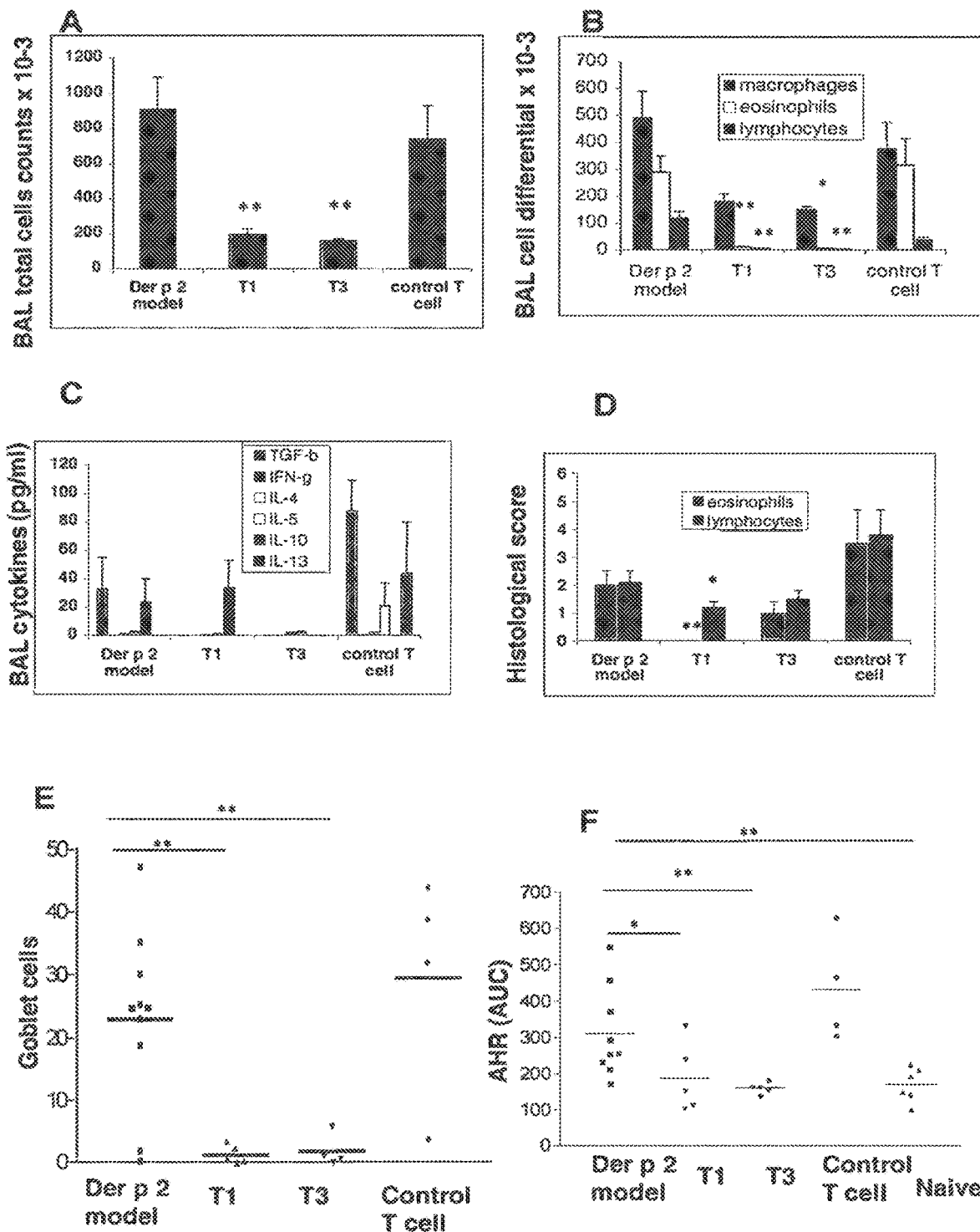
Figures 16G, 16H, 16I, 16J, 16K, 16L:
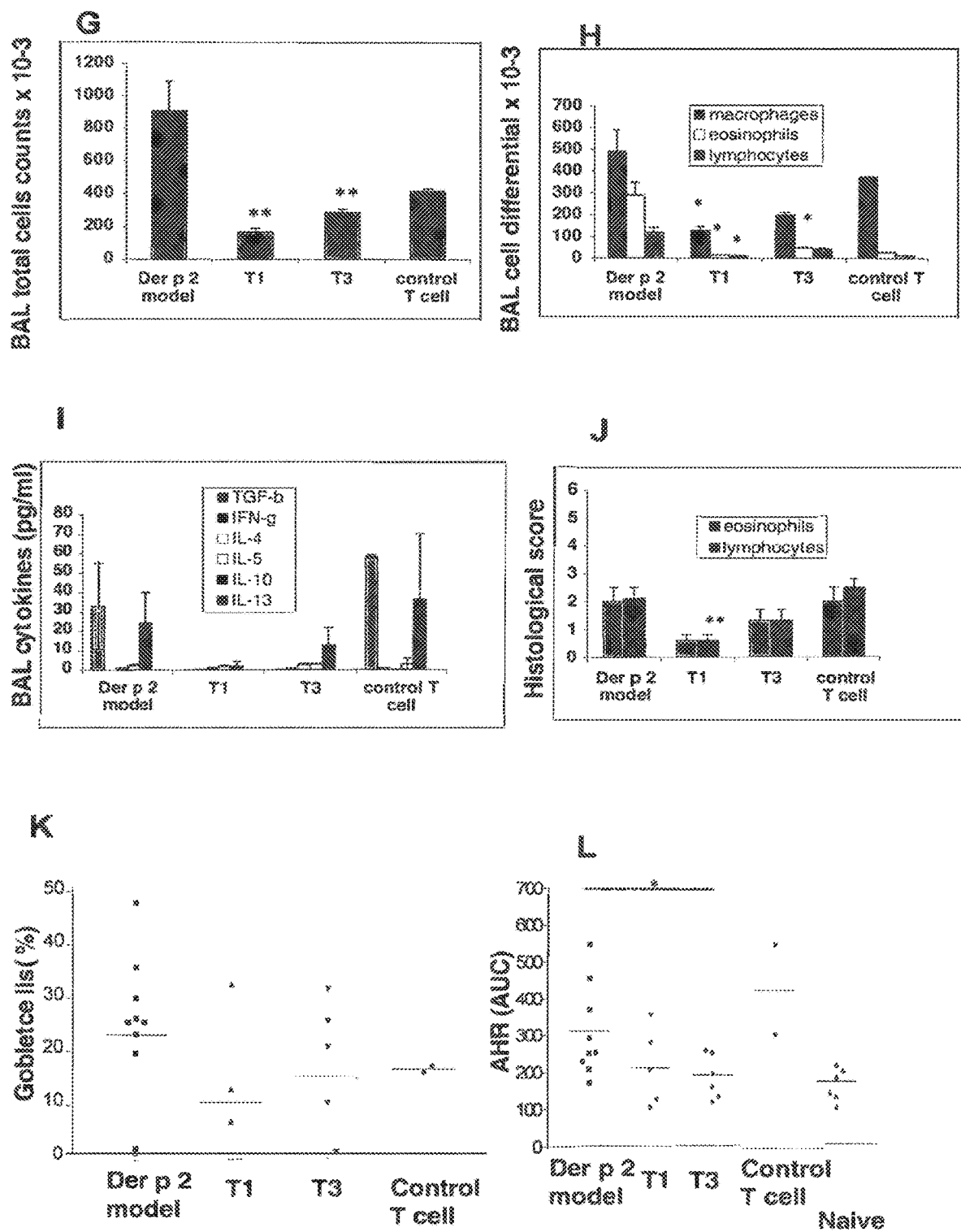

The results of the prevention experiments are shown in FIG. 16(a-f). It can be seen that the transfer of cytolytic T cells prior to induction of Der p 2 sensitisation reduced the number of cells recovered from BALF to values observed in naïve animals (not shown in FIG. 16a), with virtually no cells except macrophages. The control cell line had no effect on BALF cell recovery as compared to the positive control group. The two cytolytic cell clones produced essentially the same effect. The production of TGF-β in BALE was undetectable with the two Tregs, while IL-10 production was suppressed with the second clone. Significant reduction of lung eosinophil infiltration and goblet cell hyperplasia was observed. In addition, airway hyper-reactivity measured by inhalation of increasing doses of methacholine was practically reduced to levels observed in naïve mice (naive).

When the same two cytolytic cell lines were used after Der p 2 sensitisation, similar improvement of biologic and functional parameters were observed (FIG. 16(g-l)). One notable exception, however, was the presence of goblet cell hyperplasia. Interestingly, airway reactivity to methacholine was comparable to that of naïve animals. In additional testing these last results were verified by dynamic compliance measurements, which provided essentially the same results.

Example 12: Immunisation of BALB/c Mice with Der p 1 Derived Peptide

Two groups of BALB/c mice were immunised by the subcutaneous route with either 20 µg of peptide with a T cell epitope sequence of the allergen Der p1 (SNYCQIYPPNANKIR [SEQ ID. NO: 5]) or a modified version thereof CGFS SNYCQIYPPNANKIR [SEQ ID. NO: 7] having at the N-terminus the sequence CGFS [SEQ ID. NO: 6].

The amino acids of Der p 1 which reside in the cleft are S114 (or N115) to P122 (or P123) (where MHC class II haplotypes binding 9 amino acids in the cleft are concerned). The SNYC sequence which is present in the Der p 1 is thus not accessible and can not interact with other proteins and perform its reducing activity.

After 3 injections, mice were sacrificed and CD4+ T cells were purified from the spleen and cloned by limiting dilution. T cell clones obtained from mice immunised with the SNYCQIYPPNANKIR [SEQ ID. NO: 5] peptide produced effector CD4+ T cells characterised by proliferation and cytokine secretion following cognate interaction with MHC class II presentation of peptide. Mice immunised with the peptide CGFS SNYCQIYPPNANKIR [SEQ ID. NO: 7] produced T cell clones with cytolytic properties, as determined in an assay similar to that described in Example 10.

To determine whether T cells with cytolytic properties (as shown in Example 10) had the capacity to induce apoptosis of effector T cells, antigen-presenting cells (APC) were prepared from adherent splenic cells. APCs were incubated with the Der p 1 allergen for presentation into MHC class II determinants.

As shown in FIG. 17, CD4 effector cells readily proliferated when added to antigen-loaded APCs. Addition of cytolytic T cells induced death of CD4 effector cells (7-AAD positive staining (FL3-H)). FIG. 17 shows apoptosis in 73% of the effector cells and the strong abrogation of the proliferation of CD4 effector cells.

Example 13: Adoptive Transfer of T Cell Clones with Cytolytic Activity Fully Prevents and Suppresses Asthma Elicited by Nasal Instillation of the Der P 1 Allergen BALB/c mice were submitted to 2 series of 3 daily nasal instillations separated by 1 week, using 100 µg of the Der p 1 allergen. The day after the last nasal instillation, mice are sacrificed and checked for the presence of alterations characteristic of allergic asthma in the bronchoalveolar space and lung.

Two additional groups of mice are adoptively transferred with cytolytic T cell clones obtained as described in Example 11 using the Der p 1 peptide with the motif, either prior to or after the first series of nasal instillations.

BALF differential cell counts were carried out 4 days after the last series of nasal instillations (6 BALB/c per group). Cells were obtained by bronchoalveolar lavage of lungs and identified on cytospins as macrophages, neutrophils, eosinophils or lymphocytes. Mice received 2 series of 3 nasal instillations with either 100 µg Der p 1 (model) or NaCl (negative). FIGS. 18A and B show that when cytolytic T cells are administered before or after the first nasal instillation series, this results in complete abolition of eosinophil infiltration into the bronchi. As can be seen, the total number of cells recovered in the lavage fluid is within the range of what is obtained from naïve animals.

Broncho-alveolar lavage fluids were tested for the presence of cytokines (Table 6). Mice receiving a cytotoxic clone showed very low cytokine recovery, including the concentration of IL-10 which is significantly increased in the model.

TABLE 6

BAL cytokines determination of mice treated with Der p 1 modified peptide [SEQ ID. NO: 7] (three days after the last nasal instillation).

| | TNF-alpha | IFN-gamma | IL-5 | IL-4 | IL-2 | IL-10 | IL-13 | TGF-beta |
|---|---|---|---|---|---|---|---|---|
| Prevention | 0.7 | 0 | 0.3 | 0 | 0.7 | 10 | 0.2 | 5.8 |
| Suppression | 0 | 0 | 0.5 | 0.7 | 0.8 | 2 | 0.3 | 0 |
| Model | 0 | 0 | 0 | 0 | 0 | 44 | 4 | 1 |
| Neg. | 6 | 1 | 0.5 | 2 | 0 | 0 | 0 | 0 |

Results represent average concentrations obtained from 6 BALB/c (pg/ml).

Example 14: Effect of Increasing the Redox Potency of Modified Peptides on the Capacity to Activate Cytolytic Regulatory T Cells Antigen-presenting cells were loaded with p21-35 in its native configuration [SEQ ID. NO: 2] or p21-35 in which serine in position 24 is substituted by cysteine CHGCEPCI-IHRGKPF [SEQ ID. NO: 29]. This substitution creates a redox moiety of the type C-x-x-C.

Several regulatory T cell clones with cytolytic activity were incubated with APC. FIG. 19 shows that the peptide carrying the C-x-x-C redox sequence induces a higher degree of T cell activation, assessed by cytokine production, than its C-x-x-S counterpart. It is also shown that the C-x-x-C sequence induces the transcription of mRNA for both FasL and granzymes, more than its C-x-x-S counterparts. The granzymes are two of the key players in induction of apoptosis of target cells.

Example 15: Prevention and Suppression of Beta-Lactoglobulin Allergy

Bovine beta-lactoglobulin (BLG) is a major allergen in human milk allergy. A mouse model is used to determine whether modified peptides could alter the specific response towards BLG. The peptide CHGC AQKKIIAEK [SEQ ID. NO: 30] encompassing the thioredox motif sequence C-H-G-C [SEQ ID. NO: 31] linked to a T cell epitope of BLG is synthesised.

BALB/c mice are immunised by 2 SC injections with 20 µg of the peptide of sequence CHGC AQKKIIAEK [SEQ ID. NO: 30] in alum. This is followed 15 days later by intraperitoneal sensitisation to BLG (5 µg in alum), on 2 occasions at a fortnight interval. Alternatively, peptide administration is given 15 days after IP sensitisation to BLG.

Hypersensitivity to BLG is verified in the mouse by assessing bronchial hyperreactivity after intranasal administration of BLG. All mice are submitted to intranasal administration of 10 µg of BLG in saline 10 days after the last injections. A control group is included in which intraperitoneal sensitisation is carried out without peptide immunisation.

Mice injected with the modified peptide epitope prior to or after sensitisation have completely lost the capacity to react to BLG nasal instillation. This is shown by the lack of eosinophils in bronchoalveolar lavage fluid and the absence of hyperreactivity upon challenge with increasing doses of methacholine, as compared to the control group, in which both eosinophils and hyperreactivity are observed.

Example 16: Prevention and Suppression of Multiple Sclerosis

Groups of C57BL/6 mice are immunised subcutaneously (20 µg) with peptide (CHGS YRSPFSRVVHLYR [SEQ ID. NO: 32], which contains the sequence motif C-X(2)-S) or control peptide (YRSPFSRVVHLYR [SEQ ID. NO: 33]) adsorbed onto aluminium hydroxide, Three injections are performed at 2-week intervals. Ten days after the last immunisation, mice are sacrificed and CD4+ T cells ($2 \times 10^6$ cells) are prepared from the spleen using magnetic beads. CD4+ T cells are then stimulated in vitro by the MOG T cell epitope (20 µg/ml) presented by adherent spleen cells ($2 \times 10^6$ cells).

After four re-stimulations, a T cell line is tested in a bystander suppression assay with, as target cells, polyclonal CD4+CD25− cells obtained from animals in which EAE (Experimental autoimmune encephalomyelitis) was effective. Only the cells obtained from animals immunised with the peptide containing the C-X(2)-S sequence motif have the capacity to induce death in target cells, as compared to the control consisting in effector CD4+CD25− from EAE animals, as shown in FIG. 20.

A group of C57BL/6 mice is adoptively transferred with a CD4+ MOG-specific regulatory T cell clone followed after 1 day by a protocol meant to induce a multiple sclerosis-like syndrome. This involves administration of the MOG peptide in complete Freund's adjuvant and 2 injections of Pertussis toxin. This protocol elicits an expansion of the effector T cell clone, which results in the development of signs compatible with multiple sclerosis within 12 days after the MOG peptide administration. It is observed that the clinical score developed by mice pre-treated with the cytolytic T cell clone is significantly reduced as compared to mice receiving only the full protocol of disease induction (FIG. 21).

It is observed that the clinical score developed by mice pre-treated with the cytolytic T cell clone is significantly reduced as compared to mice receiving only the effector T cell clone, as shown in FIG. 21.

Example 17: Prevention of Multiple Sclerosis by Peptide Immunisation

In the model group, 3 C57BL/6 mice received, at day 0, SC injection of 100 µg MOG peptide/400 µg *Mycobacterium butyricum* in CFA and ip injection of 300 ng Bortetella pertussis in NaCl. At day +2, a second injection of B. pertussis was given.

In the prevention group, 5 C57BL/6 mice are immunised by 5 injections with 20 µg CSMOG peptide (CHGS YRSPFSRWHLYR [SEQ ID. NO: 32]), which contains the sequence motif C-X(2)-S, in IFA at 14 days interval before disease induction as in the model group. Control experiments are performed with the peptide [SEQ ID. NO: 33] lacking the motif at its N-terminus.

Scores were established as 0: no disease, 1: limp tail, 2: limp tail and loss of weight higher than 10%, 3: partial paralysis of hind limbs.

FIG. 22 shows that pre-treatment with modified peptide [SEQ ID. NO: 32] completely abolishes the development of the syndrome.

Example 18: Prevention and Suppression of Spontaneous Insulin-Dependent Diabetes with GAD65 Derived Peptides Non-obese diabetes (NOD) mice constitutes a suitable animal model for spontaneous insulin-dependent diabetes.

In such animals, as in human beings, an early immune response to the autoantigen glutamic acid decarboxylase (GAD65) is observed at a time at which insulitis can be seen, from which the response extends by intramolecular and intermolecular spreading. Inducing tolerance to GAD by administration of the protein to neonates prevents the onset of diabetes.

The carboxy-terminal region of GAD65, and in particular the fragment 524-543 SRLSK$_{528}$VAPVIKARMMEYGTT [SEQ ID. NO: 34], is recognised by specific T cells. Some of such T cells are pathogenic, such as those recognising fragment 530-543, whilst others do not elicit the disease, such as those recognising the fragment 524-538.

Lys528 constitutes a P1 anchoring residue. For the generation of a peptide in accordance with the invention, Serine residues P-4 and P-1 are replaced by a cysteine, which results in CRLC KVAPVIKARMM [SEQ ID. NO: 35]. Treg cells with cytotoxic properties are elicited by immunisation with the above modified peptide comprising the T cell epitope of the GAD65 protein. T cells obtained from the spleen of NOD mice aged 20 weeks, at a time at which insulitis is present as well as overt diabetes are expanded in vitro with peptide 524-543 in order to generate pathogenic T cell clones.

NOD mice are immunised with peptide containing the thioredoxin consensus sequence in IFA (incomplete Freund adjuvans) from the age of 2 weeks. T cells are expanded in vitro to generate clones with regulatory properties.

Polyclonal cells purified from mice immunised with the thioredoxin consensus sequence induce apoptosis in polyclonal CD4 cells obtained from peptide 524-543 immunised NOD mice when stimulated by antigen-presenting cells loaded with peptide 524-543 (see FIG. 23). The table in FIG. 23 represents the percentage of double positive cells (dead cells) after substraction of background values obtained without the regulatory population.

Adoptive transfer of Treg at the age of 2 weeks in NOD mice, namely before the onset of insulitis (3 weeks of age) is shown to fully prevent the onset of diabetes.

Direct immunisation of NOD mice with the peptide CRLC KVAPVIKARMM [SEQ ID. NO: 35]. from the age of 2 weeks is shown to fully prevent diabetes and lesions of insulitis.

In a suppressive setting, adoptive transfer of Treg at different ages between 6 and 20 weeks is shown to suppress diabetes and insulitis in NOD mice. Immunisation with peptide CRLC KVAPVIKARMM [SEQ ID. NO: 35] after the age at which insulitis is already prominent (15 weeks of age) is shown to suppress diabetes and insulitis.

Example 19: Prevention and Suppression of Spontaneous Insulin-Dependent Diabetes with Insulin Derived Peptides Tregs with cytolytic properties are elicited by immunising NOD mice with the T cell epitope of insulin linked to the motif C-X(2)-C with and without a glycine linker.

The peptides which are synthesised are:

```
EALYVCGERG CGPC           [SEQ ID. NO: 36]

EALYVCGERG G CGPC         [SEQ ID. NO: 37]

EALYVCGERG GG CGPC        [SEQ ID. NO: 38]

EALYVCGERG GGG CGPC       [SEQ ID. NO: 39]

EALYVCGERG GGGG CGPC      [SEQ ID. NO: 40]
```

The Treg cells obtained with these peptides induce apoptosis of insulin-specific pathogenic T cells in an in vitro system in which both pathogenic and regulatory cells are activated by presentation of insulin. They further prevent or suppress the onset of diabetes and insulitis after adoptive transfer of Tregs prior to (2 weeks of age) or after (6 weeks of age) the spontaneous onset of insulitis, respectively.

The Treg cells obtained with these peptides also prevent or suppress the onset of diabetes and insulitis when elicited in vivo upon immunisation with peptide of sequence containing the thioredoxin consensus sequence, starting at the age of 2 weeks for prevention or 15 weeks for suppression, respectively.

Example 20: Prevention and Suppression of Autoimmune Thyroiditis with Thyroperoxidase Derived Peptides Autoimmune thyroiditis in man is associated with the production of antibodies to thyroid peroxidase. Antibodies and specific T cells to TPO result in thyroid cell destruction by a combination of cytotoxic and cytolytic mechanisms, leading to hypothyroidism. On purpose immunisation of C57Bl/6 mice with TPO elicits a disease state identical to human pathology and is therefore considered as a suitable model for autoimmune thyroiditis.

The fragment 540-559 (QGQLM$_{544}$NEELTERLFVLSNV [SEQ ID. NO: 41] of TPO encompasses a dominant T cell epitope of TPO recognised by C57Bl/6 mice.

The use of different algorithms identified residue Met544 as the first anchoring residue into MHC-class II determinants. Amino acids P-4 to P-1 are replaced by the sequence of D-isomer CGPC [SEQ ID. NO: 42], which generates the sequence (CGPC)$_{D\text{-}isomer}$ MNEELTERL [SEQ ID. NO: 43].

C57Bl/6 mice are immunised twice with the experimental peptide [SEQ ID. NO: 43] or the control peptide [SEQ ID. NO: 41] or QGQLM$_{544}$NEELTERL [SEQ ID. NO 48] in CFA/IFA. Ten days after the last immunisation, mice are sacrificed and T cells are prepared from the spleen. CD4+ T cells are expanded in vitro using antigen-presenting cells loaded with the 540-559 sequence. T cell clones are obtained by limiting dilution.

The capacity of T cell clones generated with the experimental peptide (CGPC)$_{D\text{-}isomer}$ MNEELTERL [SEQ ID. NO: 43] to suppress activation of effector T cells obtained by immunisation with peptide of sequence 540-559 is tested in vitro.

Herein, antigen-presenting cells are loaded with peptide 540-559. Addition of the effector T cell done results in activation and proliferation of such cells, as measured by thymidine incorporation. When a T cell clone with regulatory activity is added to the system, together with the effector clone, activation and proliferation of the latter is completely inhibited.

Adoptive transfer of regulatory T cells to C57Bl/6 mice prior to or after immunisation with peptide 540-559 prevented or suppressed, respectively, induction of thyroiditis, as evaluated by assessing lymphocytic infiltration of the thyroid.

Example 21: Prevention and Suppression of Autoimmune Thyroiditis with Thyroglobulin Derived Peptides An immune response towards thyroglobulin is a common feature of human autoimmune thyroiditis. Induction of such a response in experimental thyroiditis upon injection of peptides encompassing T cell epitopes has been obtained in genetically predisposed animals such as H2k mice.

The thyroglobulin fragment 2340-2359 (QVA$_{2342}$ALTWVQTHIRGFGGDPR [SEQ ID. NO: 44]) encompasses a dominant T cell epitope of thyroglobulin recognised by AKR/J mice. The use of different algorithms identifies residue Ala2342 as the first anchoring residue into MHC-class II determinants. Amino acids P-4 to P-1 were replaced by the sequence CGPS [SEQ ID. NO: 13], which generates the sequence CGPS AALTWVQTH [SEQ ID. NO: 45].

AKR/J mice are immunised twice with the experimental peptide [SEQ ID. NO: 45] and the control peptide LDQVAALTWVQTH [SEQ ID. NO: 49] in CFA/IFA. Ten days after the last immunisation, mice are sacrificed and T cells prepared from the spleen. CD4+ T cells are expanded in vitro using antigen-presenting cells loaded with the 2340-2359 fragment. T cell clones were obtained by limiting dilution.

The capacity of T cell clones generated with peptide CGPS AALTWVQTH [SEQ ID. NO: 45] to suppress activation of effector T cells obtained by immunisation with peptide of sequence 2340-2359 is tested in vitro. Herefore, antigen-presenting cells were loaded with peptide 2340-2359. Addition of the effector T cell clone resulted in activation and proliferation of such cells, as measured by thymidine incorporation. When a T cell clone with regulatory activity is added to the system, together with the effector clone, activation and proliferation of the latter is completely inhibited.

Adoptive transfer of regulatory T cells to AKR/j mice prior to or after immunisation with peptide 2340-2359 prevents or suppresses, respectively, induction of thyroiditis, as evaluated by assessing lymphocytic infiltration of the thyroid.

Example 22: Prevention and Suppression of Pollen Allergy with Birch Pollen Allergen Derived Peptides Sensitivity to birch pollen is a common cause of rhinitis and asthma. However, about 60% of birch pollen-sensitised subjects develop symptoms upon ingestion of fruits of the Rosacea family, such as apple, pears, plums and cherries. Cross-reactivity between Bet v 1 (the main birch pollen allergen) and such food has been demonstrated at both the level of specific IgE antibodies and T cells. In particular a T cell epitope located at the carboxy-terminal end of the Bet v 1 molecule, which is conserved between various isoforms, shown a high degree of homology with the sequence of an equivalent allergen of apple (Mal d 1). Effector T cells recognising fragment 142-156 of Bet v 1 are strongly activated when exposed to the Mal d 1 corresponding epitope.

The peptide LRAVESYLLAH [SEQ ID. NO: 46] corresponding to residues 144-154 of Bet v 1, and containing a T cell epitope, is modified by addition of the sequence (CGPC)$_{D\text{-}isorner}$ [SEQ ID. NO: 42], at its aminoterminal end resulting in (CGPC)$_{D\text{-}isomer}$ LRAVESYLLAH [SEQ ID, NO: 47].

This peptide is adsorbed on aluminium hydroxide using 50 μg of peptide for 1 mg of alum. Three SC injections of 50 μg of peptide were carried out at 2-week intervals. Two weeks after the last injection, blood is drawn from a peripheral vein and CD4+ T cells purified by cell sorting on magnetic beads. CD4+ T cells were added to culture medium in which Histocompatible dendritic cells, used as antigen-presenting cells, were incubated with either the Bet v 1 antigen, or with tetanus toxoid as a control, for 2 h at room temperature. The cells were then washed and purified CD4+ T cells were added to the culture medium. Such CD4+ T cells induced apoptosis of dendritic cells presenting the Bet v 1 antigen, but not of dendritic cells presenting the tetanus toxoid protein, Incubation of CD4+ T cells with dendritic cells loaded with the Mal d 1 antigen resulted in dendritic cell apoptosis.

Patients presenting with allergic symptoms upon exposure to birch pollen together with an oro-pharyngeal allergy to ingestion of apple and treated by 3 SC injections of peptide CGPC LRAVESYLLAH [SEQ ID. NO: 47] failed to react to either exposure to pollen or contact with apple onto the oro-pharyngeal mucosa.

Vaccination with a peptide containing a T cell epitope from the allergen Bet v 1 from birch pollen modified as to contain a redox moiety elicits cytolytic regulatory T cells that eliminate symptoms related to birch pollen exposure and those resulting from ingestion of fruits carrying a homologous T cell epitope.

The invention claimed is:

1. A method for treating an allergic condition in an individual, comprising administering to said individual an isolated immunogenic peptide with a length of at most 75 amino acids, wherein said immunogenic peptide comprises:
   a T cell epitope sequence of an antigenic protein, wherein said antigenic protein is an allergen and wherein said T cell epitope sequence is an epitope sequence recognized by WIC class II molecules, and
   a [CST]-(X)2-C or C-X(2)-[CST] thioredox sequence motif wherein X is any amino acid,
   said thioredox sequence motif being either adjacent to said epitope sequence, or separated from said epitope sequence by a linker of at most 7 amino acids, wherein said thioredox sequence motif does not naturally occur within a region of 11 amino acids N-terminally or C-terminally of the T cell epitope sequence in said antigenic protein.

2. The method according to claim 1, wherein said T cell epitope sequence has a length of 8 to 16 amino acids.

3. The method according to claim 1, wherein said thioredox sequence motif is separated from said T cell epitope sequence by a linker of at most 4 amino acids.

4. The method according to claim 1, wherein said immunogenic peptide has a length between 12 and 50 amino acids.

5. The method according to claim 1, wherein at least one X in the thioredox sequence motif is Gly, Ala, Ser, Thr, His or Pro.

6. The method according to claim 1, wherein said thioredox sequence motif is positioned N-terminally of said T cell epitope sequence.

7. The method according to claim 1, wherein said allergen is selected from the group consisting of: food allergens, house dust mites allergens, allergens from insects, allergens from pollen, allergens from animals, allergens from fungi, and occupational allergens.

8. The method according to claim 7, wherein said allergen is selected from the group consisting of Betula Bet v1 allergen, Bovine beta-lactoglobulin and Der p1.

* * * * *

UNITED STATES PATENT AND TRADEMARK OFFICE
CERTIFICATE OF CORRECTION

PATENT NO. : 11,718,650 B2
APPLICATION NO. : 16/848086
DATED : August 8, 2023
INVENTOR(S) : Jean-Marie Saint-Remy Page 1 of 1

It is certified that error appears in the above-identified patent and that said Letters Patent is hereby corrected as shown below:

In the Claims

Column 81, Line 45: Please change "WIC claim II" to --MHC class II--

Signed and Sealed this
Fifth Day of December, 2023

Katherine Kelly Vidal
*Director of the United States Patent and Trademark Office*